(12) United States Patent
Sears et al.

(10) Patent No.: US 10,203,329 B2
(45) Date of Patent: Feb. 12, 2019

(54) BIOFILM FORMATION TO DEFINE RISK FOR COLON CANCER

(71) Applicant: The Johns Hopkins University, Baltimore, MD (US)

(72) Inventors: Cynthia L. Sears, Baltimore, MD (US); Drew M. Pardoll, Brookeville, MD (US); Christine Craig, Baltimore, MD (US); Elizabeth Wick, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 15/021,313

(22) PCT Filed: Sep. 11, 2014

(86) PCT No.: PCT/US2014/055123
§ 371 (c)(1),
(2) Date: Mar. 11, 2016

(87) PCT Pub. No.: WO2015/038731
PCT Pub. Date: Mar. 19, 2015

(65) Prior Publication Data
US 2016/0223553 A1 Aug. 4, 2016

Related U.S. Application Data

(60) Provisional application No. 61/876,995, filed on Sep. 12, 2013.

(51) Int. Cl.
| | | |
|---|---|---|
| G01N 33/574 | (2006.01) | |
| A61K 31/7056 | (2006.01) | |
| A61K 31/165 | (2006.01) | |
| A61K 31/43 | (2006.01) | |
| A61K 31/546 | (2006.01) | |
| A61K 31/7048 | (2006.01) | |
| A61K 31/407 | (2006.01) | |
| A61K 35/741 | (2015.01) | |
| A61K 35/742 | (2015.01) | |
| A61K 35/744 | (2015.01) | |
| A61K 35/745 | (2015.01) | |
| A61K 35/747 | (2015.01) | |
| A61K 45/06 | (2006.01) | |
| C12Q 1/6841 | (2018.01) | |
| C12Q 1/6869 | (2018.01) | |

(52) U.S. Cl.
CPC ..... *G01N 33/57419* (2013.01); *A61K 31/165* (2013.01); *A61K 31/407* (2013.01); *A61K 31/43* (2013.01); *A61K 31/546* (2013.01); *A61K 31/7048* (2013.01); *A61K 31/7056* (2013.01); *A61K 35/741* (2013.01); *A61K 35/742* (2013.01); *A61K 35/744* (2013.01); *A61K 35/745* (2013.01); *A61K 35/747* (2013.01); *A61K 45/06* (2013.01); *C12Q 1/6841* (2013.01); *C12Q 1/6869* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 2004/0077093 A1 | 4/2004 | Pan | |
| 2011/0171123 A1* | 7/2011 | Shirtliff | A61K 49/1875 424/1.11 |
| 2012/0288571 A1 | 11/2012 | Tennican et al. | |
| 2013/0052182 A1 | 2/2013 | Miller | |
| 2014/0107092 A1* | 4/2014 | Meyerson | C12Q 1/689 514/196 |

FOREIGN PATENT DOCUMENTS

KR 1020100099213 A 9/2010

OTHER PUBLICATIONS

Filho et al., "Morphological, biochemical, physiological and molecular aspects of the response of Fusobacterium nucleatum exposed to subinhibitory concentrations of antimicrobials", Anaerobe 2012, vol. 18, pp. 566-575.*
Chen et al., "Human Intestinal Lumen and Mucosa-Associated Microbiota in Patients with Colorectal Cancer", PLoS ONE 2012, vol. 7, article e39743, pp. 1-9.*
Warren et al., "Co-occurrence of anaerobic bacteria in colorectal carcinomas", Microbiome 2013, vol. 1, pp. 1-12.*
Macfarlane et al. Composition and metabolic activities of bacterial biofilms colonizing food residues in the human gut. Environmental Microbiology. 2006. vol. 72, No. 9, pp. 6204-6211.

* cited by examiner

*Primary Examiner* — Michelle F. Paguio Frising
(74) *Attorney, Agent, or Firm* — Mintz Levin Cohn Ferris Glovsky and Popeo, P.C.; Peter F. Corless

(57) ABSTRACT

Methods of identifying subjects at increased risk of cancer, based upon detection of biofilms and/or biofilm-associated microbes within a subject, are disclosed. Therapies designed to prevent formation and/or reduce the size of biofilms in a subject identified to be at increased risk of cancer based upon detection of biofilms and/or biofilm-associated microbes are disclosed. In particular embodiments, the invention provides for identification of a subject at elevated risk of developing or having colorectal cancer and/or a colorectal adenoma, based upon detection of a biofilm and/or biofilm-associated bacteria within the gastrointestinal tract of the subject (optionally, within a biopsy specimen and/or stool sample of such subject). Therapies involving administration of an antibiotic agent and/or a probiotic agent to a subject, to prevent or reduce biofilm formation within the gastrointestinal tract of the subject, optionally provided in combination with additional cancer therapy, are also disclosed.

21 Claims, 75 Drawing Sheets

FIG. 2B
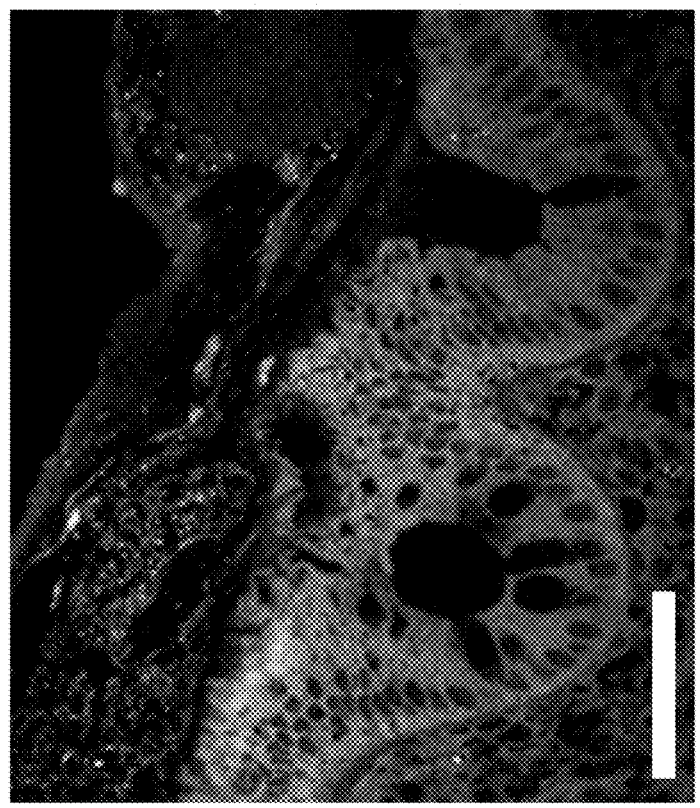
Left distal normal surgery
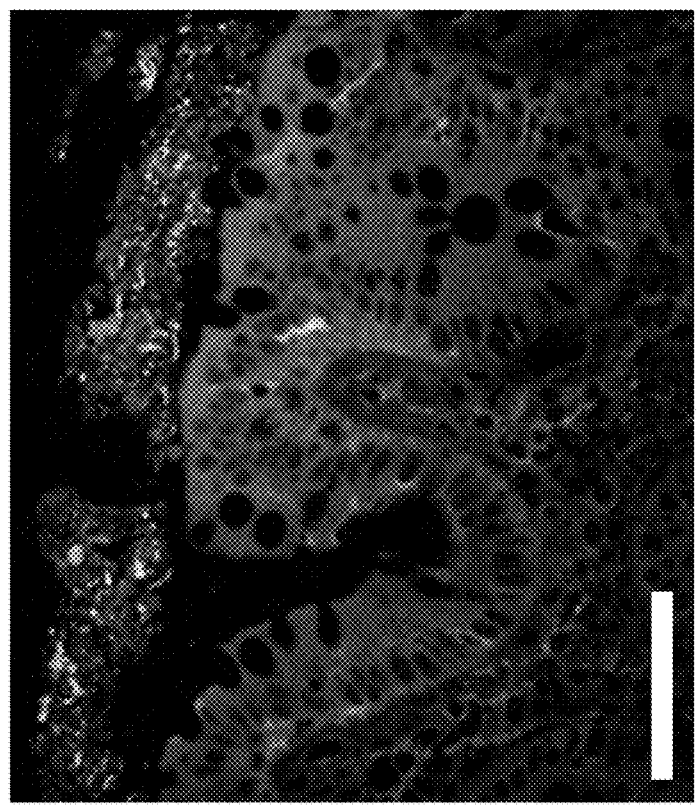
Right distal normal surgery

FIG. 2C
Right colonoscopy bx
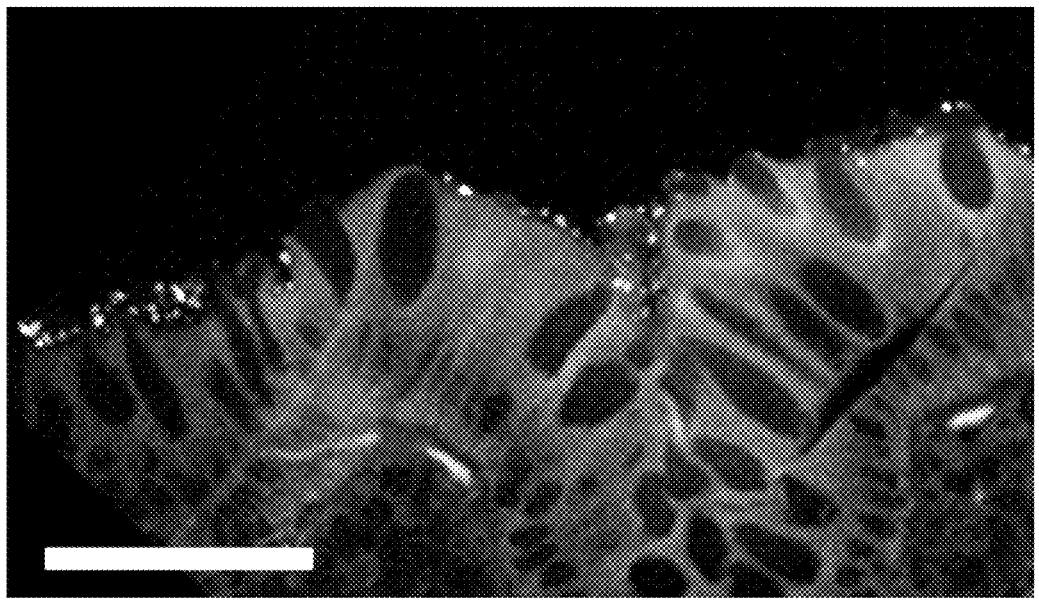
Left colonoscopy bx
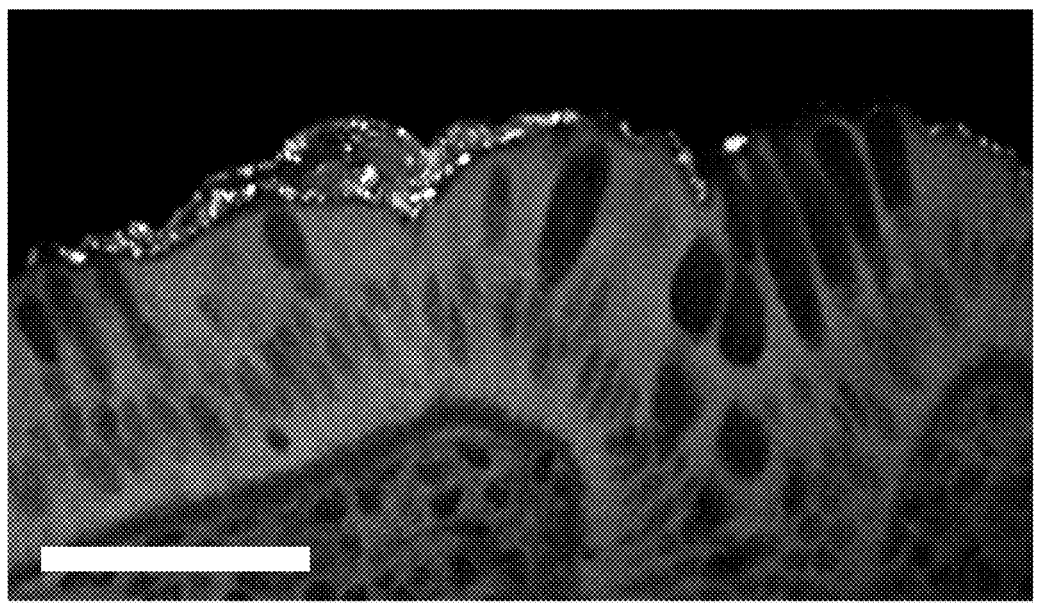

Right Distal Normal Surgery

FIG. 3A
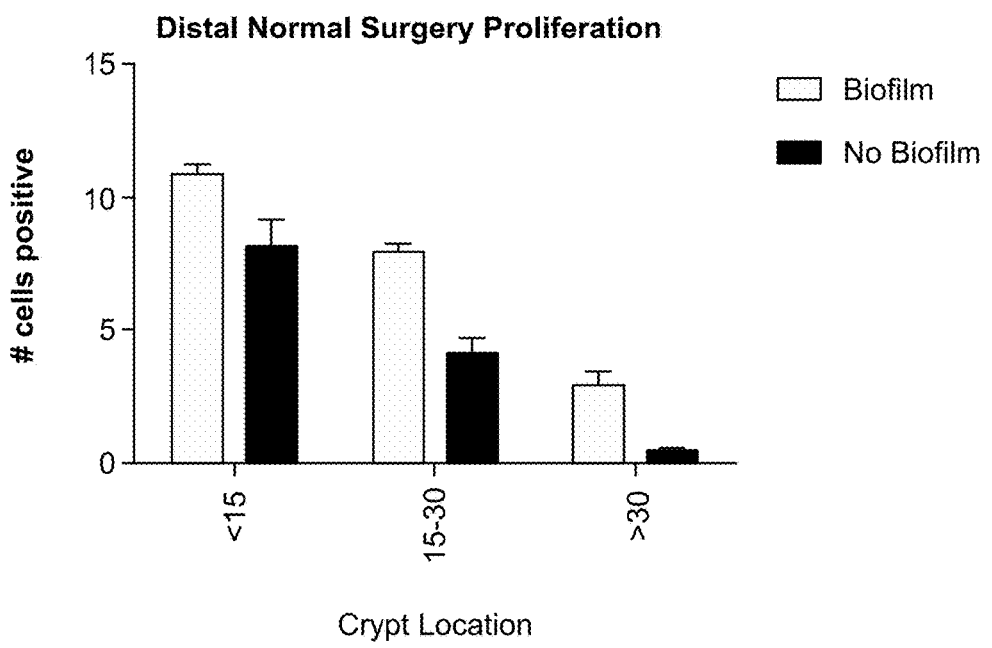
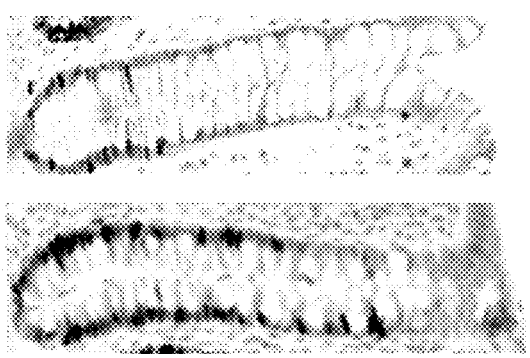
L Distal Normal Surgery CRC mucosa bf⁻
L Distal Normal Surgery CRC mucosa bf⁺

FIG. 3B
Distal Normal Surgery Proliferation
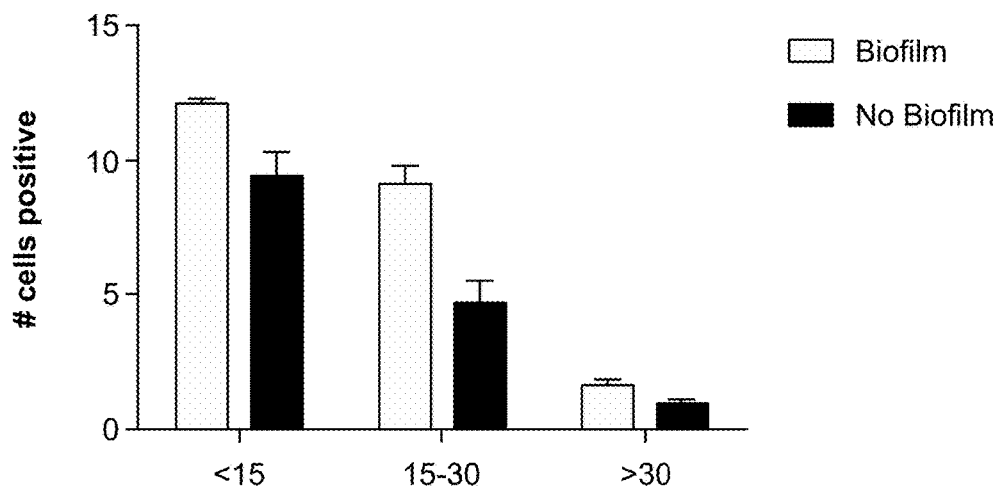
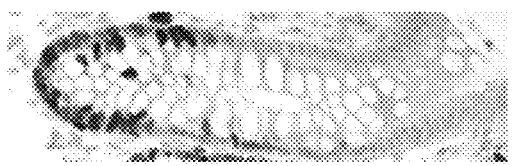
L colonoscopy bx bf⁻
L colonoscopy bx bf⁺

Distal Normal Surgery Apoptosis

Colonoscopy Biopsy Apoptosis

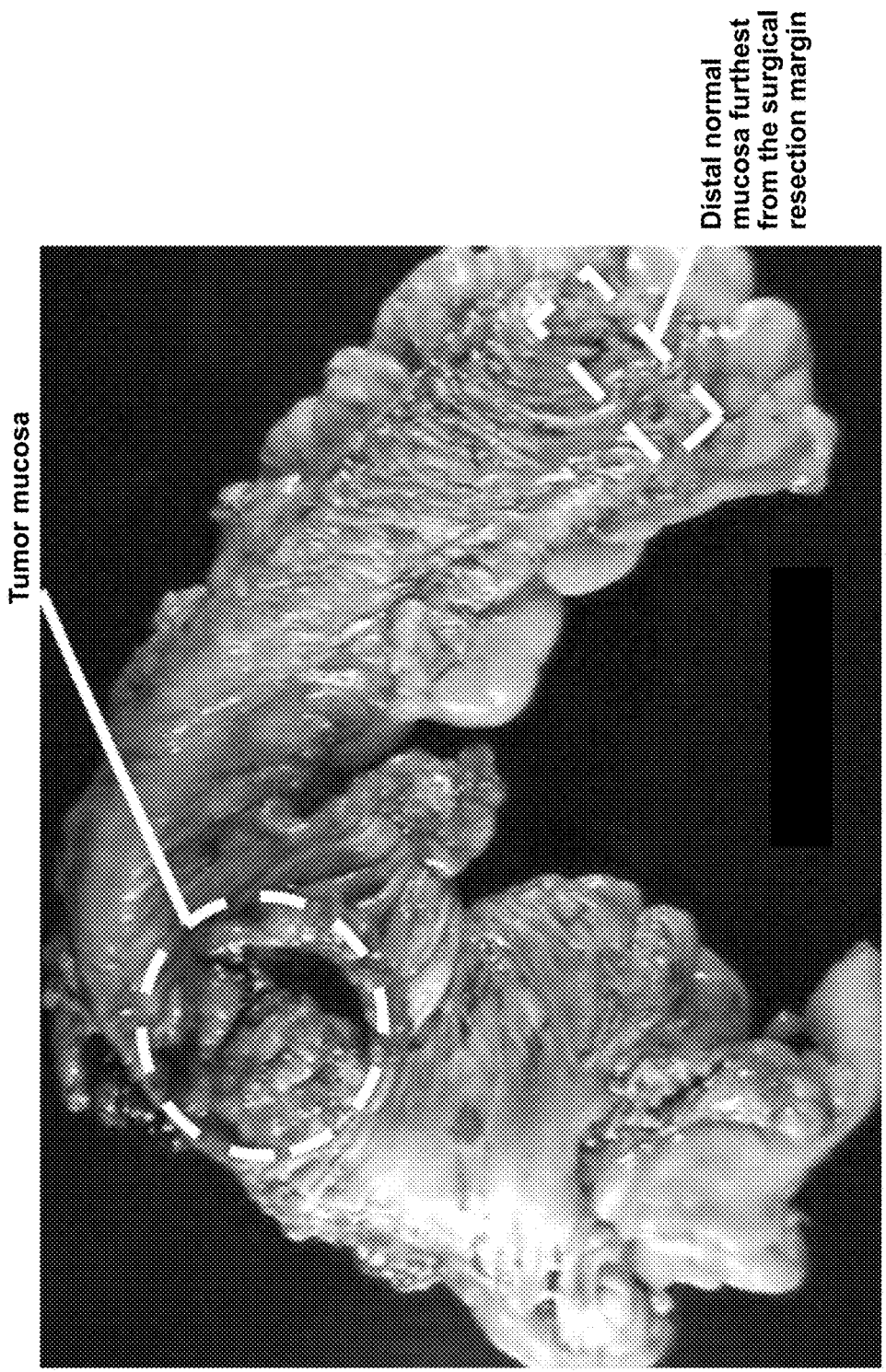

Left CRC Without a Biofilm

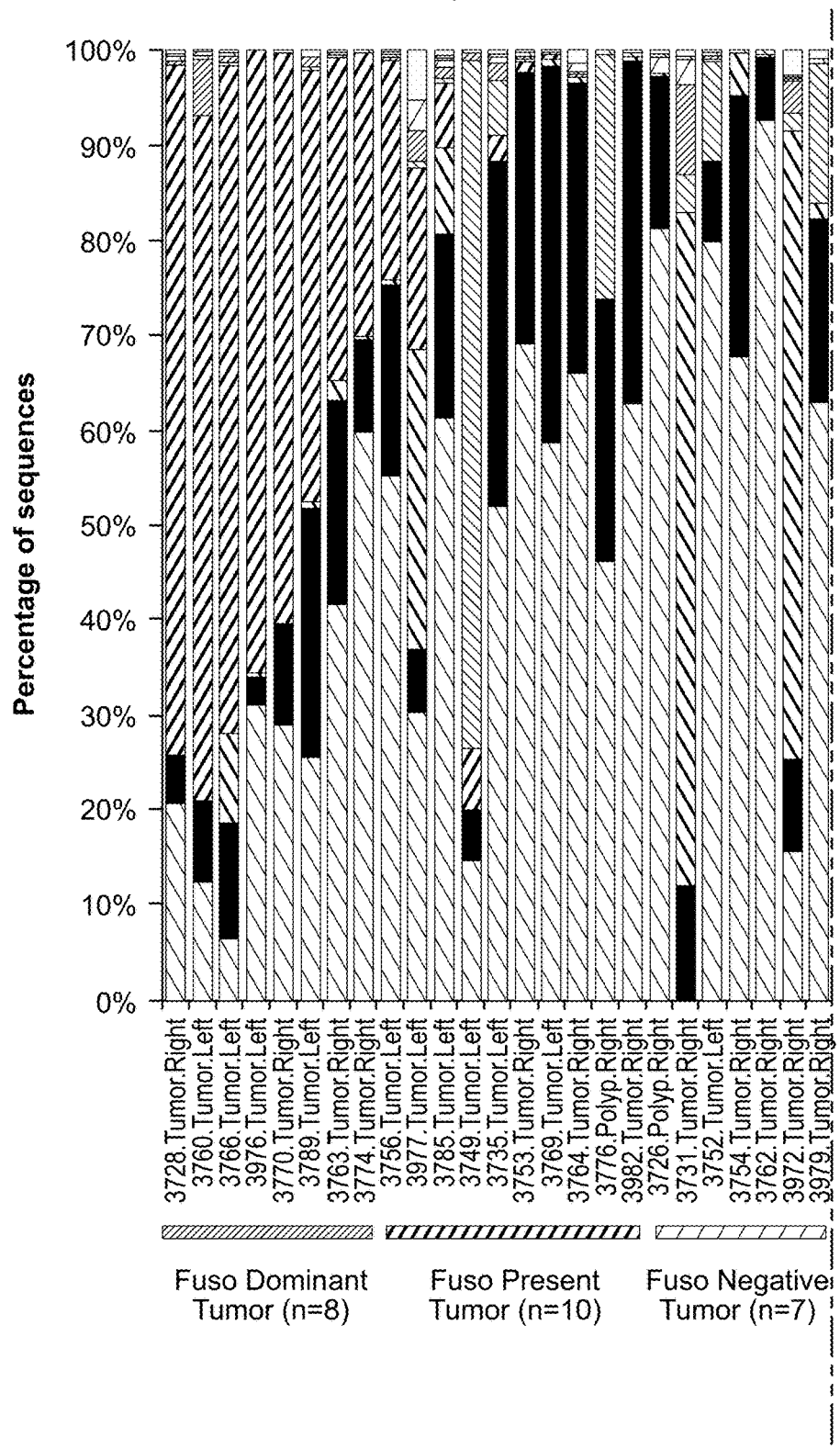

FIG. 9

| Patient ID | Patient Type | Age | Sex | Race | Tumor Site | Biofilm | Stage | Tumor Size (mm) | KRAS | BRAF | MSI | Histology |
|---|---|---|---|---|---|---|---|---|---|---|---|---|
| 3972 | Surgical CRC | 78 | M | Caucasian | Cecum | Yes | 3 | 40.0 | mut | wt | Stable | Adenocarcinoma |
| 3979 | Surgical CRC | 77 | F | African American | Cecum | Yes | 3 | 35.0 | mut | wt | Stable | Adenocarcinoma |
| 3726 | Surgical Polyp | 50 | M | Caucasian | Ascending | Yes | NA | 40.0 | wt | wt | Stable | Tubular adenoma-no dysplasia |
| 3728 | Surgical CRC | 59 | M | Caucasian | Ascending | Yes | 1 | 87.0 | wt | wt | Stable | Adenocarcinoma |
| 3731 | Surgical CRC | 74 | M | Caucasian | Ascending | Yes | 2 | 30.0 | wt | mut | High | Adenocarcinoma |
| 3741 | Surgical CRC | 54 | M | Caucasian | Ascending | Yes | 1 | 8.0 | wt | wt | Stable | Adenocarcinoma |
| 3753 | Surgical CRC | 49 | F | African American | Ascending | Yes | 4 | 47.0 | wt | wt | Stable | Mucinous Adenocarcinoma |
| 3754 | Surgical CRC | 57 | F | African American | Ascending | Yes | 2 | 30.0 | wt | mut | Stable | Adenocarcinoma |
| 3762 | Surgical CRC | 73 | M | Caucasian | Ascending | Yes | 4 | 54.0 | wt | wt | Stable | Adenocarcinoma |
| 3763 | Surgical CRC | 66 | F | Caucasian | Ascending | Yes | 2 | 30.0 | wt | wt | Stable | Adenocarcinoma |
| 3764 | Surgical CRC | 59 | F | Caucasian | Ascending | Yes | 4 | 22.0 | wt | wt | Stable | Adenocarcinoma |
| 3776 | Surgical Polyp | 84 | F | Caucasian | Ascending | Yes | NA | 35.0 | ND | ND | ND | Tubular adenoma-no dysplasia |
| 3982 | Surgical CRC | 62 | M | Caucasian | Ascending | Yes | 2 | 45.0 | ND | wt | High | Mucinous Adenocarcinoma |
| 3984 A/B* | Surgical Polyp/ Surgical Polyp | 47 | M | Caucasian | Ascending/ Ascending | Yes/Yes | NA | 33.0/8.0 | ND | ND | ND | Tubular adenoma-no dysplasia/ Tubular adenoma-no dysplasia |
| 3987 | Surgical CRC | 66 | F | Caucasian | Ascending | Yes | 2 | 50.0 | wt | mut | High | Mucinous Adenocarcinoma |

FIG. 9 Cont.

| | | | | | | | | | | |
|---|---|---|---|---|---|---|---|---|---|---|
| 3986 | Surgical CRC | 59 | M | Caucasian | Hepatic Flexure | No | 2 | 50.0 | wt | wt | Stable | Adenocarcinoma |
| 3770 | Surgical CRC | 71 | M | Caucasian | Hepatic Flexure | No | 1 | 35.0 | wt | wt | High | Adenocarcinoma |
| 3774 | Surgical CRC | 45 | M | Asian | Hepatic Flexure | Yes | 2 | 45.0 | wt | wt | High | Adenocarcinoma |
| 3752 | Surgical CRC | 73 | F | Caucasian | Transverse | No | 2 | 25.0 | mut | wt | Stable | Adenocarcinoma |
| 3976 | Surgical CRC | 52 | F | Caucasian | Transverse | No | 1 | 20.0 | mut | wt | High | Mucinous Adenocarcinoma |
| 3768 | Surgical CRC | 45 | M | African American | Transverse | No | 4 | 42.0 | mut | wt | Stable | Adenocarcinoma |
| 4017 A/B* | Surgical Polyp/ Surgical Polyp | 64 | F | African American | Transverse/ Transverse | No/No | NA | 30.0/60.0 | ND | ND | ND | Tubulovillous adenoma-no dysplasia/ Tubulovillous adenoma-no dysplasia |
| 3769 | Surgical CRC | 78 | F | African American | Rectosigmoid | No | 3 | 60.0 | wt | wt | Stable | Adenocarcinoma |
| 3992 | Surgical CRC | 91 | F | Caucasian | Splenic Flexure | Yes | 2 | 45.0 | wt | mut | High | Adenocarcinoma |
| 3789 | Surgical CRC | 55 | M | Hispanic | Descending | No | 3 | 50.0 | wt | wt | Stable | Adenocarcinoma |
| 3988 | Surgical CRC | 48 | M | Caucasian | Descending | No | 1 | 35.0 | wt | wt | Stable | Mucinous Adenocarcinoma |
| 3749 | Surgical CRC | 39 | M | Caucasian | Sigmoid | No | 3 | 50.0 | wt | wt | Stable | Adenocarcinoma |
| 3756 | Surgical CRC | 54 | M | Caucasian | Sigmoid | Yes | 4 | 45.0 | wt | wt | Stable | Adenocarcinoma |
| 3766 | Surgical CRC | 56 | F | Caucasian | Sigmoid | No | 4 | 55.0 | wt | wt | Stable | Adenocarcinoma |
| 3977 | Surgical CRC | 38 | F | Caucasian | Sigmoid | No | 1 | 50.0 | wt | wt | Stable | Adenocarcinoma |
| 3760 | Surgical CRC | 29 | F | Caucasian | Rectosigmoid | No | 2 | 80.0 | wt | wt | Stable | Adenocarcinoma |
| 3785 | Surgical CRC | 54 | F | Caucasian | Rectosigmoid | No | 3 | 40.0 | wt | wt | Stable | Adenocarcinoma |
| 4009 | Surgical CRC | 53 | M | Caucasian | Rectosigmoid | No | 3 | 86.0 | wt | wt | Stable | Adenocarcinoma |
| 3735 | Surgical CRC | 64 | M | Caucasian | Rectum | No | 3 | 70.0 | mut | wt | Stable | Adenocarcinoma |
| 3978 | Surgical CRC | 90 | F | Caucasian | Rectum | No | 1 | 27.0 | wt | wt | Stable | Mucinous Adenocarcinoma |

FIG. 10A

| Patient ID | Age | Sex | Race | Bowel Prep | Biopsy Sto | Bioflm |
|---|---|---|---|---|---|---|
| 1 | 31 | F | African American | GoLytelyPrep | Descending | Yes |
| | | | | | Ascending | No |
| 2* | 66 | F | Caucasian | GoLytelyPrep | Descending | No |
| | | | | | Ascending | No |
| 3 | 66 | M | African American | GoLytelyPrep | Descending | Yes |
| | | | | | Ascending | Yes |
| 4* | 66 | M | African American | GoLytelyPrep | Descending | No |
| | | | | | Ascending | No |
| 5* | 44 | F | Caucasian | GoLytelyPrep | Descending | No |
| | | | | | Ascending | No |
| 6 | 52 | F | Caucasian | GoLytelyPrep | Descending | No |
| | | | | | Ascending | No |
| 7 | 74 | M | Caucasian | GoLytelyPrep | Descending | No |
| | | | | | Ascending | No |
| 8 | 51 | F | African American | GoLytelyPrep &Miralax | Descending | No |
| | | | | | Ascending | Yes |
| 9 | 75 | M | African American | GoLytelyPrep | Descending | No |
| | | | | | Ascending | Yes |
| 10* | 40 | F | Caucasian | GoLytelyPrep | Descending | No |
| | | | | | Ascending | No |
| 11* | 42 | F | Hispanic | GoLytelyPrep | Descending | No |
| | | | | | Ascending | No |
| 12* | 45 | F | Caucasian | MiralaxPrep | Descending | No |
| | | | | | Ascending | No |
| 13 | 62 | M | African American | GoLytelyPrep | Descending | No |
| | | | | | Ascending | No |
| 14* | 75 | M | Caucasian | GoLytelyPrep | Descending | No |
| | | | | | Ascending | No |
| 15 | 44 | M | Caucasian | MiralaxPrep | Descending | No |
| | | | | | Ascending | No |
| 17 | 71 | F | African American | GoLytelyPrep | Descending | No |
| | | | | | Ascending | No |
| 18 | 74 | F | African American | MiralaxPrep | Descending | No |
| | | | | | Ascending | No |
| 19 | 62 | M | African American | GoLytelyPrep | Descending | No |
| | | | | | Ascending | No |
| 20 | 35 | M | African American | GoLytelyPrep | Descending | No |
| | | | | | Ascending | No |

* patient underwent diagnostic workup

FIG. 10B

| | | | | | Descending | No |
|---|---|---|---|---|---|---|
| 21* | 49 | F | Asian | MiralaxPrep | Descending | No |
| | | | | | Ascending | No |
| 22* | 47 | M | African American | GoLytelyPrep | Descending | No |
| | | | | | Ascending | No |
| 23* | 78 | F | Caucasian | Mag Citrate + L-DucolaxPrep | Descending | No |
| | | | | | Ascending | No |
| 24* | 47 | M | African American | MiralaxPrep | Descending | No |
| | | | | | Ascending | No |
| 25* | 65 | M | African American | GoLytelyPrep | Descending | No |
| | | | | | Ascending | No |
| 26* | 39 | F | African American | MiralaxPrep | Descending | No |
| | | | | | Ascending | No |
| 27 | 51 | F | African American | GoLytelyPrep | Descending | No |
| | | | | | Ascending | No |
| 28 | 47 | F | Caucasian | MiralaxPrep | Descending | No |
| | | | | | Ascending | No |
| 29* | 64 | F | Caucasian | GoLytelyPrep | Descending | No |
| | | | | | Ascending | No |
| 30 | 51 | M | Caucasian | MiralaxPrep | Descending | No |
| | | | | | Ascending | No |
| 31* | 65 | M | African American | MiralaxPrep | Descending | No |
| | | | | | Ascending | No |
| 32* | 55 | F | African American | MiralaxPrep | Descending | No |
| | | | | | Ascending | No |
| 33 | 56 | M | Asian | MiralaxPrep | Descending | No |
| | | | | | Ascending | No |
| 34 | 66 | F | Caucasian | MiralaxPrep | Descending | No |
| | | | | | Ascending | No |
| 35 | 60 | F | Caucasian | MiralaxPrep | Descending | No |
| | | | | | Ascending | No |
| 36 | 79 | F | African American | MiralaxPrep | Descending | No |
| | | | | | Ascending | No |
| 37 | 66 | M | Caucasian | MiralaxPrep | Descending | No |
| | | | | | Ascending | Yes |
| 38 | 59 | M | Caucasian | MiralaxPrep | Descending | Yes |
| | | | | | Ascending | Yes |
| 39 | 72 | F | African American | MiralaxPrep | Descending | Yes |
| | | | | | Ascending | Yes |
| 40 | 58 | F | African American | GoLytelyPrep | Descending | No |
| | | | | | Ascending | No |
| 41 | 46 | F | Asian | GoLytelyPrep | Descending | Yes |
| | | | | | Ascending | Yes |
| 42* | 69 | M | African American | MiralaxPrep | Descending | Yes |
| | | | | | Ascending | Yes |

\* patient underwent diagnostic workup

FIG. 10C

| | | | | | Descending | No |
|---|---|---|---|---|---|---|
| 45 | 62 | F | African American | GoLytelyPrep | Descending | No |
| | | | | | Ascending | No |
| 44* | 47 | F | Caucasian | GoLytelyPrep | Descending | No |
| | | | | | Ascending | No |
| 45* | 75 | M | African American | GoLytelyPrep | Descending | No |
| | | | | | Ascending | No |
| 46 | 65 | F | African American | GoLytelyPrep | Descending | No |
| | | | | | Ascending | No |
| 47* | 66 | M | Caucasian | MiralaxPrep | Descending | No |
| | | | | | Ascending | No |
| 48 | 56 | F | African American | GoLytelyPrep | Descending | No |
| | | | | | Ascending | No |
| 49 | 65 | F | African American | GoLytelyPrep | Descending | No |
| | | | | | Ascending | No |
| 50 | 64 | M | Other | GoLytelyPrep | Descending | No |
| | | | | | Ascending | No |
| 52* | 45 | F | Caucasian | NuLytelyPrep | Descending | No |
| | | | | | Ascending | No |
| 55 | 47 | M | Caucasian | GoLytelyPrep | Descending | No |
| | | | | | Ascending | No |
| 54 | 55 | M | Caucasian | NuLytelyPrep | Descending | No |
| | | | | | Ascending | No |
| 55 | 60 | F | African American | GoLytelyPrep | Descending | No |
| | | | | | Ascending | No |
| 56 | 52 | F | African American | GoLytelyPrep | Descending | No |
| | | | | | Ascending | Yes |
| 57* | 52 | M | Caucasian | TriLytelyPrep | Descending | No |
| | | | | | Ascending | No |
| 58 | 57 | F | African American | MiralaxPrep | Descending | No |
| | | | | | Ascending | No |
| 59 | 77 | M | African American | NuLytely& MiralaxPrep | Descending | No |
| | | | | | Ascending | No |
| 60* | 45 | F | Caucasian | TriLytePrep | Descending | No |
| | | | | | Ascending | No |
| 61 | 55 | M | Caucasian | MiralaxPrep | Descending | No |
| | | | | | Ascending | No |
| 62 | 62 | M | African American | GoLytelyPrep | Descending | Yes |
| | | | | | Ascending | No |

\* patient underwent diagnostic workup

FIG. 11

| Probe Target(s) | Probe Name | Probe Sequence (5'-3') | Reference |
|---|---|---|---|
| virtually all bacteria, Kingdom (Eu)Bacteria | Eub338 | GCTGCCTCCCGTAGGAGT | 14 |
| Fusobacteria | Fus714 | GGCTTCCCCATCGGCATT | 15 |
| Prevotello | PRV392 | GCACGCTACTTGGCTGG | 16 |
| Bacteroides, Parabacteroides, Prevotella | CFB286 | TCCTCTCAGAACCCCTAC | 17 |
| Betaproteobacteria | Bet42a | GCCTTCCCACTTCGTTT | 24 |
| Gammaproteobacteria | Gam42a | GCCTTCCCACATCGTTT | 24 |
| Lachnospiraceae | Lac435 | TCTTCCCTGCTGATAGA | 18 |
| Enterobacteriacea except Proteus spp | Ent186 | CCCCWCTTTGGTGTTGC | 19 |
| Bacteroides fragilis | S-S-Bfrag-998-a-A-20 | GTTTCCACATCATTCCACTG | 22 |
| Escherichia coli, Shigella | Eco1167 | GCATAAGCGTCGCTGCCG | 20 |
| Streptococcus | Str405 | TAGCCGTCCCTTTCTGGT | 23 |
| nonsense probe | non338 | ACTCCTACGGGAGGCAGC | 21 |

FIG. 12A

16S V3-V5 amplicon sequencing statistics by sample.

| Sample Name | Sequences passing quality filtering | % detected as chimeras | % detected as chloroplast | Final sequence count | Final avg read length | Length distribution ||||| 
|---|---|---|---|---|---|---|---|---|---|---|
| | | | | | | Min final length | Q1 | Median | Q3 | Max final length |
| 3726.Normal.Right | 10288 | 7.51 | 0.00 | 9515 | 302.8 | 150 | 270 | 287 | 343 | 519 |
| 3726.Polyp.Right | 11852 | 10.51 | 0.00 | 10606 | 308.2 | 150 | 272 | 293 | 348 | 521 |
| 3728.Normal.Right | 6906 | 2.43 | 0.00 | 6738 | 272.3 | 150 | 241 | 280 | 302 | 470 |
| 3728.Tumor.Right | 18644 | 7.27 | 0.00 | 17288 | 426.4 | 150 | 403 | 433 | 503 | 546 |
| 3731.Normal.Right | 12470 | 23.88 | 0.00 | 9492 | 337.2 | 150 | 290 | 347 | 374 | 527 |
| 3731.Tumor.Right | 8305 | 8.51 | 0.00 | 7598 | 328.5 | 151 | 282 | 323 | 396 | 516 |
| 3735.Normal.Left | 7991 | 8.51 | 0.03 | 7309 | 278.6 | 150 | 245 | 282 | 305 | 513 |
| 3735.Tumor.Left | 17136 | 27.96 | 0.01 | 12344 | 437.7 | 150 | 415 | 453 | 503 | 547 |
| 3749.Normal.Left | 7245 | 4.29 | 0.01 | 6933 | 268.9 | 150 | 233 | 267 | 302 | 512 |
| 3749.Tumor.Left | 17698 | 4.84 | 0.00 | 15842 | 396.8 | 150 | 281 | 427 | 479 | 543 |
| 3752.Normal.Left | 5624 | 7.97 | 0.00 | 5176 | 271.3 | 150 | 242 | 275 | 299 | 506 |
| 3752.Tumor.Left | 21210 | 20.32 | 0.00 | 16900 | 402.4 | 150 | 338 | 425 | 453 | 552 |
| 3753.Normal.Right | 36923 | 16.34 | 0.00 | 30890 | 426.2 | 150 | 401 | 442 | 500 | 553 |
| 3753.Tumor.Right | 43747 | 16.66 | 0.00 | 36460 | 430.5 | 150 | 406 | 444 | 502 | 546 |
| 3754.Normal.Right | 24558 | 28.67 | 0.00 | 17516 | 439.9 | 150 | 422 | 454 | 504 | 546 |
| 3754Tumor.Right | 43254 | 19.43 | 0.00 | 34851 | 435.0 | 150 | 412 | 451 | 502 | 541 |
| 3756.Normal.Left | 9929 | 13.81 | 0.00 | 8558 | 416.7 | 150 | 397 | 433 | 457 | 548 |
| 3756. Tumor.Left | 16532 | 30.80 | 0.00 | 11440 | 421.2 | 150 | 378 | 435 | 496 | 546 |
| 3760.Normal.Left | 8507 | 16.70 | 0.16 | 7075 | 446.7 | 150 | 420 | 466 | 506 | 541 |
| 3760.Tumor.Left | 18784 | 13.81 | 0.00 | 15189 | 422.4 | 150 | 403 | 431 | 489 | 543 |

FIG. 12B

16S V3-V5 amplicon sequencing statistics by sample.

| Sample Name | Sequences passing quality filtering | % detected as chimeras | % detected as chloroplast | Final sequence count | Final avg read length | Length distribution | | | | |
|---|---|---|---|---|---|---|---|---|---|---|
| | | | | | | Min final length | Q1 | Median | Q3 | Max final length |
| 3762.Normal.Right | 13214 | 5.16 | 0.00 | 12532 | 304.8 | 150 | 266 | 289 | 349 | 521 |
| 3762.Tumor.Right | 10709 | 2.94 | 0.00 | 10394 | 298.0 | 150 | 260 | 283 | 340 | 521 |
| 3763.Normal.Right | 22737 | 15.01 | 0.00 | 19325 | 438.8 | 150 | 412 | 452 | 500 | 559 |
| 3763.Tumor.Right | 17857 | 16.40 | 0.00 | 14929 | 411.8 | 150 | 386 | 425 | 460 | 557 |
| 3764.Normal.Right | 8237 | 17.71 | 0.00 | 6778 | 312.3 | 150 | 272 | 302 | 353 | 519 |
| 3764.Tumor.Right | 10971 | 11.86 | 0.00 | 9670 | 314.6 | 150 | 272 | 306 | 355 | 537 |
| 3766.Normal.Left | 12039 | 8.48 | 0.05 | 11013 | 393.3 | 150 | 303 | 424 | 458 | 536 |
| 3766.Tumor.Left | 10238 | 8.52 | 0.01 | 9365 | 428.8 | 150 | 408 | 435 | 502 | 534 |
| 3769.Normal.Left | 14234 | 34.97 | 0.00 | 9257 | 416.5 | 150 | 356 | 434 | 498 | 538 |
| 3769.Tumor.Left | 11543 | 29.68 | 0.00 | 8117 | 417.6 | 151 | 364 | 433 | 498 | 540 |
| 3770.Normal.Right | 11931 | 13.15 | 0.00 | 10362 | 304.7 | 150 | 265 | 290 | 345 | 515 |
| 3770.Tumor.Right | 9835 | 6.41 | 0.00 | 9205 | 332.1 | 150 | 278 | 331 | 399 | 513 |
| 3774.Normal.Right | 14961 | 9.24 | 0.00 | 13578 | 406.0 | 150 | 352 | 424 | 451 | 534 |
| 3774.Tumor.Right | 11286 | 16.52 | 0.00 | 9421 | 413.7 | 150 | 388 | 427 | 463 | 538 |
| 3776.Normal.Right | 11967 | 15.70 | 0.00 | 10088 | 395.8 | 150 | 328 | 423 | 453 | 533 |
| 3776.Polyp.Right | 8999 | 24.46 | 0.00 | 6798 | 407.2 | 150 | 352 | 426 | 462 | 536 |
| 3785.Normal.Left | 10912 | 8.92 | 0.01 | 9938 | 420.8 | 150 | 401 | 435 | 462 | 543 |
| 3785.Tumor.Left | 10134 | 21.81 | 0.01 | 7923 | 422.9 | 150 | 398 | 434 | 488 | 534 |
| 3789.Normal.Left | 7107 | 15.65 | 0.00 | 5995 | 417.2 | 150 | 392 | 432 | 460 | 536 |
| 3789.Tumor.Left | 9462 | 26.08 | 0.00 | 6994 | 423.2 | 150 | 405 | 430 | 477 | 538 |

FIG. 12C

16S V3-V5 amplicon sequencing statistics by sample.

| Sample Name | Sequences passing quality filtering | % detected as chimeras | % detected as chloroplast | Final sequence count | Final avg read length | Length distribution ||||  |
|---|---|---|---|---|---|---|---|---|---|---|
| | | | | | | Min final length | Q1 | Median | Q3 | Max final length |
| 3972.Normal.Right | 8144 | 13.70 | 0.00 | 7028 | 316.2 | 150 | 273 | 300 | 356 | 519 |
| 3972.Tumor.Right | 9159 | 7.20 | 0.00 | 8500 | 324.0 | 150 | 276 | 313 | 391 | 516 |
| 3975.Normal.Left | 10878 | 7.99 | 0.00 | 10009 | 304.1 | 150 | 266 | 289 | 345 | 533 |
| 3976.Tumor.Left | 11612 | 5.09 | 0.00 | 11021 | 348.0 | 150 | 296 | 353 | 408 | 512 |
| 3977.Normal.Left | 10624 | 11.46 | 0.00 | 9407 | 315.7 | 150 | 273 | 302 | 363 | 526 |
| 3977.Tumor.Left | 8389 | 7.04 | 0.00 | 7798 | 322.6 | 150 | 272 | 314 | 390 | 526 |
| 3979.Normal.Right | 14792 | 22.16 | 0.00 | 11514 | 299.1 | 150 | 262 | 301 | 336 | 523 |
| 3979.Tumor.Right | 11221 | 17.98 | 0.00 | 9203 | 314.0 | 150 | 274 | 314 | 351 | 534 |
| 3982.Normal.Right | 19185 | 13.53 | 0.00 | 16589 | 308.0 | 150 | 265 | 291 | 350 | 533 |
| 3982.Tumor.Right | 21882 | 14.12 | 0.00 | 18792 | 312.3 | 150 | 269 | 296 | 362 | 537 |
| S10.Biopsy.Left | 4144 | 4.95 | 0.23 | 3930 | 309.6 | 150 | 263 | 298 | 354 | 516 |
| S10.Biopsy.Right | 4124 | 10.52 | 0.00 | 3690 | 285.5 | 150 | 262 | 286 | 309 | 523 |
| S11.Biopsy.Left | 2118 | 13.79 | 0.00 | 1826 | 300.3 | 150 | 268 | 290 | 333 | 522 |
| S11.Biopsy.Right | 3109 | 13.03 | 0.00 | 2704 | 297.5 | 150 | 265 | 290 | 328 | 530 |
| S12.Biopsy.Left | 2954 | 15.17 | 0.00 | 2506 | 309.4 | 150 | 273 | 296 | 350 | 532 |
| S12.Biopsy.Right | 4220 | 5.33 | 0.00 | 3995 | 312.9 | 150 | 268 | 301 | 356 | 518 |
| S13.Biopsy.Left | 4054 | 3.70 | 0.00 | 3904 | 316.6 | 150 | 266 | 307 | 363 | 518 |
| S13.Biopsy.Right | 4078 | 3.24 | 0.00 | 3946 | 307.6 | 150 | 265 | 296 | 345 | 520 |
| S14.Biopsy.Left | 3805 | 4.02 | 0.00 | 3652 | 317.2 | 150 | 266 | 306 | 370 | 518 |
| S14.Biopsy.Right | 3979 | 4.72 | 0.21 | 3783 | 319.1 | 150 | 269 | 308 | 364 | 518 |

FIG. 12D

16S V3-V5 amplicon sequencing statistics by sample.

| Sample Name | Sequences passing quality filtering | % detected as chimeras | % detected as chloroplast | Final sequence count | Final avg read length | Length distribution ||||| 
|---|---|---|---|---|---|---|---|---|---|---|
| | | | | | | Min final length | Q1 | Median | Q3 | Max final length |
| S15.Biopsy.Left | 3474 | 10.07 | 0.00 | 3124 | 296.6 | 150 | 273 | 291 | 318 | 522 |
| S15.Biopsy.Right | 3682 | 4.10 | 0.00 | 3531 | 290.5 | 150 | 265 | 287 | 316 | 536 |
| S17.Biopsy.Left | 4505 | 12.08 | 0.03 | 3960 | 308.2 | 150 | 271 | 290 | 346 | 538 |
| S17.Biopsy.Right | 4933 | 12.67 | 0.00 | 4308 | 288.7 | 150 | 262 | 285 | 311 | 525 |
| S18.Biopsy.Left | 3702 | 15.91 | 0.00 | 3113 | 325.3 | 150 | 275 | 318 | 385 | 532 |
| S18.Biopsy.Right | 3653 | 11.06 | 2.19 | 3178 | 324.8 | 150 | 272 | 317 | 383 | 525 |
| S19.Biopsy.Left | 8194 | 1.45 | 0.00 | 8075 | 275.0 | 150 | 255 | 284 | 302 | 479 |
| S19.Biopsy.Right | 7753 | 2.12 | 0.00 | 7589 | 275.2 | 150 | 250 | 280 | 302 | 496 |
| S20.Biopsy.Left | 6736 | 10.39 | 0.00 | 6036 | 290.1 | 150 | 259 | 286 | 320 | 519 |
| S20.Biopsy.Right | 6179 | 8.87 | 0.00 | 5631 | 278.5 | 150 | 248 | 280 | 305 | 535 |
| S21.Biopsy.Left | 4711 | 7.79 | 0.60 | 4318 | 326.1 | 150 | 274 | 318 | 389 | 522 |
| S21.Biopsy.Right | 5428 | 11.20 | 0.02 | 4819 | 326.2 | 150 | 269 | 313 | 392 | 547 |

FIG. 13A

Shared and unique genera in paired tumor and surgically-resected distal normal tissue samples. Genera listed appear with at least 1% abundance in at least one paired sample.

| Subject ID | Tumor Sample | Normal Sample | Tumor Biofilm Status | Normal Biofilm Status | Number Unique Genera in Tumor Sample | Number Shared Genera | Number Unique Genera in Normal Flanking |
|---|---|---|---|---|---|---|---|
| 3726 | 3726.Polyp.Right | 3726.Normal.Right | positive | positive | 1 | 5 | 0 |
| 3728 | 3728.Tumor.Right | 3728.Normal.Right | positive | NA | 0 | 6 | 1 |
| 3731 | 3731.Tumor.Right | 3731.Normal.Right | positive | positive | 1 | 11 | 0 |
| 3735 | 3735.Tumor.Left | 3735.Normal.Left | negative | negative | 2 | 14 | 1 |
| 3749 | 3749.Tumor.Left | 3749.Normal.Left | negative | negative | 1 | 10 | 2 |
| 3752 | 3752.Tumor.Left | 3752.Normal.Left | negative | negative | 0 | 6 | 1 |

FIG. 13A Cont.

| % Tumor seqs in Unique Genera | % Normal flanking seqs in Unique Genera | Unique Genera in Tumor |
|---|---|---|
| 1.58 | 0.00 | Proteobacteria;Alphaproteobacteria;Sphingomonadales; Sphingomonadaceae;Sphingomonas |
| 0.00 | 2.14 | |
| 1.67 | 0.00 | Firmicutes;Bacilli;Lactobacillales; Leuconostocaceae;Weissella |
| 5.11 | 10.18 | Firmicutes;Clostridia;Clostridiales;Peptostreptococcaceae; Peptostreptococcus* Fusobacteria;Fusobacteriales; Fusobacteriaceae;Fusobacterium |
| 6.73 | 11.57 | Fusobacteria;Fusobacteria;Fusobacteriales;Fusobacteriaceae; Fusobacterium |
| 0.00 | 14.19 | |

FIG. 13B

| Subject ID | TumorSample | NormalSample | Tumor Biofilm Status | Normal Biofilm Status |
|---|---|---|---|---|
| 3726 | 3726.Polyp.Right | 3726.Normal.Right | positive | positive |
| 3728 | 3728.Tumor.Right | 3728.Normal.Right | positive | NA |
| 3731 | 3731.Tumor.Right | 3731.Normal.Right | positive | positive |

FIG. 13B Cont.

| Shared Genera | Unique Genera in Normal Flanking |
|---|---|
| Bacteroidetes;Bacteroidetes;Bacteroidales;Bacteroidaceae;Bacteroides*<br>Bacteroidetes;Bacteroidetes;Bacteroidales;Porphyromonadaceae;Parabacteroides*<br>Firmicutes;Clostridia;Clostridiales;Lachnospiraceae;Dorea*<br>Firmicutes;Clostridia;Clostridiales;Lachnospiraceae;LachnospiraceaeIncertaeSedis*<br>Firmicutes;Clostridia;Clostridiales;Ruminococcaceae;RuminococcaceaeIncertaeSedis | |
| Bacteroidetes;Bacteroidetes;Bacteroidales;Bacteroidaceae;Bacteroides*<br>Bacteroidetes;Bacteroidetes;Bacteroidales;Prevotellaceae;Prevotella*<br>Firmicutes;Bacilli;Lactobacillales;Leuconostocaceae;Weissella*<br>Firmicutes;Clostridia;Clostridiales;Lachnospiraceae;LachnospiraceaeIncertaeSedis*<br>Firmicutes;Clostridia;Clostridiales;Ruminococcaceae;Subdoligranulum*<br>Fusobacteria;Fusobacteria;Fusobacteriales;Fusobacteriaceae;Fusobacterium | Firmicutes;Bacilli;Lactobacillales;<br>Streptococcaceae;Lactococcus |
| Firmicutes;Bacilli;Lactobacillales;Streptococcaceae;Lactococcus*<br>Firmicutes;Clostridia;Clostridiales;Lachnospiraceae;LachnospiraceaeIncertaeSedis*<br>Firmicutes;Clostridia;Clostridiales;Lachnospiraceae;Other*<br>Firmicutes;Clostridia;Clostridiales;Ruminococcaceae;Faecalibacterium*<br>Firmicutes;Clostridia;Clostridiales;Ruminococcaceae;Other*<br>Firmicutes;Clostridia;Clostridiales;Ruminococcaceae;RuminococcaceaeIncertaeSedis*<br>Firmicutes;Clostridia;Clostridiales;Ruminococcaceae;Subdoligranulum*<br>Proteobacteria;Betaproteobacteria;Burkholderiales;Comamonadaceae;Comamonas*<br>Proteobacteria;Betaproteobacteria;Burkholderiales;Comamonadaceae;Delftia*<br>Proteobacteria;Betaproteobacteria;Burkholderiales;Comamonadaceae;Other*<br>Proteobacteria;Gammaproteobacteria;Enterobacteriales;Enterobacteriaceae;Other | |

FIG. 13B Cont.

| 3735 | 3735.Tumor.Left | 3735.Normal.Left | negative | negative |
| --- | --- | --- | --- | --- |
| 3749 | 3749.Tumor.Left | 3749.Normal.Left | negative | negative |
| 3752 | 3752.Tumor.Left | 3752.Normal.Left | negative | negative |

FIG. 13B Cont.

| | |
|---|---|
| Bacteroidetes;Bacteroidia;Bacteroidales;Bacteroidaceae;Bacteroides*<br>Bacteroidetes;Bacteroidia;Bacteroidales;Porphyromonadaceae;Parabacteroides*<br>Bacteroidetes;Bacteroidia;Bacteroidales;Rikenellaceae;Alistipes*<br>Firmicutes;Bacilli;Lactobacillales;Streptococcaceae;Lactococcus*<br>Firmicutes;Bacilli;Lactobacillales;Streptococcaceae;Streptococcus*<br>Firmicutes;Clostridia;Clostridiales;Lachnospiraceae;Dorea*<br>Firmicutes;Clostridia;Clostridiales;Lachnospiraceae;Lachnospira*<br>Firmicutes;Clostridia;Clostridiales;Lachnospiraceae;LachnospiraceaeIncertaeSedis*<br>Firmicutes;Clostridia;Clostridiales;Lachnospiraceae;Other*<br>Firmicutes;Clostridia;Clostridiales;Ruminococcaceae;Ruminococcus*<br>Firmicutes;Clostridia;Clostridiales;Ruminococcaceae;Sporobacter*<br>Firmicutes;Clostridia;Clostridiales;Ruminococcaceae;Subdoligranulum*<br>Proteobacteria;Gammaproteobacteria;Enterobacteriales;Enterobacteriaceae;Other | Firmicutes;Bacilli;Lactobacillales;<br>Leuconostocaceae;Weissella |
| Bacteroidetes;Bacteroidia;Bacteroidales;Bacteroidaceae;Bacteroides*<br>Bacteroidetes;Bacteroidia;Bacteroidales;Porphyromonadaceae;Tannerella*<br>Bacteroidetes;Bacteroidia;Bacteroidales;Rikenellaceae;Alistipes*<br>Firmicutes;Bacilli;Lactobacillales;Leuconostocaceae;Leuconostoc*<br>Firmicutes;Bacilli;Lactobacillales;Leuconostocaceae;Weissella*<br>Firmicutes;Bacilli;Lactobacillales;Streptococcaceae;Lactococcus*<br>Firmicutes;Clostridia;Clostridiales;Lachnospiraceae;LachnospiraceaeIncertaeSedis*<br>Firmicutes;Clostridia;Clostridiales;Lachnospiraceae;Faecalibacterium*<br>Firmicutes;Clostridia;Clostridiales;Ruminococcaceae;Subdoligranulum*<br>Proteobacteria;Gammaproteobacteria;Enterobacteriales;Enterobacteriaceae;Other | Firmicutes;Bacilli;Lactobacillales;Other*<br>Proteobacteria;Betaproteobacteria;<br>Burkholderiales;Burkholderiaceae;Ralstonia |
| Bacteroidetes;Bacteroidia;Bacteroidales;Bacteroidaceae;Bacteroides*<br>Bacteroidetes;Bacteroidia;Bacteroidales;Porphyromonadaceae;Parabacteroides*<br>Firmicutes;Bacilli;Lactobacillales;Leuconostocaceae;Weissella*<br>Firmicutes;Bacilli;Lactobacillales;Streptococcaceae;Lactococcus*<br>Firmicutes;Clostridia;Clostridiales;Lachnospiraceae;LachnospiraceaeIncertaeSedis*<br>Firmicutes;Clostridia;Clostridiales;Lachnospiraceae;Enterobacteriaceae;Other | Proteobacteria;Betaproteobacteria;<br>Burkholderiales;Burkholderiaceae;Ralstonia |

FIG. 13C

| Subject ID | TumorSample | NormalSample | Tumor Biofilm Status | Normal Biofilm Status | Number Unique Genera in Tumor Sample | Number Shared Genera |
|---|---|---|---|---|---|---|
| 3753 | 3753.Tumor.Right | 3753.Normal.Right | positive | positive | 0 | 6 |
| 3754 | 3754.Tumor.Right | 3754.Normal.Right | positive | positive | 0 | 6 |
| 3756 | 3756.Tumor.Left | 3756.Normal.Left | positive | positive | 4 | 6 |
| 3760 | 3760.Tumor.Left | 3760.Normal.Left | negative | negative | 3 | 21 |

FIG. 13C Cont.

| Number Unique Genera in Normal Flanking | % Tumor seqs in Unique Genera | % Normal flanking seqs in Unique Genera | Unique Genera in Tumor |
|---|---|---|---|
| 0 | 0.00 | 0.00 | |
| 0 | 0.00 | 0.00 | |
| 4 | 35.25 | 12.59 | Firmicutes;Clostridia;Clostridiales;IncertaeSedisXI;Parvimonas*<br>Firmicutes;Clostridia;Clostridiales;Ruminococcaceae;Sporobacter*<br>Firmicutes;Clostridia;Clostridiales;Veillonellaceae;Selenomonas*<br>Fusobacteria;Fusobacteria;Fusobacteriales;Fusobacteriaceae;Fusobacterium |
| 3 | 8.63 | 6.42 | Firmicutes;Bacilli;Bacillales;IncertaeSedisXI;Gemella*<br>Firmicutes;Clostridia;Clostridiales;Lachnospiraceae;Syntrophococcus*<br>Fusobacteria;Fusobacteria;Fusobacteriales;Fusobacteriaceae;Leptotrichia |

FIG. 13C Cont.

| | | | | | |
|---|---|---|---|---|---|
| 3762 | 3762.Tumor.Right | 3762.Normal.Right | positive | positive | 0 | 4 |
| 3763 | 3763.Tumor.Right | 3763.Normal.Right | positive | positive | 0 | 13 |
| 3764 | 3764.Tumor.Right | 3764.Normal.Right | positive | positive | 0 | 12 |

FIG. 13C Cont.

| | | |
|---|---|---|
| | | |
| 0.00 | 0.00 | 0.00 |
| 0.00 | 0.00 | 0.00 |
| 0 | 0 | 0 |

FIG. 13D

| Subject ID | TumorSample | NormalSample | Tumor Biofilm Status | Normal Biofilm Status |
|---|---|---|---|---|
| 3753 | 3753.Tumor.Right | 3753.Normal.Right | positive | positive |
| 3754 | 3754.Tumor.Right | 3754.Normal.Right | positive | positive |
| 3756 | 3756.Tumor.Left | 3756.Normal.Left | positive | positive |
| 3760 | 3760.Tumor.Left | 3760.Normal.Left | negative | negative |

FIG. 13D Cont.

| Shared Genera |
|---|
| Bacteroidetes;Bacteroidetes;Bacteroidales;Bacteroidaceae;Bacteroides*<br>Firmicutes;Clostridia;Clostridiales;Lachnospiraceae;Dorea*<br>Firmicutes;Clostridia;Clostridiales;Lachnospiraceae;LachnospiraceaeIncertaeSedis*<br>Firmicutes;Clostridia;Clostridiales;Lachnospiraceae;Roseburia*<br>Fusobacteria;Fusobacteria;Fusobacteriales;Fusobacteriaceae;Fusobacterium*<br>Proteobacteria;Gammaproteobacteria;Enterobacteriales;Enterobacteriaceae;Other |
| Bacteroidetes;Bacteroidetes;Bacteroidales;Bacteroidaceae;Bacteroides*<br>Bacteroidetes;Bacteroidetes;Bacteroidales;Porphyromonadaceae;Parabacteroides*<br>Bacteroidetes;Bacteroidetes;Bacteroidales;Prevotellaceae;Prevotella*<br>Firmicutes;Clostridia;Clostridiales;Lachnospiraceae;LachnospiraceaeIncertaeSedis*<br>Firmicutes;Clostridia;Clostridiales;Ruminococcaceae;Subdoligranulum*<br>Proteobacteria;Betaproteobacteria;Burkholderiales;Alcaligenaceae;Sutterella |
| Bacteroidetes;Bacteroidetes;Bacteroidales;Bacteroidaceae;Bacteroides*<br>Bacteroidetes;Bacteroidetes;Bacteroidales;Porphyromonadaceae;Parabacteroides*<br>Bacteroidetes;Bacteroidetes;Bacteroidales;Prevotellaceae;Prevotella*<br>Bacteroidetes;Bacteroidetes;Bacteroidales;Rikenellaceae;Alistipes*<br>Firmicutes;Clostridia;Clostridiales;Lachnospiraceae;LachnospiraceaeIncertaeSedis*<br>Proteobacteria;Betaproteobacteria;Burkholderiales;Comamonadaceae;Comamonas |
| Bacteroidetes;Bacteroidetes;Bacteroidales;Bacteroidaceae;Bacteroides*<br>Bacteroidetes;Bacteroidetes;Bacteroidales;Other*<br>Bacteroidetes;Bacteroidetes;Bacteroidales;Porphyromonadaceae;Parabacteroides*<br>Bacteroidetes;Bacteroidetes;Bacteroidales;Porphyromonadaceae;Porphyromonas*<br>Bacteroidetes;Bacteroidetes;Bacteroidales;Prevotellaceae;Prevotella*<br>Bacteroidetes;Bacteroidetes;Bacteroidales;Rikenellaceae;Alistipes*<br>Firmicutes;Bacilli;Lactobacillales;Leuconostocaceae;Weissella*<br>Firmicutes;Clostridia;Clostridiales;IncertaeSedisXI;Parvimonas*<br>Firmicutes;Clostridia;Clostridiales;Lachnospiraceae;LachnospiraceaeIncertaeSedis*<br>Firmicutes;Clostridia;Clostridiales;Lachnospiraceae;Moryella*<br>Firmicutes;Clostridia; Clostridiales;Other*<br>Firmicutes;Clostridia;Clostridiales;Ruminococcaceae;Ethanoligenens*<br>Firmicutes;Clostridia;Clostridiales;Ruminococcaceae;Faecalibacterium*<br>Firmicutes;Clostridia;Clostridiales;Ruminococcaceae;Other*<br>Firmicutes;Clostridia;Clostridiales;Ruminococcaceae;Papillibacter*<br>Firmicutes;Clostridia;Clostridiales;Ruminococcaceae;RuminococcaceaeIncertaeSedis*<br>Firmicutes;Clostridia;Clostridiales;Ruminococcaceae;Sporobacter*<br>Firmicutes;Clostridia;Clostridiales;Ruminococcaceae;Subdoligranulum*<br>Fusobacteria;Fusobacteria;Fusobacteriales;Fusobacteriaceae;Fusobacterium*<br>Other* Proteobacteria;Betaproteobacteria;Burkholderiales;Burkholderiaceae;Ralstonia |

FIG. 13D Cont.

| Unique Genera in Normal Flanking |
|---|
| |
| |
| Firmicutes;Bacilli;Lactobacillales;Streptococcaceae;Lactococcus*<br>Proteobacteria;Alphaproteobacteria;Sphingomonadales;Sphingomonadaceae;Sphingomonas*<br>Proteobacteria;Betaproteobacteria;Burkholderiales;Comamonadaceae;Delftia*<br>Proteobacteria;Gammaproteobacteria;Enterobacteriales;Enterobacteriaceae;Other |
| Firmicutes;Bacilli;Lactobacillales;Streptococcaceae;Lactococcus*<br>Firmicutes;Clostridia;Clostridiales;Ruminococcaceae;Ruminococcus*<br>Proteobacteria;Betaproteobacteria;Burkholderiales;Comamonadaceae;Delftia |

FIG. 13D Cont.

| 3762 | 3762.Tumor.Right | 3762.Normal.Right | positive | positive |
| --- | --- | --- | --- | --- |
| 3763 | 3763.Tumor.Right | 3763.Normal.Right | positive | positive |
| 3764 | 3764.Tumor.Right | 3764.Normal.Right | positive | positive |

FIG. 13D Cont.

| |
|---|
| Bacteroidetes;Bacteroidetes;Bacteroidales;Bacteroidaceae;Bacteroides*<br>Firmicutes;Clostridia;Clostridiales;Lachnospiraceae;Dorea*<br>Firmicutes;Clostridia;Clostridiales;Lachnospiraceae;LachnospiraceaeIncertaeSedis*<br>Proteobacteria;Gammaproteobacteria;Enterobacteriales;Enterobacteriaceae;Other |
| Bacteroidetes;Bacteroidetes;Bacteroidales;Bacteroidaceae;Bacteroides*<br>Bacteroidetes;Bacteroidetes;Bacteroidales;Porphyromonadaceae;Parabacteroides*<br>Bacteroidetes;Bacteroidetes;Bacteroidales;Prevotellaceae;Prevotella*<br>Firmicutes;Clostridia;Clostridiales;Lachnospiraceae;LachnospiraceaeIncertaeSedis*<br>Firmicutes;Clostridia;Clostridiales;Lachnospiraceae;Roseburia*<br>Firmicutes;Clostridia;Clostridiales;Ruminococcaceae;Faecalibacterium*<br>Firmicutes;Clostridia;Clostridiales;Ruminococcaceae;Sporobacter*<br>Firmicutes;Clostridia;Clostridiales;Ruminococcaceae;Subdoligranulum*<br>Firmicutes;Clostridia;Clostridiales;Veillonellaceae;Acidaminococcus*<br>Firmicutes;Clostridia;Clostridiales;Veillonellaceae;Megasphaera*<br>Firmicutes;Clostridia;Clostridiales;Veillonellaceae;Selenomonas*<br>Fusobacteria;Fusobacteria;Fusobacteriales;Fusobacteriaceae;Fusobacterium* |
| Proteobacteria;Betaproteobacteria;Burkholderiales;Alcaligenaceae;Sutterella<br>Bacteroidetes;Bacteroidetes;Bacteroidales;Bacteroidaceae;Bacteroides*<br>Bacteroidetes;Bacteroidetes;Bacteroidales;Porphyromonadaceae;Parabacteroides*<br>Bacteroidetes;Bacteroidetes;Bacteroidales;Rikenellaceae;Alistipes*<br>Firmicutes;Clostridia;Clostridiales;Lachnospiraceae;LachnospiraceaeIncertaeSedis*<br>Firmicutes;Clostridia;Clostridiales;Lachnospiraceae;Other*<br>Firmicutes;Clostridia;Clostridiales;Lachnospiraceae;Roseburia*<br>Firmicutes;Clostridia;Clostridiales;Other*<br>Firmicutes;Clostridia;Clostridiales;Ruminococcaceae;Faecalibacterium*<br>Firmicutes;Clostridia;Clostridiales;Ruminococcaceae;Subdoligranulum*<br>Firmicutes;Clostridia;Clostridiales;Veillonellaceae;Acidaminococcus*<br>Other*   Proteobacteria;Alphaproteobacteria;Rickettsiales;Anaplasmataceae;Other |

FIG. 13E

| Subject ID | TumorSample | NormalSample | Tumor Biofilm Status | Normal Biofilm Status | Number Unique Genera in Tumor Sample | Number Shared Genera |
|---|---|---|---|---|---|---|
| 3766 | 3766.Tumor.Left | 3766.Normal.Left | negative | negative | 2 | 4 |
| 3769 | 3769.Tumor.Left | 3769.Normal.Left | negative | negative | 0 | 10 |
| 3770 | 3770.Tumor.Right | 3770.Normal.Right | negative | negative | 2 | 6 |
| 3774 | 3774.Tumor.Right | 3774.Normal.Right | positive | positive | 1 | 6 |
| 3776 | 3776.Polyp.Right | 3776.Normal.Right | positive | positive | 0 | 9 |

FIG. 13E Cont

| Number Unique Genera in Normal Flanking | % Tumor seqs in Unique Genera | % Normal flanking seqs in Unique Genera | Unique Genera in Tumor |
|---|---|---|---|
| 1 | 84.28 | 58.64 | Firmicutes;Clostridia;Clostridiales;IncertaeSedisXI;Parvimonas*Fusobacteria;Fusobacteria;Fusobacteriales;Fusobacteriaceae;Fusobacterium |
| 0 | 0.00 | 0.00 | |
| 0 | 67.41 | 0.00 | Firmicutes;Clostridia;Clostridiales;Veillonellaceae;Selenomonas*Fusobacteria;Fusobacteria;Fusobacteriales;Fusobacteriaceae;Fusobacterium |
| 0 | 30.92 | 0.00 | Fusobacteria;Fusobacteria;Fusobacteriales;Fusobacteriaceae;Fusobacterium |
| 0 | 0.00 | 0.00 | |

FIG. 13E Cont

| | | | | | |
|---|---|---|---|---|---|
| 3785 | 3785.Tumor.Left | 3785.Normal.Left | negative | negative | 2 | 11 |
| 3789 | 3789.Tumor.Left | 3789.Normal.Left | negative | negative | 0 | 13 |
| 3972 | 3972.Tumor.Right | 3972.Normal.Right | positive | positive | 0 | 13 |

FIG. 13E Cont

| | | Firmicutes;Clostridia;Clostridiales;Lachnospiraceae;Dorea* Fusobacteria;Fusobacteria;Fusobacteriales;Fusobacteriaceae; Fusobacterium |
|---|---|---|
| 0 | 8.63 | 0.00 |
| 1 | 0.00 | 1.21 |
| 0 | 0.00 | 0.00 |

FIG. 13F

| Subject ID | TumorSample | NormalSample | Tumor Biofilm Status | Normal Biofilm Status |
|---|---|---|---|---|
| 3766 | 3766.Tumor.Left | 3766.Normal.Left | negative | negative |
| 3769 | 3769.Tumor.Left | 3769.Normal.Left | negative | negative |
| 3770 | 3770.Tumor.Right | 3770.Normal.Right | negative | negative |
| 3774 | 3774.Tumor.Right | 3774.Normal.Right | positive | positive |
| 3776 | 3776.Polyp.Right | 3776.Normal.Right | positive | positive |

FIG. 13F Cont

| Shared Genera | Unique Genera in Normal Flanking |
|---|---|
| Bacteroidetes;Bacteroidales;Bacteroidaceae;Bacteroides* Other* Proteobacteria;Alphaproteobacteria;Sphingomonadales;Sphingomonadaceae; Sphingomonas* | |
| Proteobacteria;Betaproteobacteria;Burkholderiales;Comamonadaceae;Comamonas Bacteroidetes;Bacteroidales;Bacteroidaceae;Bacteroides* | Proteobacteria;Betaproteobacteria; Burkholderiales;Burkholderiaceae; Ralstonia |
| Bacteroidetes;Bacteroidales;Porphyromonadaceae;Parabacteroides* Bacteroidetes;Bacteroidales;Rikenellaceae;Alistipes* Firmicutes;Clostridia;Clostridiales;Lachnospiraceae;LachnospiraceaeIncertaeSedis* Clostridiales;Other* Firmicutes;Clostridia;Clostridiales;Clostridia;Clostridiales;Other* Firmicutes;Clostridia;Clostridiales;Ruminococcaceae;Faecalibacterium* Firmicutes;Clostridia;Clostridiales;Ruminococcaceae;Other* Firmicutes;Clostridia;Clostridiales;Ruminococcaceae;RuminococcaceaeIncertaeSedis* Firmicutes;Clostridia;Clostridiales;Ruminococcaceae;Sporobacter | |
| Bacteroidetes;Bacteroidales;Bacteroidaceae;Bacteroides* Bacteroidetes;Bacteroidales;Porphyromonadaceae;Parabacteroides* Bacteroidetes;Bacteroidales;Rikenellaceae;Alistipes* Firmicutes;Clostridia;Clostridiales;Lachnospiraceae;LachnospiraceaeIncertaeSedis* Firmicutes;Clostridia;Clostridiales;Lachnospiraceae;Roseburia* Firmicutes;Clostridia;Clostridiales;Ruminococcaceae;Faecalibacterium | |
| Bacteroidetes;Bacteroidales;Bacteroidaceae;Bacteroides* Bacteroidetes;Bacteroidales;Porphyromonadaceae;Parabacteroides* Bacteroidetes;Bacteroidales;Rikenellaceae;Alistipes* Firmicutes;Clostridia;Clostridiales;Lachnospiraceae;LachnospiraceaeIncertaeSedis* Firmicutes;Clostridia;Clostridiales;Ruminococcaceae;Faecalibacterium* Firmicutes;Clostridia;Clostridiales;Ruminococcaceae;Subdoligranulum | |
| Bacteroidetes;Bacteroidales;Bacteroidaceae;Bacteroides* Bacteroidetes;Bacteroidales;Porphyromonadaceae;Parabacteroides* Bacteroidetes;Bacteroidales;Rikenellaceae;Alistipes* Firmicutes;Clostridia;Clostridiales;Lachnospiraceae;LachnospiraceaeIncertaeSedis* Firmicutes;Clostridia;Clostridiales;Lachnospiraceae;Other* Firmicutes;Clostridia;Clostridiales;Ruminococcaceae;Faecalibacterium* Firmicutes;Clostridia;Clostridiales;Ruminococcaceae;Sporobacter* Firmicutes;Clostridia;Clostridiales;Ruminococcaceae;Subdoligranulum* Proteobacteria;Gammaproteobacteria;Enterobacteriales;Enterobacteriaceae;_Other | |

FIG. 13F Cont

| | | | |
|---|---|---|---|
| 3785 | 3785.Tumor.Left | 3785.Normal.Left | negative | negative |
| 3789 | 3789.Tumor.Left | 3789.Normal.Left | negative | negative |
| 3972 | 3972.Tumor.Right | 3972.Normal.Right | positive | positive |

FIG. 13F Cont

| Taxonomy | | |
|---|---|---|
| Bacteroidetes;Bacteroidetes;Bacteroidales;Bacteroidaceae;Bacteroides* | | |
| Bacteroidetes;Bacteroidetes;Bacteroidales;Rikenellaceae;Alistipes* | | |
| Firmicutes;Bacilli;Lactobacillales;Streptococcaceae;Lactococcus* | | |
| Firmicutes;Clostridia;Clostridiales;Lachnospiraceae;LachnospiraceaeIncertaeSedis* | | |
| Firmicutes;Clostridia;Clostridiales;Ruminococcaceae;Faecalibacterium* | | |
| Firmicutes;Clostridia;Clostridiales;Ruminococcaceae;RuminococcaceaeIncertaeSedis* | | |
| Proteobacteria;Alphaproteobacteria;Sphingomonadales;Sphingomonadaceae;Sphingomonas* | | |
| Proteobacteria;Betaproteobacteria;Burkholderiales;Alcaligenaceae;Sutterella* | | |
| Proteobacteria;Betaproteobacteria;Burkholderiales;Burkholderiales;Comamonadaceae;Comamonas* | | |
| Proteobacteria;Betaproteobacteria;Burkholderiales;Comamonadaceae;Delftia* | | |
| Proteobacteria;Betaproteobacteria;Burkholderiales;Comamonadaceae;Other | | |
| Bacteroidetes;Bacteroidetes;Bacteroidales;Bacteroidaceae;Bacteroides* | | |
| Bacteroidetes;Bacteroidetes;Bacteroidales;Porphyromonadaceae;Parabacteroides* | | |
| Bacteroidetes;Bacteroidetes;Bacteroidales;Prevotellaceae;Prevotella* | | |
| Firmicutes;Clostridia;Clostridiales;Lachnospiraceae;Anaerostipes* | | |
| Firmicutes;Clostridia;Clostridiales;Lachnospiraceae;LachnospiraceaeIncertaeSedis* | | |
| Firmicutes;Clostridia;Clostridiales;Lachnospiraceae;Other* Firmicutes;Clostridia;Clostridiales;Other* | | |
| Firmicutes;Clostridia;Clostridiales;Ruminococcaceae;Faecalibacterium* | | |
| Firmicutes;Clostridia;Clostridiales;Ruminococcaceae;Ruminococcus* | | |
| Firmicutes;Clostridia;Clostridiales;Ruminococcaceae;Sporobacter* | | |
| Firmicutes;Clostridia;Clostridiales;Ruminococcaceae;Subdoligranulum* | | |
| Fusobacteria;Fusobacteria;Fusobacteriales;Fusobacteriaceae;Fusobacterium* | | |
| Proteobacteria;Betaproteobacteria;Burkholderiales;Comamonadaceae;Comamonas | | |
| Bacteroidetes;Bacteroidetes;Bacteroidales;Bacteroidaceae;Bacteroides* | Proteobacteria;Alphaproteobacteria;Sphingomonadales;Sphingomonadaceae;Sphingomonas | |
| Bacteroidetes;Bacteroidetes;Bacteroidales;Porphyromonadaceae;Parabacteroides* | | |
| Bacteroidetes;Bacteroidetes;Bacteroidales;Rikenellaceae;Alistipes* | | |
| Firmicutes;Bacilli;Lactobacillales;Streptococcaceae;Lactococcus* | | |
| Firmicutes;Clostridia;Clostridiales;Lachnospiraceae;LachnospiraceaeIncertaeSedis* | | |
| Firmicutes;Clostridia;Clostridiales;Lachnospiraceae;Roseburia* | | |
| Firmicutes;Clostridia;Clostridiales;Ruminococcaceae;Faecalibacterium* | | |
| Firmicutes;Clostridia;Clostridiales;Ruminococcaceae;Sporobacter* Other* | | |
| Proteobacteria;Betaproteobacteria;Burkholderiales;Comamonadaceae;Comamonas* | | |
| Proteobacteria;Betaproteobacteria;Burkholderiales;Comamonadaceae;Delftia* | | |
| Proteobacteria;Betaproteobacteria;Burkholderiales;Comamonadaceae;Other* | | |
| Proteobacteria;Gammaproteobacteria;Enterobacteriales;Enterobacteriaceae;Other | | |

FIG. 13G

| Subject ID | TumorSample | NormalSample | Tumor Biofilm Status | Normal Biofilm Status | Number Unique Genera in Tumor Sample | Number Shared Genera |
|---|---|---|---|---|---|---|
| 3976 | 3976.Tumor.Left | 3976.Normal.Left | negative | negative | 0 | 7 |
| 3977 | 3977.Tumor.Left | 3977.Normal.Left | negative | negative | 2 | 13 |
| 3979 | 3979.Tumor.Right | 3979.Normal.Right | positive | positive | 1 | 8 |
| 3982 | 3982.Tumor.Right | 3982.Normal.Right | positive | positive | 0 | 12 |

FIG. 13G Cont

| Number Unique Genera in Normal Flanking | % Tumor seqs in Unique Genera | % Normal flanking seqs in Unique Genera | Unique Genera in Tumor |
|---|---|---|---|
| 0 | 0.00 | 0.00 | |
| 0 | 22.05 | 0.00 | Firmicutes;Bacilli;Bacillales;Bacillaceae;Bacillaceae 1; Fusobacteria;Fusobacteria;Fusobacteriales; Fusobacteriaceae;Fusobacterium |
| 0 | 15.01 | 0.00 | Proteobacteria;Gammaproteobacteria; Enterobacteriales;Enterobacteriaceae;Other |
| 0 | 0.00 | 0.00 | |

FIG. 13H

| Subject ID | TumorSample | NormalSample | Tumor Biofilm Status | Normal Biofilm Status |
|---|---|---|---|---|
| 3976 | 3976.Tumor.Left | 3976.Normal.Left | negative | negative |
| 3977 | 3977.Tumor.Left | 3977.Normal.Left | negative | negative |
| 3979 | 3979.Tumor.Right | 3979.Normal.Right | positive | positive |
| 3982 | 3982.Tumor.Right | 3982.Normal.Right | positive | positive |

FIG. 13H Cont

| Shared Genera | Unique Genera in Normal Flanking |
|---|---|
| Bacteroidetes;Bacteroidetes;Bacteroidales;Bacteroidaceae;Bacteroides*<br>Bacteroidetes;Bacteroidetes;Bacteroidales;Porphyromonadaceae;Parabacteroides*<br>Bacteroidetes;Bacteroidetes;Bacteroidales;Prevotellaceae;Prevotella*<br>Firmicutes;Clostridia;Clostridiales;Lachnospiraceae;LachnospiraceaeIncertaeSedis*<br>Firmicutes;Clostridia;Clostridiales;Ruminococcaceae;Faecalibacterium*<br>Firmicutes;Clostridia;Clostridiales;Ruminococcaceae;Subdoligranulum*<br>Fusobacteria;Fusobacteria;Fusobacteriales;Fusobacteriaceae;Fusobacterium | |
| Bacteroidetes;Bacteroidetes;Bacteroidales;Bacteroidaceae;Bacteroides*<br>Bacteroidetes;Bacteroidetes;Bacteroidales;Rikenellaceae;Alistipes*<br>Firmicutes;Bacilli;Lactobacillales;Streptococcaceae;Lactococcus*<br>Firmicutes;Clostridia;Clostridiales;Lachnospiraceae;LachnospiraceaeIncertaeSedis*<br>Firmicutes;Clostridia;Clostridiales;Ruminococcaceae;Faecalibacterium*<br>Firmicutes;Clostridia;Clostridiales;Ruminococcaceae;Subdoligranulum* Other*<br>Proteobacteria;Alphaproteobacteria;Other*<br>Proteobacteria;Betaproteobacteria;Burkholderiales;Alcaligenaceae;Sutterella*<br>Proteobacteria;Betaproteobacteria;Burkholderiales;Comamonadaceae;Comamonas*<br>Proteobacteria;Betaproteobacteria;Burkholderiales;Comamonadaceae;Delftia*<br>Proteobacteria;Betaproteobacteria;Burkholderiales;Comamonadaceae;Other*<br>Proteobacteria;Gammaproteobacteria;Enterobacteriales;Enterobacteriaceae;Other | |
| Bacteroidetes;Bacteroidetes;Bacteroidales;Bacteroidaceae;Bacteroides*<br>Bacteroidetes;Bacteroidetes;Bacteroidales;Prevotellaceae;Prevotella*<br>Bacteroidetes;Bacteroidetes;Bacteroidales;Prevotellaceae;Xylanibacter*<br>Firmicutes;Clostridia;Clostridiales;Lachnospiraceae;LachnospiraceaeIncertaeSedis*<br>Firmicutes;Clostridia;Clostridiales;Ruminococcaceae;Faecalibacterium*<br>Firmicutes;Clostridia;Clostridiales;Ruminococcaceae;Subdoligranulum*<br>Firmicutes;Clostridia;Clostridiales;Veillonellaceae;Acidaminococcus*<br>Proteobacteria;Betaproteobacteria;Burkholderiales;Alcaligenaceae;Sutterella | |
| Bacteroidetes;Bacteroidetes;Bacteroidales;Bacteroidaceae;Bacteroides*<br>Bacteroidetes;Bacteroidetes;Bacteroidales;Porphyromonadaceae;Parabacteroides*<br>Bacteroidetes;Bacteroidetes;Bacteroidales;Porphyromonadaceae;Tannerella*<br>Bacteroidetes;Bacteroidetes;Bacteroidales;Rikenellaceae;Alistipes*<br>Firmicutes;Clostridia;Clostridiales;Lachnospiraceae;Dorea*<br>Firmicutes;Clostridia;Clostridiales;Lachnospiraceae;LachnospiraceaeIncertaeSedis*<br>Firmicutes;Clostridia;Clostridiales;Lachnospiraceae;Other*<br>Firmicutes;Clostridia;Clostridiales;Lachnospiraceae;Roseburia*<br>Firmicutes;Clostridia;Clostridiales;Ruminococcaceae;Faecalibacterium*<br>Firmicutes;Clostridia;Clostridiales;Ruminococcaceae;Sporobacter*<br>Firmicutes;Clostridia;Clostridiales;Ruminococcaceae;Subdoligranulum*<br>Proteobacteria;Gammaproteobacteria;Enterobacteriales;Enterobacteriaceae;Other | |

FIG. 14A

Taxonomic distributions of CRC, adenoma and their paired surgically-resected distal normal samples, and colonoscopy biopsies.

| (a) Phylum level assignments | | | |
|---|---|---|---|
| Patient ID | 3726 | 3726 | 3728 |
| Status | Normal | Polyp | Normal |
| Location | Right | Right | Right |
| Status_Location | Normal_Right | Polyp_Right | Normal_Right |
| Biofilm | positive | positive | NA |
| SampleName | 3726.Norma | 3726.Polyp.R | 3728.Norma |
| Bacteria_Acidobacteria | 0 | 0 | 0 |
| Bacteria_Actinobacteria | 1 | 15 | 3 |
| Bacteria_Bacteroidetes | 8322 | 8675 | 5249 |
| Bacteria_Cyanobacteria | 0 | 0 | 0 |
| Bacteria_Deferribacteres | 0 | 0 | 0 |
| Bacteria_Firmicutes | 1163 | 1671 | 1329 |
| Bacteria_Fusobacteria | 0 | 0 | 17 |
| Bacteria_Gemmatimonadetes | 0 | 0 | 0 |
| Bacteria_OP11 | 0 | 0 | 0 |
| Bacteria_Other | 14 | 22 | 14 |
| Bacteria_Proteobacteria | 15 | 223 | 124 |
| Bacteria_TM7 | 0 | 0 | 0 |
| Bacteria_Tenericutes | 0 | 0 | 0 |
| Bacteria_Verrucomicrobia | 0 | 0 | 1 |
| Root_Other | 0 | 0 | 1 |

FIG. 14A Cont.

| 3728 | 3731 | 3731 | 3735 | 3735 | 3749 | 3749 | 3752 |
|---|---|---|---|---|---|---|---|
| Tumor | Normal | Tumor | Normal | Tumor | Normal | Tumor | Normal |
| Right | Right | Right | Left | Left | Left | Left | Left |
| Tumor_Right | Normal_Right | Tumor_Right | Normal_Left | Tumor_Left | Normal_Left | Tumor_Left | Normal_Left |
| positive | positive | positive | negative | negative | negative | negative | negative |
| 3728.Tumor. | 3731.Norma | 3731.Tumor. | 3735.Norma | 3735.Tumor. | 3749.Norma | 3749.Tumor.| 3752.Norma |
| 0 | 0 | 0 | 0 | 0 | 0 | 0 | 0 |
| 39 | 1 | 7 | 1 | 18 | 0 | 1 | 4 |
| 3520 | 3 | 7 | 5456 | 6565 | 2856 | 2419 | 3281 |
| 0 | 0 | 0 | 0 | 0 | 0 | 0 | 2 |
| 0 | 0 | 0 | 0 | 0 | 0 | 0 | 0 |
| 1069 | 9283 | 1668 | 1612 | 4500 | 3233 | 1129 | 1030 |
| 12567 | 0 | 0 | 0 | 334 | 1 | 978 | 0 |
| 0 | 0 | 0 | 0 | 0 | 0 | 0 | 0 |
| 0 | 0 | 0 | 0 | 0 | 0 | 0 | 0 |
| 69 | 11 | 33 | 5 | 66 | 8 | 7 | 12 |
| 24 | 194 | 5883 | 235 | 856 | 834 | 12308 | 837 |
| 0 | 0 | 0 | 0 | 0 | 0 | 0 | 0 |
| 0 | 0 | 0 | 0 | 0 | 0 | 0 | 0 |
| 0 | 0 | 0 | 0 | 4 | 0 | 0 | 0 |
| 0 | 0 | 0 | 0 | 1 | 1 | 0 | 10 |

FIG. 14B

Taxonomic distributions of CRC, adenoma and their paired surgically-resected distal normal samples, and colonoscopy biopsies.

(a) Phylum level assignments

| Patient ID | 3752 | 3753 | 3753 | 3754 |
|---|---|---|---|---|
| Status | Tumor | Normal | Tumor | Normal |
| Location | Left | Right | Right | Right |
| Status_Location | Tumor_Left | Normal_Righ | Tumor_Righ | Normal_Righ |
| Biofilm | negative | positive | positive | positive |
| SampleName | 3752.Tumor. | 3753.Normal. | 3753.Tumor. | 3754.Normal. |
| Bacteria_Acidobacteria | 0 | 0 | 0 | 0 |
| Bacteria_Actinobacteria | 23 | 24 | 27 | 0 |
| Bacteria_Bacteroidetes | 13580 | 21661 | 24700 | 13109 |
| Bacteria_Cyanobacteria | 0 | 0 | 0 | 0 |
| Bacteria_Deferribacteres | 0 | 0 | 0 | 0 |
| Bacteria_Firmicutes | 1503 | 8767 | 11111 | 3716 |
| Bacteria_Fusobacteria | 0 | 99 | 491 | 1 |
| Bacteria_Gemmatimonadetes | 0 | 0 | 0 | 0 |
| Bacteria_OP11 | 0 | 0 | 0 | 0 |
| Bacteria_Other | 1 | 7 | 7 | 1 |
| Bacteria_Proteobacteria | 1793 | 332 | 124 | 689 |
| Bacteria_TM7 | 0 | 0 | 0 | 0 |
| Bacteria_Tenericutes | 0 | 0 | 0 | 0 |
| Bacteria_Verrucomicrobia | 0 | 0 | 0 | 0 |
| Root_Other | 0 | 0 | 0 | 0 |

FIG. 14B Cont.

| | 3754 | 3756 | 3756 | 3760 | 3760 | 3762 | 3762 |
|---|---|---|---|---|---|---|---|
| | Tumor Right | Normal Left | Tumor Left | Normal Left | Tumor Left | Normal Right | Tumor Right |
| | positive | positive | positive | negative | negative | positive | positive |
| | 3754.Tumor_Right positive | 3756.Normal_Left positive | 3756.Tumor_Left positive | 3760.Normal_Left negative | 3760.Tumor_Left negative | 3762.Normal_Right positive | 3762.Tumor_Right positive |
| | 0 | 0 | 0 | 0 | 0 | 0 | 0 |
| | 4 | 26 | 5 | 7 | 74 | 2 | 3 |
| | 23616 | 3176 | 6330 | 1910 | 1901 | 10142 | 9575 |
| | 0 | 0 | 0 | 0 | 0 | 0 | 0 |
| | 0 | 0 | 0 | 0 | 0 | 0 | 0 |
| | 9506 | 574 | 2289 | 4677 | 2335 | 2116 | 764 |
| | 0 | 0 | 2745 | 33 | 11842 | 1 | 0 |
| | 0 | 0 | 0 | 1 | 0 | 0 | 0 |
| | 0 | 0 | 0 | 0 | 0 | 0 | 0 |
| | 0 | 34 | 23 | 75 | 17 | 0 | 1 |
| | 1725 | 4748 | 48 | 372 | 19 | 271 | 51 |
| | 0 | 0 | 0 | 0 | 0 | 0 | 0 |
| | 0 | 0 | 0 | 0 | 0 | 0 | 0 |
| | 0 | 0 | 0 | 0 | 0 | 0 | 0 |
| | 0 | 0 | 0 | 0 | 1 | 0 | 0 |

FIG. 14C

Taxonomic distributions of CRC, adenoma and their paired surgically-resected distal normal samples, and colonoscopy biopsies.

(a) Phylum level assignments

| Patient ID | 3763 | 3763 | 3764 | 3764 |
|---|---|---|---|---|
| Status | Normal | Tumor | Normal | Tumor |
| Location | Right | Right | Right | Right |
| Status_Location | Normal_Right | Tumor_Right | Normal_Right | Tumor_Right |
| Biofilm | positive | positive | positive | positive |
| SampleName | 3763.Norma | 3763.Tumor. | 3764.Norma | 3764.Tumor. |
| Bacteria_Acidobacteria | 0 | 0 | 0 | 0 |
| Bacteria_Actinobacteria | 46 | 18 | 0 | 3 |
| Bacteria_Bacteroidetes | 10005 | 6381 | 4519 | 6385 |
| Bacteria_Cyanobacteria | 0 | 0 | 0 | 0 |
| Bacteria_Deferribacteres | 0 | 0 | 0 | 0 |
| Bacteria_Firmicutes | 8389 | 3362 | 1950 | 2968 |
| Bacteria_Fusobacteria | 471 | 4848 | 0 | 9 |
| Bacteria_Gemmatimonadetes | 0 | 0 | 0 | 0 |
| Bacteria_OP11 | 0 | 0 | 0 | 0 |
| Bacteria_Other | 5 | 23 | 159 | 156 |
| Bacteria_Proteobacteria | 409 | 297 | 150 | 149 |
| Bacteria_TM7 | 0 | 0 | 0 | 0 |
| Bacteria_Tenericutes | 0 | 0 | 0 | 0 |
| Bacteria_Verrucomicrobia | 0 | 0 | 0 | 0 |
| Root_Other | 0 | 0 | 0 | 0 |

FIG.14C Cont.

| 3766 | 3766 | 3769 | 3769 | 3770 | 3770 | 3774 |
|---|---|---|---|---|---|---|
| Normal | Tumor | Normal | Tumor | Normal | Tumor | Normal |
| Left | Left | Left | Left | Right | Right | Right |
| Normal_Left | Tumor_Left | Normal_Left | Tumor_Left | Normal_Right | Tumor_Right | Normal_Right |
| negative | negative | negative | negative | negative | negative | positive |
| 3766.Normal | 3766.Tumor. | 3769.Norma | 3769.Tumor. | 3770.Norma | 3770.Tumor. | 3774.Normal |
| 0 | 0 | 0 | 0 | 0 | 0 | 0 |
| 5 | 0 | 1 | 2 | 1 | 2 | 1 |
| 3159 | 661 | 5841 | 4794 | 9118 | 2697 | 12290 |
| 0 | 0 | 0 | 0 | 0 | 0 | 0 |
| 0 | 0 | 0 | 0 | 0 | 0 | 0 |
| 305 | 1157 | 3400 | 3162 | 1196 | 998 | 1256 |
| 2 | 6602 | 1 | 41 | 0 | 5480 | 0 |
| 0 | 0 | 0 | 0 | 0 | 0 | 0 |
| 362 | 45 | 4 | 10 | 9 | 24 | 1 |
| 7180 | 900 | 10 | 107 | 38 | 4 | 30 |
| 0 | 0 | 0 | 0 | 0 | 0 | 0 |
| 0 | 0 | 0 | 0 | 0 | 0 | 0 |
| 0 | 0 | 0 | 1 | 0 | 0 | 0 |
| 0 | 0 | 0 | 0 | 0 | 0 | 0 |

FIG. 14D

Taxonomic distributions of CRC, adenoma and their paired surgically-resected distal normal samples, and colonoscopy biopsies.

| (a) Phylum level assignments | | | | |
|---|---|---|---|---|
| Patient ID | 3774 | 3776 | 3776 | 3785 |
| Status | Tumor | Normal | Polyp | Normal |
| Location | Right | Right | Right | Left |
| Status_Location | Tumor_Right | Normal_Right | Polyp_Right | Normal_Left |
| Biofilm | positive | positive | positive | negative |
| SampleName | 3774.Tumor. | 3776.Normal | 3776.Polyp.R | 3785.Norma |
| Bacteria_Acidobacteria | 0 | 0 | 0 | 0 |
| Bacteria_Actinobacteria | 0 | 0 | 0 | 15 |
| Bacteria_Bacteroidetes | 5697 | 5239 | 3128 | 3021 |
| Bacteria_Cyanobacteria | 0 | 0 | 0 | 0 |
| Bacteria_Deferribacteres | 0 | 0 | 0 | 0 |
| Bacteria_Firmicutes | 896 | 723 | 1883 | 310 |
| Bacteria_Fusobacteria | 2775 | 1 | 5 | 0 |
| Bacteria_Gemmatimonadetes | 0 | 0 | 0 | 0 |
| Bacteria_OP11 | 0 | 0 | 0 | 0 |
| Bacteria_Other | 17 | 1 | 5 | 34 |
| Bacteria_Proteobacteria | 36 | 4124 | 1777 | 6558 |
| Bacteria_TM7 | 0 | 0 | 0 | 0 |
| Bacteria_Tenericutes | 0 | 0 | 0 | 0 |
| Bacteria_Verrucomicrobia | 0 | 0 | 0 | 0 |
| Root_Other | 0 | 0 | 0 | 0 |

FIG. 14D Cont.

| | 3785 | 3789 | 3789 | 3972 | 3972 | 3976 | 3976 |
|---|---|---|---|---|---|---|---|
| | Tumor | Normal | Tumor | Normal | Tumor | Normal | Tumor |
| | Left | Left | Left | Right | Right | Left | Left |
| | Tumor_Left | Normal_Left | Tumor_Left | Normal_Right | Tumor_Right | Normal_Left | Tumor_Left |
| | negative | negative | negative | positive | positive | negative | negative |
| | 3785.Tumor. | 3789.Norma | 3789.Tumor. | 3972.Norma | 3972.Tumor. | 3976.Norma | 3976.Tumor. |
| | 0 | 0 | 0 | 0 | 0 | 0 | 0 |
| | 7 | 4 | 2 | 2 | 14 | 1 | 0 |
| | 4921 | 2791 | 1775 | 4720 | 1248 | 8046 | 3332 |
| | 0 | 0 | 0 | 0 | 0 | 0 | 0 |
| | 0 | 0 | 0 | 0 | 0 | 0 | 0 |
| | 1552 | 1611 | 1990 | 1907 | 1113 | 1921 | 329 |
| | 531 | 10 | 3141 | 0 | 0 | 23 | 7329 |
| | 0 | 0 | 0 | 0 | 0 | 0 | 0 |
| | 0 | 0 | 0 | 0 | 0 | 0 | 0 |
| | 57 | 3 | 21 | 17 | 208 | 1 | 4 |
| | 854 | 1576 | 65 | 381 | 5914 | 17 | 27 |
| | 0 | 0 | 0 | 0 | 0 | 0 | 0 |
| | 0 | 0 | 0 | 0 | 0 | 0 | 0 |
| | 0 | 0 | 0 | 0 | 0 | 0 | 0 |
| | 1 | 0 | 0 | 1 | 3 | 0 | 0 |

FIG. 14E

Taxonomic distributions of CRC, adenoma and their paired surgically-resected distal normal samples, and colonoscopy biopsies.

(a) Phylum level assignments

| Patient ID | 3977 | 3977 | 3979 | 3979 |
|---|---|---|---|---|
| Status | Normal | Tumor | Normal | Tumor |
| Location | Left | Left | Right | Right |
| Status_Location | Normal_Left | Tumor_Left | Normal_Right | Tumor_Right |
| Biofilm | negative | negative | positive | positive |
| SampleName | 3977.Normal | 3977.Tumor. | 3979.Normal | 3979.Tumor. |
| Bacteria_Acidobacteria | 0 | 0 | 0 | 0 |
| Bacteria_Actinobacteria | 4 | 0 | 1 | 1 |
| Bacteria_Bacteroidetes | 2547 | 2481 | 10371 | 5877 |
| Bacteria_Cyanobacteria | 0 | 0 | 0 | 0 |
| Bacteria_Deferribacteres | 0 | 0 | 0 | 0 |
| Bacteria_Firmicutes | 1530 | 787 | 1094 | 1869 |
| Bacteria_Fusobacteria | 3 | 1461 | 1 | 0 |
| Bacteria_Gemmatimonadetes | 0 | 0 | 0 | 0 |
| Bacteria_OP11 | 1 | 1 | 0 | 0 |
| Bacteria_Other | 36 | 332 | 6 | 58 |
| Bacteria_Proteobacteria | 5285 | 2720 | 32 | 1392 |
| Bacteria_TM7 | 0 | 0 | 0 | 0 |
| Bacteria_Tenericutes | 0 | 0 | 9 | 6 |
| Bacteria_Verrucomicrobia | 0 | 0 | 0 | 0 |
| Root_Other | 1 | 16 | 0 | 0 |

FIG. 14E Cont.

| 3982 Normal Right | 3982 Tumor Right | S10 Biopsy Left | S10 Biopsy Right | S11 Biopsy Left | S11 Biopsy Right | S12 Biopsy Left |
|---|---|---|---|---|---|---|
| positive | positive | negative | negative | negative | negative | negative |
| 3982.Normal.R | 3982.Tumor.R | S10.Biopsy.L | S10.Biopsy.R | S11.Biopsy.L | S11.Biopsy.R | S12.Biopsy.L |
| 0 | 0 | 0 | 0 | 0 | 0 | 0 |
| 3 | 3 | 0 | 0 | 0 | 0 | 0 |
| 12654 | 11598 | 686 | 3018 | 1343 | 2053 | 1170 |
| 0 | 0 | 1 | 0 | 0 | 0 | 0 |
| 0 | 0 | 0 | 0 | 0 | 0 | 0 |
| 3583 | 7012 | 441 | 281 | 429 | 496 | 1180 |
| 0 | 14 | 28 | 287 | 0 | 1 | 0 |
| 0 | 0 | 0 | 0 | 0 | 0 | 0 |
| 3 | 5 | 2 | 1 | 2 | 1 | 1 |
| 345 | 158 | 2772 | 103 | 52 | 153 | 154 |
| 0 | 0 | 0 | 0 | 0 | 0 | 0 |
| 0 | 0 | 0 | 0 | 0 | 0 | 0 |
| 1 | 2 | 0 | 0 | 0 | 0 | 1 |
| 0 | 0 | 0 | 0 | 0 | 0 | 0 |

FIG. 14F

Taxonomic distributions of CRC, adenoma and their paired surgically-resected distal normal samples, and colonoscopy biopsies.

(a) Phylum level assignments

| Patient ID | S12 | S13 | S13 | S14 |
|---|---|---|---|---|
| Status | Biopsy | Biopsy | Biopsy | Biopsy |
| Location | Right | Left | Right | Left |
| Status_Location | Biopsy_Righ | Biopsy_Left | Biopsy_Righ | Biopsy_Left |
| Biofilm | negative | negative | negative | negative |
| SampleName | S12.Biopsy.R | S13.Biopsy.L | S13.Biopsy.R | S14.Biopsy.L |
| Bacteria_Acidobacteria | 1 | 0 | 0 | 0 |
| Bacteria_Actinobacteria | 1 | 0 | 0 | 2 |
| Bacteria_Bacteroidetes | 1012 | 447 | 1190 | 176 |
| Bacteria_Cyanobacteria | 0 | 1 | 0 | 0 |
| Bacteria_Deferribacteres | 2 | 0 | 0 | 0 |
| Bacteria_Firmicutes | 538 | 394 | 221 | 557 |
| Bacteria_Fusobacteria | 0 | 0 | 0 | 0 |
| Bacteria_Gemmatimonadetes | 0 | 0 | 0 | 0 |
| Bacteria_OP11 | 0 | 0 | 0 | 0 |
| Bacteria_Other | 7 | 21 | 10 | 5 |
| Bacteria_Proteobacteria | 2432 | 3036 | 2524 | 2909 |
| Bacteria_TM7 | 0 | 0 | 0 | 1 |
| Bacteria_Tenericutes | 0 | 0 | 0 | 0 |
| Bacteria_Verrucomicrobia | 0 | 0 | 0 | 0 |
| Root_Other | 2 | 5 | 1 | 2 |

FIG. 14F Cont.

| S14 Biopsy Right Biopsy_Right negative S14.Biopsy.R | S15 Biopsy Left Biopsy_Left negative S15.Biopsy.L | S15 Biopsy Right Biopsy_Right negative S15.Biopsy.R | S17 Biopsy Left Biopsy_Left negative S17.Biopsy.L | S17 Biopsy Right Biopsy_Right negative S17.Biopsy.R | S18 Biopsy Left Biopsy_Left negative S18.Biopsy.L | S18 Biopsy Right Biopsy_Right negative S18.Biopsy.R |
|---|---|---|---|---|---|---|
| 0 | 0 | 0 | 0 | 0 | 2 | 0 |
| 0 | 0 | 0 | 0 | 0 | 0 | 4 |
| 461 | 1898 | 2214 | 2276 | 3152 | 298 | 194 |
| 0 | 0 | 0 | 4 | 0 | 0 | 1 |
| 0 | 0 | 0 | 0 | 0 | 0 | 0 |
| 611 | 1138 | 1187 | 1446 | 1085 | 1844 | 796 |
| 0 | 0 | 0 | 7 | 5 | 213 | 24 |
| 0 | 0 | 0 | 0 | 0 | 0 | 0 |
| 2 | 4 | 5 | 69 | 37 | 7 | 32 |
| 2709 | 84 | 125 | 158 | 29 | 748 | 2125 |
| 0 | 0 | 0 | 0 | 0 | 0 | 0 |
| 0 | 0 | 0 | 0 | 0 | 0 | 0 |
| 0 | 0 | 0 | 0 | 0 | 1 | 2 |

FIG. 14G

Taxonomic distributions of CRC, adenoma and their paired surgically-resected distal normal samples, and colonoscopy biopsies.

(a) Phylum level assignments

| Patient ID | S19 | S19 | S20 |
|---|---|---|---|
| Status | Biopsy | Biopsy | Biopsy |
| Location | Left | Right | Left |
| Status_Location | Biopsy_Left | Biopsy_Right | Biopsy_Left |
| Biofilm | negative | negative | negative |
| SampleName | S19.Biopsy.Left | S19.Biopsy.Right | S20.Biopsy.Left |
| Bacteria_Acidobacteria | 0 | 0 | 0 |
| Bacteria_Actinobacteria | 0 | 1 | 2 |
| Bacteria_Bacteroidetes | 7414 | 6523 | 3895 |
| Bacteria_Cyanobacteria | 0 | 0 | 0 |
| Bacteria_Deferribacteres | 0 | 0 | 0 |
| Bacteria_Firmicutes | 227 | 681 | 1313 |
| Bacteria_Fusobacteria | 0 | 1 | 0 |
| Bacteria_Gemmatimonadetes | 0 | 0 | 0 |
| Bacteria_OP11 | 1 | 1 | 2 |
| Bacteria_Other | 433 | 377 | 824 |
| Bacteria_Proteobacteria | 0 | 0 | 0 |
| Bacteria_TM7 | 0 | 0 | 0 |
| Bacteria_Tenericutes | 0 | 0 | 0 |
| Bacteria_Verrucomicrobia | 0 | 5 | 0 |
| Root_Other | | | |

FIG.14G Cont.

| S20 Biopsy Right Biopsy_Right negative S20.Biopsy.Right | S21 Biopsy Left Biopsy_Left negative S21.Biopsy.Left | S21 Biopsy Right Biopsy_Right negative S21.Biopsy.Right |
|---|---|---|
| 0 | 1 | 1 |
| 0 | 1 | 461 |
| 4448 | 65 | 488 |
| 0 | 0 | 0 |
| 0 | 0 | 0 |
| 784 | 855 | 1735 |
| 0 | 3 | 40 |
| 0 | 0 | 0 |
| 0 | 0 | 0 |
| 4 | 11 | 38 |
| 393 | 3378 | 2030 |
| 0 | 0 | 0 |
| 0 | 0 | 0 |
| 0 | 0 | 1 |
| 2 | 4 | 25 |

FIG. 15

|      | Biofilm +   | Biofilm -  | p value |
|------|-------------|------------|---------|
| KRAS | 2/15 (13%)  | 4/16 (25%) | 0.650   |
| BRAF | 4/15 (27%)  | 0/16 (0%)  | 0.043   |
| MSI  | 5/15 (33%)  | 2/16 (13%) | 0.760   |

BIOFILM FORMATION TO DEFINE RISK FOR COLON CANCER

CROSS REFERENCE TO RELATED APPLICATIONS

This application is a national stage application, filed under 35 U.S.C. § 371, of International Application No. PCT/US2014/055123, filed on Sep. 11, 2014, which claims priority to U.S. Provisional Patent Application Ser. No. 61/876,995, filed Sep. 12, 2013. The entire contents of each of which are hereby incorporated by reference in their entireties.

STATEMENT OF RIGHTS TO INVENTIONS MADE UNDER FEDERALLY SPONSORED RESEARCH

This invention was made with government support under grant no. CA151393 and CA170492 awarded by the National Institutes of Health. The government has certain rights in the invention.

FIELD OF THE INVENTION

The present invention relates to compounds, compositions, and methods for the study, diagnosis, and treatment of cancer and/or other proliferative diseases, disorders, or conditions. In certain embodiments, the invention specifically relates to detection, prevention and treatment of colorectal cancer (CRC) in a subject via assessment of the presence and/or structural attributes of intestinal and/or colonic bacteria.

BACKGROUND OF THE INVENTION

The human colonic epithelium exists in close proximity to trillions of bacteria. Animal models and human epidemiological studies have long implicated the enteric microbiome in the etiopathogenesis of colorectal cancer (CRC). Mechanisms by which the microbiome might initiate and/or promote colon tumor development remain obscure, with evidence supporting DNA damage by oncogenic bacterial toxins and/or induction by the microbiota of select inflammatory pathways. Limited observations, to date, have supported dysbiosis in the CRC microbial community without consistent implication of an etiologic bacterial species or genus (1).

Sporadic colorectal cancer (CRC) results from accumulated DNA mutations in colonic epithelial cells. The mechanisms causing these colonic epithelial cell mutations and propagating premalignant clones have remained unclear. One prime candidate for initiation of the biologic changes defining CRC is an altered colonic microbiota that acts early in disease pathogenesis to initiate and then, over time, to promote CRC through direct effects on colonic epithelial cell biology and/or instigation of insidious chronic mucosal inflammation. However, clear associations between microbiota composition and CRC development have not been established.

SUMMARY OF THE INVENTION

The present invention is based, at least in part, upon the remarkable discovery that, when colorectal cancer (CRC) subjects were examined, essentially all right-sided colon cancers and a subset of left-sided colon cancers were identified to possess a biofilm. Such biofilms were associated with increased proliferation and decreased apoptosis of colonic epithelium, both of which are important elements in transformation to colon cancer. Without wishing to be bound by theory, such biofilms would likely have allowed for an increased concentration of bacteria to contact the colonic mucosa. In contrast, only 10% of normal colonoscopy colon biopsies were identified as biofilm positive. These results indicated that detection of biofilms in normal colonoscopy specimens would identify individuals at higher risk for development of colon cancer. Furthermore, interventions such as antibiotics or probiotics that eliminate biofilms from the colon mucosa of individuals are described herein for preventing and/or diminishing development of gastrointestinal tract cancers, particularly colon cancer.

In one aspect, the invention provides a method for treating or preventing a neoplastic condition in a subject that involves (i) detecting a bacterial biofilm within the gastrointestinal tract of a subject; and (ii) administering an antimicrobial agent or a probiotic agent to the subject in an amount effective to reduce the size of the bacterial biofilm, thereby treating or preventing a neoplastic condition in the subject.

In one embodiment, the neoplastic condition is a colorectal cancer or a colorectal adenoma. In another embodiment, the bacterial biofilm is detected within the colon (optionally, the right ascending colon) of the subject. In a related embodiment, the bacterial biofilm has invaded the mucus layer of the gastrointestinal tract of the subject.

In another embodiment, the bacterial biofilm occupies a linear distance of at least 200 µm of the epithelial surface.

In a further embodiment, the density of bacteria in the bacterial biofilm is at least $10^8$ bacteria/ml.

In one embodiment, the bacterial biofilm includes a Bacteroidetes, Firmicutes, Gammaproteobacteria, Fusobacteria, and/or Lachnospiraceae bacteria. Optionally, the Lachnospiraceae bacteria is a *Clostridium, Ruminococcus* or *Butyrivibrio* bacteria.

In another embodiment, the bacterial biofilm comprises a Fusobacteria-dominant microbiota membership.

In one embodiment, the detecting step comprises colonoscopy.

In another embodiment, the detecting step comprises administering a bacteria visualizing agent or biofilm visualizing agent to the subject or a sample of the subject.

In a further embodiment, the bacteria visualizing agent or biofilm visualizing agent is a FISH probe or other bacteria labeling agent or labeling agent taken up by polymeric matrix of the biofilm.

In another embodiment, the FISH probe or other bacteria labeling agent or labeling agent taken up by polymeric matrix of the biofilm is selected from FIG. 11.

In one embodiment, the detecting step is performed upon fixative-preserved tissue (e.g., Carnoy's fixative preservation of tissue, with detection of bacterial biofilms using fluorescent in situ hybridization directed with labeled probes, e.g., to bacterial ribosomal RNA).

In a further embodiment, the detecting step involves administering a FISH probe or other bacteria labeling agent or label of the polymeric biofilm matrix to the colon mucosa of the subject, optionally during colonoscopy.

In another embodiment, the antimicrobial agent is an antibiotic. In a related embodiment, the antibiotic is clindamycin, beta lactams (including but not limited to carbenicillin, cefoperazone, cefamandole, penicillin), macrolides (including but not limited to erythromycin), chloramphenicol, aminoglycosides, fluoroquinolones, carbapenems or sulbactam.

In a further embodiment, the probiotic agent includes one or more of the following species: *Bacteroides, Prevotella, Porphyromonas, Fusobacterium, Sutterella, Bilophila, Campylobacter, Wolinella, Butyrovibrio, Megamonas, Desulfomonas, Desulfovibrio, Bifidobacterium, Lactobacillus, Eubacterium, Actinomyces, Eggerthella, Coriobacterium, Propionibacterium*, other genera of non-sporeforming anaerobic gram-positive bacilli, *Bacillus, Peptostreptococcus* (and newly created genera originally in *Peptostreptococcus*), *Peptococcus, Acidaminococcus, Ruminococcus, Megasphaera, Gaffkya, Coprococcus, Veillonella, Sarcina*, certain of the species of *Clostridium, Aerococcus, Streptococcus, Enterococcus, Pediococcus, Micrococcus, Staphylococcus, Corynebacterium*, and species of the genera having the Enterobacteriaceae and Pseudomonadaceae.

In another embodiment, the detecting step includes identification of bacterial species or polymeric biofilm matrix within a sample of the subject. Optionally, the sample of the subject is a colonic biopsy sample or a stool sample. In a related embodiment, identification is based upon detection of bacterial DNA or RNA sequences or polymeric biofilm matrix.

In a further embodiment, the antimicrobial agent reduces colon epithelial proliferation or increases apoptosis in the colon cells of the subject, optionally in colon tumor cells of the subject.

In one embodiment the detecting step includes identification of an aggregated association of Bacterioidetes, Firmicutes, Proteobacteria, Lahnospiracae, Fusobacteria, *Lactococcus, Leuconostoc, Comamonas* or other Burkholderiales in the subject.

In another embodiment, the detecting step includes identification of a reduced level of a candidate Ruminococcaceae member, Bacilli or Bacteroidetes in the subject.

In a further embodiment, the method of the invention further includes administering a chemotherapeutic agent to the subject.

In another aspect, the invention provides a method for identifying a subject at increased risk of developing cancer that involves detecting a bacterial biofilm within the gastrointestinal tract of the subject, thereby identifying the subject as at increased risk of developing cancer.

A further aspect of the invention provides a method for treating or preventing cancer in a subject that involves administering an antimicrobial agent or a probiotic agent to a subject harboring a bacterial biofilm within the gastrointestinal tract of the subject, wherein the antimicrobial agent or probiotic agent reduces or eliminates the presence of a the biofilm, thereby treating or preventing cancer in the subject.

Another aspect of the invention provides a kit for identifying the presence of a biofilm within the gastrointestinal tract of a subject that includes a bacteria visualizing agent and/or a biofilm visualizing agent, and instructions for its use.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "proliferative disease" or "cancer" as used herein is meant, a disease, condition, trait, genotype or phenotype characterized by unregulated cell growth or replication as is known in the art; including colorectal cancer, as well as, for example, leukemias, e.g., acute myelogenous leukemia (AML), chronic myelogenous leukemia (CML), acute lymphocytic leukemia (ALL), and chronic lymphocytic leukemia, AIDS related cancers such as Kaposi's sarcoma; breast cancers; bone cancers such as Osteosarcoma, Chondrosarcomas, Ewing's sarcoma, Fibrosarcomas, Giant cell tumors, Adamantinomas, and Chordomas; Brain cancers such as Meningiomas, Glioblastomas, Lower-Grade Astrocytomas, Oligodendrocytomas, Pituitary Tumors, Schwannomas, and Metastatic brain cancers; cancers of the head and neck including various lymphomas such as mantle cell lymphoma, non-Hodgkins lymphoma, adenoma, squamous cell carcinoma, laryngeal carcinoma, gallbladder and bile duct cancers, cancers of the retina such as retinoblastoma, cancers of the esophagus, gastric cancers, multiple myeloma, ovarian cancer, uterine cancer, thyroid cancer, testicular cancer, endometrial cancer, melanoma, lung cancer, bladder cancer, prostate cancer, lung cancer (including non-small cell lung carcinoma), pancreatic cancer, sarcomas, Wilms' tumor, cervical cancer, head and neck cancer, skin cancers, nasopharyngeal carcinoma, liposarcoma, epithelial carcinoma, renal cell carcinoma, gallbladder adeno carcinoma, parotid adenocarcinoma, endometrial sarcoma, multidrug resistant cancers; and proliferative diseases and conditions, such as neovascularization associated with tumor angiogenesis, macular degeneration (e.g., wet/dry AMD), corneal neovascularization, diabetic retinopathy, neovascular glaucoma, myopic degeneration and other proliferative diseases and conditions such as restenosis and polycystic kidney disease, and other cancer or proliferative disease, condition, trait, genotype or phenotype that can respond to the modulation of its environment (e.g., treating the environment with an antibiotic effective against a bacterial bioform), alone or in combination with other therapies.

By "subject" is meant an organism to which the methods of the invention can be applied and/or to which the agents of the invention can be administered. A subject can be a mammal, including a human, or a mammalian organ or mammalian cells, including a human organ and/or human cells.

As used herein, "neoplasia" means a disease state of a human or an animal in which there are cells and/or tissues which proliferate abnormally. Neoplastic conditions include, but are not limited to, cancers, sarcomas, tumors, leukemias, lymphomas, and the like. A neoplastic condition refers to the disease state associated with the neoplasia. Colon cancer (e.g., colorectal cancer), lung cancer and ovarian cancer are examples (non-limiting) of a neoplastic condition.

A "cancer" in a subject refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within a subject, or may be a non-tumorigenic cancer cell, such as a leukemia cell. Examples of cancer include but are not limited to colon cancer, colorectal cancer, breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, esophageal cancer, gastrointestinal cancer, glioblastoma, hepatic carcinoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, and vulval cancer.

As used herein, the term "tumor" means a mass of transformed cells that are characterized by neoplastic uncontrolled cell multiplication and at least in part, by containing angiogenic vasculature. The abnormal neoplastic cell growth is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic.

The term "biofilm" as used herein refers to an aggregate of bacterial microorganisms in which bacterial cells adhere to each other and/or to a surface. These adherent cells are often covered with a matrix of extracellular polymeric substance (EPS), which is produced by the cells. Biofilm EPS has been characterized as composed of extracellular DNA, proteins, and polysaccharides. Such biofilms may form on any living or non-living surfaces, in particular both on solid surfaces as colonies and/or on liquid surfaces as pellicles. Microbial cells growing in a biofilm are physiologically distinct from planktonic cells of the same organism. In certain aspects of the invention, bacterial formations within the gastrointestinal tract of a subject are defined as biofilms if such formations are of a minimal size. In particular, exemplified biofilms were characterized as a massive bacterial invasion (>$10^9$ bacteria/ml) of the mucus layer spanning at least a linear distance of 200 µm of the epithelial surface; however, as described in greater detail below, a range of bacterial density and/or size cutoffs may be selected as defining a biofilm within a subject.

The phrase "antimicrobial" as used herein, refers to a property of a substance (e.g., a compound or a composition) that can effect a parameter of a microorganism, including death, eradication, elimination, reduction in number, reduction of growth rate, inhibition of growth, change in population distribution of one or more species of microbial life forms. This term encompasses antibacterial agents and antibiotics.

An "antimicrobial agent", as used herein, refers to an agent that is capable of decreasing or eliminating or inhibiting the growth of microorganisms such as that term is known in the art (exemplary microorganisms include microbes such as bacteria, fungi, viruses and other pathogens).

As used herein, the term "antibacterial agent" is defined as a compound having either a bactericidal or bacteriostatic effect upon bacteria contacted by the compound. As used herein, the term "bactericidal" is defined to mean having a destructive killing action upon bacteria. As used herein, the term "bacteriostatic" is defined to mean having an inhibiting action upon the growth of bacteria. Non-limiting exemplary antibacterial agent(s) include those classified as aminoglycosides, beta-lactams, quinolones or fluoroquinolones, macrolides, sulfonamides, sulfamethaxozoles, tetracyclines, streptogramins, oxazolidinones (such as linezolid), clindamycins, lincomycins, rifamycins, glycopeptides, polymxins, lipo-peptide antibiotics, as well as pharmacologically acceptable sodium salts, pharmacologically acceptable calcium salts, pharmacologically acceptable potassium salts, lipid formulations, derivatives and/or analogs of the above.

As used herein, the term "antibiotic" includes antimicrobial agents isolated from natural sources or chemically synthesized. The term "antibiotic" refers to antimicrobial agents for use in human therapy. Exemplary antibiotics include: tetracyclines, fluoroquinolones, chloramphenicol, penicillins, cephalosporins, puromycin, nalidixic acid, and rifampin. Additional specific examples of antibiotics include clindamycin, carbenicillin, cefoperazone, cefamandole, sulfonamides, quinolones, oxazolidinones, carbapenems, aminoglycosides, erythromycin, tetracycline and sulbactam.

As used in the context of embodiments of the present invention, the phrase "antimicrobial effective amount" describes an amount of an antimicrobial agent which will effect one or more parameters of a microorganism, including death, eradication, elimination, reduction in number, reduction of growth rate, inhibition of growth, change in population distribution of one or more species of microbial life forms, as described herein. In some embodiments, an antimicrobial effective amount is an amount that reduces to some extent the population of a microorganism in a biofilm structure and/or within the gastrointestinal tract of a subject.

The phrase "anti-biofilm formation activity" as used herein refers to the capacity of a substance to effect the prevention of formation of a biofilm of bacterial, fungal and/or other cells; and/or to effect a disruption and/or the eradication of an established and/or matured biofilm of bacterial, fungal and/or other cells; and/or to effect a reduction in the rate of buildup of a biofilm of bacterial, fungal and/or other cells on a surface (e.g., within the gastrointestinal tract of a subject).

The phrase "anti-biofilm formation compound/composition/agent" as used herein refers to a substance having an anti-biofilm formation activity, as defined herein.

A therapy that can be administered alone or in conjunction with one or more of the therapies discussed herein, is probiotic therapy. "Probiotic" therapy is intended to mean the administration of organisms and substances which help to improve the environment of the intestinal tract by inhibiting the disproportional growth of bacteria which produce toxins in the intestinal tract. For example, in healthy humans, the small intestine is colonized by lactobacilli (e.g., *L. acidophilus*), *Bifidobacterium*, gram-negative anaerobes, enterococci, and Enterobacteriaceae; the large intestine is colonized mainly by obligate anaerobes (e.g., *Bacteroides* sp., gram-positive anaerobic cocci, *Clostridium* sp., non-spore forming anaerobic gram-positive rods, Enterobacteriaceae (mainly *E. coli*), and enterococci). These bacteria produce substances which suppress harmful bacteria; for example, bifidobacteria produce lactic and acetic acid, decreasing the pH of the intestines. They can also activate macrophages, which also help suppress harmful bacteria.

Probiotic agents comprise one or more of the following normal inhabitants of the human intestinal tract: any species of *Bacteroides, Prevotella, Porphyromonas, Fusobacterium, Sutterella, Bilophila, Campylobacter, Wolinella, Butyrovi-* brio, *Megamonas, Desulfomonas, Desulfovibrio, Bifidobacterium, Lactobacillus, Eubacterium, Actinomyces, Eggerthella, Coriobacterium, Propionibacterium*, other genera of non-sporeforming anaeroibic gram-positive bacilli, *Bacillus, Peptostreptococcus* (and newly created genera originally in *Peptostreptococcus*), *Peptococcus, Acidaminococcus, Ruminococcus, Megasphaera, Gaffkya, Coprococcus, Veillonella, Sarcina*, certain of the species of *Clostridium, Aerococcus, Streptococcus, Enterococcus, Pediococcus, Micrococcus, Staphylococcus, Corynebacterium*, and species of the genera comprising the Enterobacteriaceae and Pseudomonadaceae, as well as mixtures thereof.

Certain strains for supplementation are those that are typically permanent residents of the human intestinal tract and which do not produce toxins. Normal human intestinal flora are better adapted to the environment (bile acids, anaerobic conditions, etc.) of the human intestinal tract, and are more likely to survive and colonize the human intestinal tract. Certain species such as *L. bulgaricus* and *S. thermophilus*, for example, are commonly used as probiotics, but are not normal constituents of human gut flora, and such species apparently do not colonize the intestinal tract well.

A probiotic therapy can be designed to be administered as a mixture of a large number of species that are normal, benign inhabitants of the gut, optionally in the general proportion in which they are found in healthy humans. For example, *E. coli* is-a common enteric inhabitant, but makes up only about {fraction (1/1000)} of the bowel flora found in healthy humans, so would be a relatively small proportion of a probiotic mixture. Description of normal human gut flora and relative abundances can be found in FIG. 2, the tables below, Finegold, J. Assoc. Anaerobic. Infect. Res. 28:206-213 (1998), and Finegold et al., Normal Indigenous Intestinal Flora, Chap. 1, in Hentges, D. J., ed. Human Intestinal Microflora in Health and Diseas, New York, Academic Press, p. 3-31, 1983; both herein incorporated by reference.

Certain probiotic diet items have also been described, e.g., fermented vegetables (sauerkraut, kimchi, collars, kale, celery), yogurt drinks, tempeh, natto and fermented raw milk (e.g., kefir, yogurt).

As used herein, the terms "bacteria visualizing agent" and "biofilm visualizing agent" refer to any agents capable of enhancing an observer's visual detection of a bacteria/biofilm either within a subject or within a biopsy or sample derived from a subject. Exemplary such visualizing agents include fluorescent agents such as FISH probes.

As used herein, the term "cancer therapy" refers to a therapy useful in treating cancer. Examples of anti-cancer therapeutic agents include, but are not limited to, antibacterial agents as described herein as well as, e.g., surgery, chemotherapeutic agents, immunotherapy, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also contemplated for use with the methods described herein.

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, Astrazeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (GSK572016, GlaxoSmithKline), Lonafarnib (SCH 66336), Sorafenib (BAY43-9006, Bayer Labs.), and Gefitinib (IRESSA®, Astrazeneca), AG1478, AG1571 (SU 5271; Sugen), alkylating agents such as Thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozcicsin, carzcicsin and bizcicsin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, anthramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacytidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone;

podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in this definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON-.toremifene; (ii) aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those which inhibit expression of genes in signaling pathways implicated in aberrant cell proliferation, such as, for example, PKC-alpha, Ralf and H-Ras; (viii) ribozymes such as a VEGF expression inhibitor (e.g., ANGIOZYME® ribozyme) and a HER2 expression inhibitor; (ix) vaccines such as gene therapy vaccines, for example, ALLOVECTIN° vaccine, LEUVECTIN® vaccine, and VAXID® vaccine; PROLEUKIN® rIL-2; LURTOTECAN® topoisomerase 1 inhibitor; ABARELIX® rmRH; (x) antiangiogenic agents such as bevacizumab (AVASTIN®, Genentech); and (xi) pharmaceutically acceptable salts, acids or derivatives of any of the above.

The term "cancer therapy", as used herein, includes the antimicrobial agents and probiotic agents of the instant invention, as well as art-recognized forms of treating neoplastic conditions.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (e.g., vincristine and vinblastine), taxanes, and topoisomerase II inhibitors such as doxorubicin, epirubicin, daunorubicin, etoposide, and bleomycin. The agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

In one embodiment, as used herein, the term "treat" or treatment" refers to reducing or alleviating at least one adverse clinical symptom associated with cancer, e.g., pain, swelling, low blood count etc. In another embodiment, the term "treat" or treatment" refers to slowing or reversing the progression neoplastic uncontrolled cell multiplication, i.e. shrinking existing tumors and/or halting tumor growth. In another embodiment, the term "treat" or treatment" refers to inducing apoptosis in cancer or tumor cells in the subject.

As used herein, the term "a therapeutically effective amount" refers to an amount sufficient to achieve the intended purpose of treating cancer. In one embodiment, a therapeutically effective amount of an antimicrobial agent (e.g., antibiofilm agent) described herein for a method of treating cancer is an amount of sufficient to induce apoptosis of cancer cells of the subject as compared to in the absence of one or both such agents. In other embodiments, the amount(s) that is safe and sufficient to treat, delay the development of a tumor, and/or delay further growth of the tumor. In some embodiments, the amount can thus cure or result in amelioration of the symptoms of cancer and tumor growth, slow the course of cancer progression, slow or inhibit a symptom of cancer, slow or inhibit the establishment of secondary symptoms of cancer or inhibit the development of a secondary symptom of the cancer. For example, an effective amount of an antimicrobial agent described herein can inhibit further tumor growth, cause a reduction in size or even completely halt tumor growth, shrink the sizes of tumor, even complete regression of tumor, and reduce clinical symptoms associated with tumor. In certain embodiments, an effective amount for treating cancer is an amount of an antimicrobial agent described herein sufficient to result in a reduction or complete removal of the symptoms of the disorder, disease, or medical condition. In some embodiments, an effective amount for treating or ameliorating a disorder, disease, or medical condition is an amount sufficient to result in a reduction or complete removal of the symptoms of the disorder, disease, or medical condition. In the case of tumor (e.g., a cancerous tumor), the therapeutically effective amount of the antimicrobial agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antimicrobial agent may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life. The effective amount of a given therapeutic agent will vary with factors such as the nature of the agent, the route of administration, the size and species of the animal to receive the therapeutic agent, and the purpose of the administration. Thus, it is not possible or prudent to specify an exact "therapeutically effective amount". However, for any given case, an appropriate "effective amount" can be determined by a skilled artisan according to established methods in the art using only routine experimentation.

By "reduce or inhibit" is meant the ability to cause an overall decrease of 20% or greater, or 50% or greater, or 75%, 85%, 90%, 95%, or greater. Reduce or inhibit can refer to the symptoms of the disorder being treated, the presence or size of metastases, the size of the primary tumor, or the size or number of the blood vessels in angiogenic disorders.

The phrase "pharmaceutically acceptable carrier" refers to a carrier for the administration of a therapeutic agent. Exemplary carriers include saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Certain methodologies of the instant invention include a step that involves comparing a value, level, feature, characteristic, property, etc. to a "suitable control", referred to interchangeably herein as an "appropriate control". A "suitable control" or "appropriate control" is a control or standard familiar to one of ordinary skill in the art useful for comparison purposes. In one embodiment, a "suitable control" or "appropriate control" is a value, level, feature, characteristic, property, etc. determined prior to performing a treatment and/or agent administration methodology, as described herein. For example, a transcription rate, mRNA level, translation rate, protein level, biological activity, cellular characteristic or property, genotype, phenotype, etc. can be determined prior to introducing a treatment and/or agent of the invention to a subject. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

"Treatment", or "treating" as used herein, is defined as the application or administration of a therapeutic agent or combination of therapeutic agents (e.g., an antimicrobial agent and, optionally, another cancer preventing and/or therapeutic agent (e.g., chemotherapeutic)) to a patient, or application or administration of a therapeutic agent to an isolated tissue or cell line from a patient, who has a disorder with the purpose to cure, heal, alleviate, relieve, alter, remedy, ameliorate, improve or affect the disease or disorder, or symptoms of the disease or disorder. The term "treatment" or "treating" is also used herein in the context of administering agents prophylactically. The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. The term "patient" includes human and other mammalian subjects that receive either prophylactic or therapeutic treatment.

As used herein, a "tissue sample" refers to a portion, piece, part, segment, or fraction of a tissue which is obtained or removed from an intact tissue of a subject, preferably a human subject. In one embodiment, the tissue sample is a gastrointestinal tract sample, optionally a colorectal sample.

As used herein, a "tumor sample" refers to a portion, piece, part, segment, or fraction of a tumor, for example, a tumor which is obtained or removed from a subject (e.g., removed or extracted from a tissue of a subject), preferably a human subject.

In one embodiment, the tissue sample is obtained from a biopsy procedure in the subject. In another embodiment, the tissue sample is obtained from a surgical procedure to remove a tumor mass from the subject.

As used herein, the term "agent" refers to any molecule, compound, nucleic acid, nucleic acid based moiety, antibody, antibody-based molecule, protein, protein-based molecule and/or substance for use in the prevention, treatment, management and/or diagnosis of cancer.

As used herein, the term "cancer cells" refer to cells that acquire a characteristic set of functional capabilities during their development, including the ability to evade apoptosis, self-sufficiency in growth signals, insensitivity to anti-growth signals, tissue invasion/metastasis, significant growth potential, and/or sustained angiogenesis. The term "cancer cell" is meant to encompass both pre-malignant and malignant cancer cells.

As used herein, the term "compound" refers to small molecules. Examples of such small molecules would include low molecular weight molecules. Other examples of compounds include molecules that are generated by organic synthesis, and low molecular weight molecules that are metabolites or anti-metabolites.

As used herein, the term "effective amount" refers to the amount of a therapy that is sufficient to result in therapeutic benefit to a patient with cancer, In one embodiment, the cancer patient has been diagnosed with a biofilm and, optionally, with CRC. In one embodiment, the effective amount is administered to a patient that has been diagnosed with cancer. The effective amount can result in the prevention of the development, recurrence, or onset of cancer and one or more symptoms thereof, to enhance or improve the efficacy of another therapy, reduce the severity, the duration of cancer, ameliorate one or more symptoms of cancer, prevent the advancement of cancer, cause regression of cancer, and/or enhance or improve the therapeutic effect(s) of another therapy. "Effective amount" also refers to the amount of a therapy that is sufficient to result in the prevention of the development, recurrence, or onset of cancer and one or more symptoms thereof, to enhance or improve the prophylactic effect(s) of another therapy, reduce the severity, the duration of cancer, ameliorate one or more symptoms of cancer, prevent the advancement of cancer, cause regression of cancer, and/or enhance or improve the therapeutic effect(s) of another therapy. In an embodiment of the invention, the amount of a therapy is effective to achieve one, two, three, or more results following the administration of one, two, three or more therapies: (1) a stabilization, reduction or elimination of the cancer stem cell population;

(2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor is maintained and does not increase or increases by less than 10%, preferably less than 5%, preferably less than 4%, preferably less than 2%, (12) an increase in the number of patients in remission, (13) an increase in the length or duration of remission, (14) a decrease in the recurrence rate of cancer, (15) an increase in the time to recurrence of cancer, and (16) an amelioration of cancer-related symptoms and/or quality of life.

As used herein, the term "in combination" in the context of the administration of a therapy to a subject refers to the use of more than one therapy for therapeutic benefit. The term "in combination" in the context of the administration can also refer to the prophylactic use of a therapy to a subject when used with at least one additional therapy. The use of the term "in combination" does not restrict the order in which the therapies (e.g., a first and second therapy) are administered to a subject. A therapy can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject which had, has, or is susceptible to cancer. The therapies are administered to a subject in a sequence and within a time interval such that the therapies can act together. In a particular embodiment, the therapies are administered to a subject in a sequence and within a time interval such that they provide an increased benefit than if they were administered otherwise. Any additional therapy can be administered in any order with the other additional therapy.

As used herein, the terms "prevent," "preventing" and "prevention" in the context of the administration of a therapy to a subject refer to the prevention or inhibition of the recurrence, onset, and/or development of a cancer or a symptom thereof in a subject resulting from the administration of a therapy (e.g., a prophylactic agent), or a combination of therapies (e.g., a combination of prophylactic agents). In some embodiments, such terms refer to one, two, three, or more results following the administration of one or more therapies: (1) a stabilization, reduction or elimination in the cancer cell population, (2) an increase in response rate, (3) an increase in the length or duration of remission, (4) a decrease in the recurrence rate of cancer, (5) an increase in the time to recurrence of cancer, (6) an increase in the disease-free, relapse-free, progression-free, and/or overall survival of the patient, and (7) an amelioration of cancer-related symptoms and/or quality of life. In specific embodiments, such terms refer to a stabilization, reduction or elimination of the cancer stem cell population.

As used herein, the term "therapeutically effective regimen" refers to a regimen for dosing, timing, frequency, and duration of the administration of one or more therapies for the treatment and/or management of cancer or a symptom thereof. In a specific embodiment, the regimen achieves one, two, three, or more of the following results: (1) a stabilization, reduction or elimination in the cancer cell population; (2) a stabilization or reduction in the growth of a tumor or neoplasm; (3) an impairment in the formation of a tumor; (4) eradication, removal, or control of primary, regional and/or metastatic cancer; (5) a reduction in mortality; (6) an increase in disease-free, relapse-free, progression-free, and/or overall survival, duration, or rate; (7) an increase in the response rate, the durability of response, or number of patients who respond or are in remission; (8) a decrease in hospitalization rate, (9) a decrease in hospitalization lengths, (10) the size of the tumor is maintained and does not increase or increases by less than 10%, preferably less than 5%, preferably less than 4%, preferably less than 2%, and (11) a increase in the number of patients in remission.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. Concentrations, amounts, cell counts, percentages and other numerical values may be presented herein in a range format. It is to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

BRIEF DESCRIPTION OF THE DRAWINGS

FIG. 1A shows results of FISH of all bacteria (red) on tumor, surgically-resected distal normal tissue and colonoscopy biopsies from ascending and descending colon counterstained with DAPI (scale bar 50 μm). FIG. 1B depicts the geographical distribution of tumors (CRC, n=31 and adenomas, n=6) with biofilm designation. FIG. 1C at top shows an SEM image depicting a mixed morphology bacterial biofilm on right colon tumor. Bottom panels show an SEM image of bacterial contact with host epithelium on right colon tumors (scale bar 2 μm top and bottom). FIG. 1D shows biofilm presence, density and depth measurements from right CRCs/surgical distal normal pairs (n=15), right adenomas/surgical distal normal pairs (n=4), left CRCs/surgical distal normal pairs (n=16), left adenomas/surgical distal normal pairs (n=2), and right/left paired colonoscopy biopsies (n=60). Biofilm density was not significantly different between CRCs or adenomas and their surgical distal normal pairs. Biofilm depth was significantly greater on CRCs (P=0.001) and adenomas (P=0.028) than their respective surgical distal normal pairs. Data displayed as bar and whisker graph where line designates the median, boxes the 25/75th percentile and whiskers the 95th percentile.

FIGS. 2A-2F show the result of FISH and sequencing analysis, which revealed invasive polymicrobial biofilms and transitioning microbial populations. FIGS. 2A-2C show multiprobe spectral images of FISH-targeted bacterial groups (40×). Bacteroidetes (green), Lachnospiraceae (magenta), Fusobacteria (cyan), Enterobacteriaceae (orange), *B. fragilis* (red) are represented within the biofilms, and tissue autofluorescence is white. FIG. 2A shows multi-group bacterial invasion of tumor tissue (white arrows). Right tumor with a Fusobacteria dominant (72% by sequence analysis) polymicrobial biofilm also containing Bacteroidetes, Lachnospiraceae, and Enterobacteriaceae. Dominant group in left tumor is Bacteroidetes. *B. fragilis*, Lachnospiraceae and Fusobacteria are also present. FIG. 2B shows bacterial biofilms on paired surgical distal normal tissue from CRC comprised of Lachnospiraceae, Bacteroidetes, and Enterobacteriaceae. FIG. 2C shows thin bacterial biofilms detected on right (Bacteroidetes, Lachnospiraceae and Enterobacteriaceae) and left (Bacteroidetes and Lachnospiraceae) colonoscopy biopsies from two different individuals. FIG. 2D at left shows all bacteria FISH (red) with DAPI counterstain of surgically resected distal normal tissue covered by a biofilm (20×). White arrows mark two sites of biofilm infiltration of the epithelial tissue (20×). FIG. 2D at right shows confocal z-stack of tissue invasion (40×) denoted by white box in FIG. 2D, left. Disordered epithelial cells and leukocytes were visible at the infiltrated sites, while surrounding epithelial cells were intact and ordered. (Scale bars: 50 μm in FIGS. 2A-2D). FIG. 2E shows a histogram of bacterial classes represented on biofilm positive and negative samples as defined by sequence analysis. FIG. 2F presents a PCoA plot (based on unweighted UniFrac distances) displaying similarity in mucosa community structure among all samples (each point reflects an individual sample). Normal control colonoscopy biopsies (n=21, red) and surgically-resected distal normal tissues without a biofilm (n=12 orange) transition to distal normal tissues with a biofilm (n=13, green) that cluster more closely to biofilm positive polyps (n=2, dark blue squares) and CRCs with (n=12, dark blue) and without (n=11, light blue) biofilms. Distal normal mucosa biofilm positive communities were significantly closer to tumor bacterial communities than those from colonoscopy biopsies (P=0.019, Mann-Whitney test). bf=biofilm.

FIGS. 3A-3D show that biofilms were associated with increased epithelial proliferation and decreased epithelial apoptosis. FIGS. 3A and 3B depict scoring of Ki67 positive cells from the base of the crypt to the luminal surface. Distal normal surgical tissue (A) with (n=17) and without (n=18) a biofilm as well as colonoscopy control biopsies (B) with (n=7) and without (n=10) a biofilm displayed increased proliferation in a biofilm setting. Data displayed as mean+/− SEM in groups based on distance from crypt base (<15 cells, 15-30 cells, >30 cells).

FIGS. 3C and 3D show the percent of apoptotic cells scored per 1000 epithelial cells counted. FIG. 3C shows distal normal surgical tissue with (n=17) and without (n=18) a biofilm, while FIG. 3D shows colonoscopy control biopsies (D) with (n=7) and without (n=10) a biofilm (*p<0.05, p<0.01,*p<0.001, **** p<0.0001).

FIG. 4 depicts a prototype (gross anatomical image) of mucosal tumor and distal normal tissue sites selected for analyses of surgically resected colons from CRC patients.

FIG. 6A depicts a right adenoma biofilm comprised solely of Enterobacteriaceae (orange) and Lachnospiraceae (magenta). FIG. 6B shows a right CRC biofilm composed of Bacteroidetes (green) and Lachnospiraceae (magenta). FIG. 6C shows a right CRC biofilm composed of Fusobacteria (cyan), Bacteroidetes (green) and Lachnospiraceae (magenta). (Scale bar: 50 μm).

FIG. 9 shows CRC/adenoma patient metadata.

FIGS. 10A-10C show colonoscopy biopsy patient metadata.

FIG. 11 shows FISH probes employed.

FIGS. 12A-12D show 16S V3-V5 amplicon sequencing statistics by sample.

FIGS. 13A-13H show shared and unique genera in paired tumor and surgically-resected distal normal tissue samples.

FIGS. 14A-14G show taxonomic distributions of CRC, adenoma and their paired surgically-resected distal normal samples, as well as colonoscopy biopsies.

FIG. 15 shows mutational analysis and methylator phenotype of CRCs.

DETAILED DESCRIPTION OF THE INVENTION

Figure 1A:
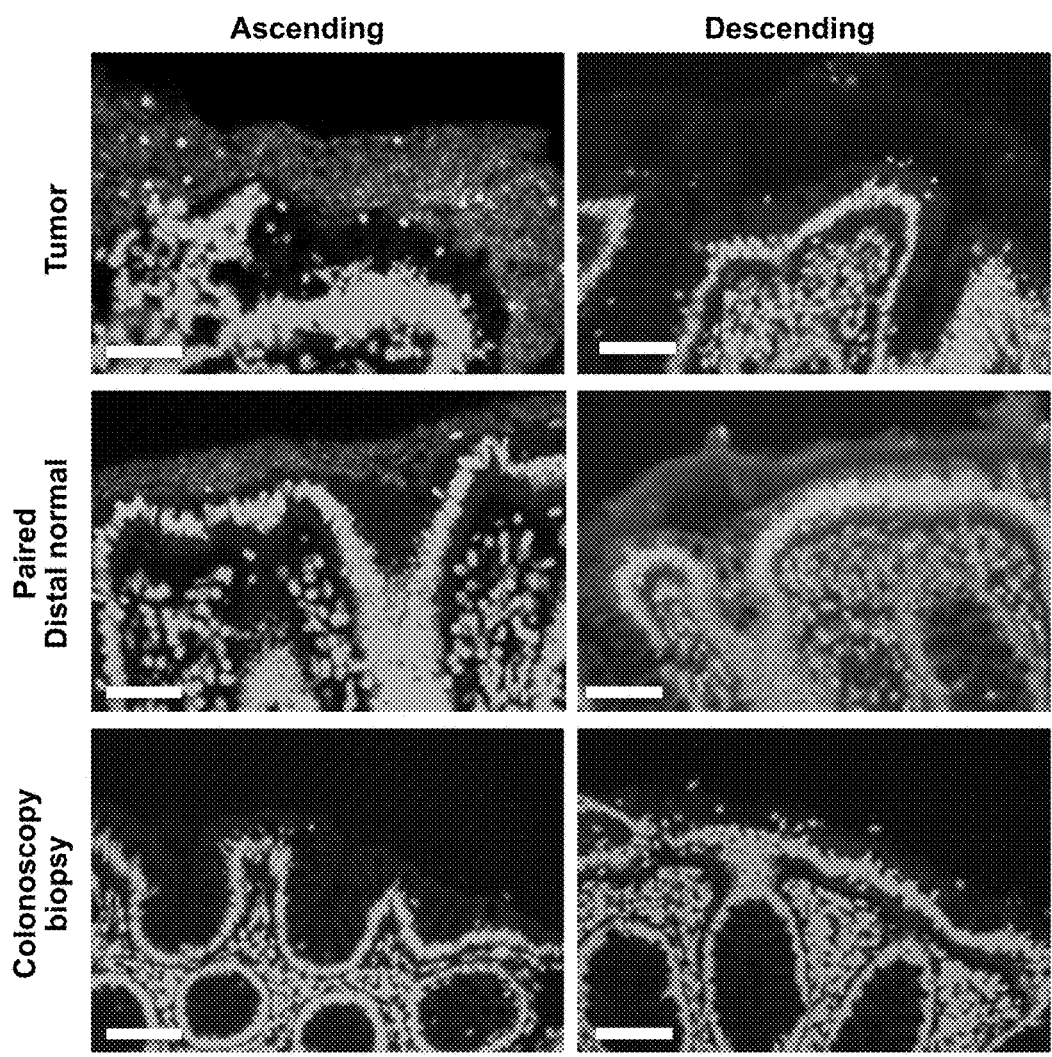
FIGS. 1A-1D show detection and quantification of bacterial biofilms on colon tumors.

The current invention is based, at least in part, upon the surprising discovery that invasive polymicrobial bacterial biofilms, known inducers of tissue inflammation, were identified universally on right-sided CRC, proximal to the hepatic flexure, but on only 13% of CRC distal to the hepatic flexure. Surprisingly, all patients with biofilm-positive tumors also had biofilms on their tumor-free mucosa distal from the tumor. High throughput sequencing revealed evidence for transitioning microbial populations between normal colon mucosa from healthy adults to biofilm-covered tumor-free colon mucosa distal from resected tumors to the mucosa directly overlying colon tumors. Despite the uniform association of biofilms with right-sided CRC, no consistent bacterial genus was identified as associated with tumors. Bacterial biofilms were associated with increased crypt epithelial cell proliferation in normal colon mucosa prior to tumor development. These data identified the mucosal microbiota organization, as opposed to its specific composition, as a critical factor accelerating oncogenic progression in right- and some left-sided CRC. Colon mucosal biofilm detection was therefore identified as likely to predict increased risk for development of sporadic CRC. Thus, colon mucosal bacterial biofilms, an established driver of chronic tissue inflammation, were identified as universally present on right-sided colon cancer.

Detection of patients at risk for colon cancer is a significant goal for early detection of colon cancer itself and potential interventions that may decrease the development of colon cancer. Achievement of either of these goals would significantly decrease morbidity and mortality from colon cancer, one of the leading cancers worldwide.

Here, methods for detecting patients at risk for colon cancer are provided, with such methods based upon assessment of the presence of a biofilm and/or biofilm-associated bacteria in a subject and/or a sample derived from a subject Importantly, methods for preventing and/or treating a neoplastic condition in a subject identified as harboring a biofilm and/or biofilm-associated bacteria (or other biofilm-associated microorganism) are also provided, as described in further detail herein.

Detection and Classification of Biofilms in a Subject

For purpose of detection and classification of biofilms for exemplary studies, biofilms were characterized as a massive bacterial invasion ($>10^9$ bacteria/ml) of the mucus layer spanning at least a linear distance of 200 μm of the epithelial surface. However, a range of bacterial density and/or size cutoffs can also be employed to identify when a bacterial structure constitutes a biofilm within a subject. Exemplary alternative cutoff values for detecting a biofilm in a subject based upon bacterial invasion include >100, >1000, >10000, >100000, >$10^6$, >$10^7$, >$10^8$, >$10^9$, >$10^{10}$, >$10^{11}$ and >$10^{12}$ bacteria/ml. Exemplary alternative cutoff values for detecting a biofilm in a subject based upon size include a linear distance of at least 20, 30, 40, 50, 60, 70, 80, 90, 100, 110, 120, 130, 140, 150, 160, 170, 180, 190, 210, 220, 230, 240, 250, 300, 350, 400, 450 and 500 μm, and at least 1, 2, 3, 4, 5, 10, 15, 20, 25, 30, 35, 40, 45, 50, 100, 200, and 500 mm.

Colon Biology and Flora

When healthy, the colon is covered by a mucus layer that segregates the microbiota from direct contact with the host colonic epithelium. Breaches of this protective mucus layer with resulting increased contact between mucosal microbiota and the colonic epithelial cells has been proposed as a critical first step in inciting changes in tissue biology and/or inflammation that yield chronic colonic disease such as inflammatory bowel disease. Concomitant with increased access to the mucosal epithelium, microbial community communication (such as quorum sensing) has been predicted to change, modifying bacterial structure and function and often resulting in biofilm formation (2). Biofilms have been defined as aggregations of microbial communities encased in a polymeric matrix that adhere to either biological or non-biological surfaces. Biofilms that invade the mucus layer and come into direct contact with mucosal epithelial cells have indicated pathology although limited detection of biofilms in otherwise histologically normal mucosa has been observed in the colon (3). Biofilms characterize numerous chronic mucosal disease states in and outside of the colon (including inflammatory bowel diseases, cystic fibrosis, pharyngo-tonsillitis, otitis media, rhinosinusitis, urethritis and vaginitis) where direct bacterial contact with epithelial cells results in perturbed epithelial function and chronic inflammation. However, no association of biofilms with CRC pathologic states has been reported.

Additional Examination of Biofilms as Cancer-Causing Agents

Prospective epidemiologic studies to directly test the hypothesis that biofilm formation (and its associated dysbiosis) preceded and potentially contributed to CRC formation or propagation are in preparation. While not wishing to be bound by theory, the relationship between inflammation and cancer in the gastrointestinal system has been well-established through investigations of animal models and clinical observations. While it has long been suspected that bacteria contribute to chronic inflammation leading to CRC, the studies described herein represent the first time that bacterial biofilms, a known driver of tissue inflammation, have been identified on CRC. The presence of a biofilm increased direct access of potentially oncogenic bacteria and their antigens or toxins to an unshielded epithelial surface where bacterial virulence determinants can induce epithelial cell mutations central to the development of CRC. Individual genetic polymorphisms likely governed the composition of the mucosal immune response to the mucosal biofilms, with Th17-dominant mucosal immune responses increasingly associated with oncogenesis and poor outcome in CRC (13, 14). A key observation linking biofilm formation to tumor biology was the instant identification of the tight association between mucosal biofilm formation and the pro-cancerous state of increased epithelial proliferation and decreased apoptosis. Thus, the progressive microbial community dysbiosis identified in the present sequence analyses potentially induced the colonic epithelial cell biologic and mutational changes that characterize CRC. In turn, the mucosal microbial community dysbiosis might have been molded, at least in part, by the altered biology of colonic epithelial cell mutations with clonal expansion (15). The clustering of surgically-resected distal normal biofilm-positive colon tissues with biofilm-covered adenomas and CRC further supported the hypothesis that biofilms contribute to a transition from normal to tumorous state in a subset of CRCs. The instant observations that CRC biofilms were universally present on right-sided CRCs and adenomas located proximal to the hepatic flexure while being largely absent from the left-sided tumors indicated that the microbial community organization with invasion into the mucus layer, rather than its composition identified by sequencing, was pivotal to regional colon oncogenesis. Growing epidemiologic, clinicopathologic and genetic evidence has suggested that right and left colon cancers should be considered as different tumor entities (16, 17). The instant findings have provided additional support for this idea and have revealed a potential driver for development of right-sided CRC.

Pharmaceutical Compositions

In certain embodiments, the present invention provides for a pharmaceutical composition comprising an antimicrobial agent or probiotic agent of the present invention. The antimicrobial agent or probiotic agent can be suitably formulated and introduced into a subject or the environment of the cell by any means recognized for such delivery.

Such compositions typically include the agent and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in a selected solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For a compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of an antibiotic agent and/or a probiotic agent for preventing formation and/or reducing the size of a biofilm in a subject (i.e., an effective dosage) depends upon the antibiotic agent and/or probiotic agent selected. For instance, single dose amounts of an antibiotic agent in the range of approximately 1 pg to 1000 mg may be administered; in some embodiments, 10, 30, 100, or 1000 pg, or 10, 30, 100, or 1000 ng, or 10, 30, 100, or 1000 µg, or 10, 30, 100, or 1000 mg may be administered. In some embodiments, 1-5 g of the compositions can be administered. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of an antibiotic agent and/or a probiotic agent can include a single treatment or, preferably, can include a series of treatments.

Suitable amounts of an antibiotic agent and/or a probiotic agent must be introduced and these amounts can be empirically determined using standard methods. Exemplary effective concentrations of individual antibiotic agents and/or probiotic agents in the gut of a subject can be 500 millimolar or less, 50 millimolar or less, 10 millimolar or less, 1 millimolar or less, 500 nanomolar or less, 50 nanomolar or less, 10 nanomolar or less, or even compositions in which concentrations of 1 nanomolar or less can be used.

The pharmaceutical compositions can be included in a kit, container, pack, or dispenser together with instructions for administration.

Cancer Therapies

Currently available therapies and their dosages, routes of administration and recommended usage are known in the art and have been described in such literature as the Physician's Desk Reference (60th ed., 2006). Routes of administration include parenterally, intravenously, subcutaneously, intracranially, intrahepatically, intranodally, intraureterally, subureterally, subcutaneously, and intraperitoneally.

Dosage

Dosage of one or more antibiotic, probiotic, or, optionally, other cancer therapy agents of the invention can be determined by one of skill in the art and can also be adjusted by the individual physician in the event of any complication. Typically, the dosage ranges from 0.001 mg/kg body weight to 5 g kg body weight. In some embodiments, the dosage range is from 0.001 mg/kg body weight to 1 g kg body weight, from 0.001 mg kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 g/kg body weight to 30 g/kg body weight. Alternatively, the dose range will be titrated to maintain serum levels between 5 g/mL and 30 g/mL.

Administration of the doses recited above can be repeated for a limited period of time. In some embodiments, the doses are given once a day, or multiple times a day, for example but not limited to three times a day. In one embodiment, the doses recited above are administered daily for several weeks or months. The duration of treatment depends upon the subject's clinical progress and responsiveness to therapy, e.g., shrinkage of tumor sizes. Continuous, relatively low maintenance doses are contemplated after an initial higher therapeutic dose.

Efficacy testing can be performed during the course of treatment using the methods described herein, e.g., ultrasound, MRI and CT to monitor the shrinkage in size of the tumors in the treated subject. A decrease in size of the tumors during and after treatment indicates that the treatment is effective in reducing tumor size. Measurements of the degree of severity of a number of symptoms associated with cancerous tumors are also noted prior to the start of a treatment and then at later specific time period after the start of the treatment. A skilled physician will be able to ascertain the tumor sizes and related symptoms by known methods in the art and those described herein.

Combination Therapies

In a specific embodiment, cycling therapy involves the administration of a first cancer therapeutic for a period of time, followed by the administration of a second cancer therapeutic for a period of time, optionally, optionally followed by the administration of a third cancer therapeutic for a period of time and so forth, and repeating this sequential administration, i.e., the cycle in order to reduce the development of resistance to one of the cancer therapeutics, to avoid or reduce the side effects of one of the cancer therapeutics, and/or to improve the efficacy of the cancer therapeutics.

When two therapeutically effective regimens are administered to a subject concurrently, the term "concurrently" is not limited to the administration of the cancer therapeutics at exactly the same time, but rather, it is meant that they are administered to a subject in a sequence and within a time interval such that they can act together (e.g., synergistically to provide an increased benefit than if they were administered otherwise). When two prophylactically effective regimens are administered to a subject concurrently, the term "concurrently" is not limited to the administration of the cancer therapeutics at exactly the same time, but rather, it is meant that they are administered to a subject in a sequence and within a time interval such that they can act together (e.g., synergistically to provide an increased benefit than if they were administered otherwise). For example, the cancer therapeutics may be administered at the same time or sequentially in any order at different points in time; however, if not administered at the same time, they should be administered sufficiently close in time so as to provide the desired therapeutic effect, preferably in a synergistic fashion. The combination cancer therapeutics can be administered separately, in any appropriate form and by any suitable route. When the components of the combination cancer therapeutics are not administered in the same pharmaceutical composition, it is understood that they can be administered in any order to a subject in need thereof. For example, a first therapeutically effective regimen can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second cancer therapeutic, to a subject in need thereof. In another embodiment, a first prophylactically effective regimen can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second cancer therapeutic, to a subject in need thereof. In various embodiments, the cancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the cancer therapeutics are administered within the same office visit. In another embodiment, the combination cancer therapeutics are administered at 1 minute to 24 hours apart.

In a specific embodiment, the combination therapies have the same mechanism of action. In another specific embodiment, the combination therapies each have a different mechanism of action.

Methods of Treatment

The present invention provides for both prophylactic and therapeutic methods of treating a subject at risk of (or susceptible to) a neoplastic disease or disorder.

"Treatment", or "treating" as used herein, is defined as the application or administration of a therapeutic agent (e.g., an antibacterial agent) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., an antibacterial agent). Subjects at risk for the disease can be identified by, for example, one or a combination of diagnostic or prognostic assays as described herein, particularly those described herein related to biofilm detection within a subject. Administration of a prophylactic agent can occur prior to the detection of, e.g., cancer in a subject, or the manifestation of symptoms characteristic of the disease or disorder, such that the disease or disorder is prevented or, alternatively, delayed in its progression.

Another aspect of the invention pertains to methods of treating subjects therapeutically, i.e., altering the onset of symptoms of the disease or disorder. These methods can be performed in vitro (e.g., by culturing the cell with the agent(s)) or, alternatively, in vivo (e.g., by administering the agent(s) to a subject).

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment according to that individual's drug response genotype, expression profile, biomarkers, etc. Pharmacogenomics allows a clinician or physician to target prophylactic or therapeutic treatments to patients who will most benefit from the treatment and to avoid treatment of patients who will experience toxic drug-related side effects.

Therapeutic agents can be tested in a selected animal model. For example, an antibiotic agent as described herein can be used in an animal model to determine the efficacy, toxicity, or side effects of treatment with said agent. Alternatively, an agent (e.g., a therapeutic agent) can be used in an animal model to determine the mechanism of action of such an agent.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C.

Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (Danio rerio), (4th Ed., Univ. of Oregon Press, Eugene, 2000).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

The present invention is described by reference to the following Examples, which are offered by way of illustration and are not intended to limit the invention in any manner. Standard techniques well known in the art or the techniques specifically described below were utilized.

Example 1: Materials and Methods

Patient Selection/Sample Acquisition

CRC and paired normal tissue were collected from patients undergoing surgery at Johns Hopkins Hospital. All tissue not needed for pathologic diagnosis was rapidly preserved in formalin, Carnoy's solution and RNAlater for analysis. Patients who received pre-operative radiation and/or chemotherapy or with a personal history of CRC were excluded. For patients in this study, two bowel preparations were routinely used and recorded (mechanical bowel preparation [Miralax™], or Fleet Phospo-Soda™ enema), Preoperative intravenous antibiotics were administered in all cases (cefotetan or clindamycin/gentamycin). No patient received pre-operative oral antibiotics.

Healthy control patients undergoing screening colonoscopy or colonoscopy for diagnostic work-up (eg, anemia) were recruited and signed informed consent. All patients underwent a standard mechanical bowel preparation (FIGS. 10A-C). Mucosal biopsies from grossly normal colon were taken from the right (cecum or ascending) and left (descending or sigmoid) colon during the colonoscopy. All tissue was rapidly preserved in formalin, Carnoys solution and/or RNAlater for analysis. Patients who had a personal history of CRC, inflammatory bowel disease or were treated with antibiotics within the past three months were excluded.

Fluorescent In Situ Hybridization (FISH)

Oligonucleotide probes were synthesized and conjugated at the 5' end to the fluorophore Cy3, Alexa 405, Alexa 488, Oregon Green 514, Alexa 514, Alexa 555, Rhodamine Red X, Texas Red X, Alexa 633 or Alexa 647 (Invitrogen Life Technologies). Twelve probes were applied to 5 µm thick Carnoy's solution-fixed paraffin-embedded tissue sections (FIG. 11; 18-28). All samples collected were also stained with the Eub338 universal bacterial probe to detect all bacteria present on the sample. The appropriate nonsense probe was also applied to test for nonspecific binding of probes. Successive sections were stained with Periodic acid Schiff (PAS) to confirm mucus presence and preservation.

Samples that were determined to have a bacterial presence by universal probe were next analyzed using group and species specific probes (FIG. 11).

Slides were de-waxed following standard procedures. Probes were applied to slides at a concentration of 2 pmol/ul in prewarmed hybridization buffer (900 mM NaCl, 20 mM Tris pH 7.5, 0.01% SDS, 20% formamide). Slides were incubated at 46° C. in a humid chamber for 2 hours, and washed at 48° C. for 15 minutes in wash buffer (215 mM NaCl, 20 mM Tris pH 7.5, 5 mM EDTA). Slides were dipped in water, then in 100% ethanol, air-dried, and coverslips were mounted using ProLong Gold antifade reagent (Life Technologies).

Biofilm Bacterial Quantification

Biofilm bacterial density and depth were measured using slides hybridized with the universal bacterial probe, Eub338, and imaged at 1000× magnification with a Nikon E800 microscope and Nikon NIS elements viewing software.

Measures of bacterial density were based on the following model. A 10×10 µm square placed over a region of a 5 µm thick tissue section (500 µm$^3$) constituted a volume of $5 \times 10^{-10}$ ml. One bacterium in this volume was equivalent to $2 \times 10^9$ bacteria/ml. The visual distinction of a single bacterium was lost but spaces could still be seen between the bacteria when 250 bacteria occupied a 10×10 µm space; these cases were assigned a concentration of $10^{11}$ bacteria/ml. A solid mat of bacteria with no discernible spaces between the bacteria constituted an increase to 2500 bacteria in a 10×10 µm space; these cases were assigned a concentration of $10^{12}$ bacteria/ml (29). The mean of five (10×10 µm) fields was used to determine bacterial density.

The biofilm depth was measured using ImageJ software calibrated with an image of a stage micrometer from the same microscope and magnification used in the images being quantified. Biofilm depth was calculated as the mean of five measurements taken along a 200 µm span of the biofilm.

Scanning Electron Microscopy (SEM)

Tissue samples were fixed in 2% glutaraldehyde, 2% paraformaldehyde in 0.1 M sodium cacodylate (NaCaco), 3 mM CaCl, 1% sucrose pH 7.4 overnight with gentle rocking. Samples were rinsed three times in washing buffer (0.1 M NaCaco, 3 mM CaCl, 3% sucrose), and placed in 1% osmium tetroxide in 1 M NaCaco for 1 hour in the dark. Samples were rinsed twice in distilled water followed by dehydration in an ethanol series. Samples were next placed in a 1:1 mixture of 100% ethanol to hexamethyldisilazane (HMDS) for two washes of 10 minutes each. This was followed by three washes with 100% HMDS for five minutes each. Samples were then removed and placed in a vacuum desiccant overnight followed by gold palladium coating before viewing under a Leo Zeiss Field emission SEM. Samples were scored by two independent observers (CMD, CLS) for biofilm presence and morphologies.

Spectral Imaging and Unmixing

Spectral images were acquired with a Zeiss LSM 780 laser scanning confocal microscope with a 32-channel GaAsP detector and Zeiss Zen software. All images were acquired with a Zeiss Plan-Apochromat 40×/1.4 NA(420762-9900) objective; 2× line averaging, 2048×2048px frame size, 1.58 us pixel dwell time; and 8.7 nm spectral resolution. Five fields of view were selected per sample. Spectral images of each field of view were acquired sequentially with six different lasers proceeding from long to short excitation wavelength: HeNe633 (633 nm), HeNe594 (594 nm), DPSS561-10 (561 nm), Ar514 (514 nm), Ar488 (488 nm), and Diode 405-30 (405 nm).

FISH probe reference spectra were measured from spectral images of pure populations of cultured bacterial cells singly labeled with the appropriate taxon-specific FISH probe. Tissue autofluorescence reference spectra were measured from spectral images of tissue subjected to the FISH procedure but without probe, and imaged under experimental imaging conditions.

Linear unmixing was performed with a custom Mathematica script using a least squares method. Each spectral image was unmixed independently using the appropriate reference spectra for the excitation wavelength. For each field of view, unmixed channels for each FISH probe were extracted from the unmixing results corresponding to the appropriate excitation wavelength. Extracted unmixed channels were compiled and colorized in ImageJ using the Image5D plugin.

Sample Preparation for Sequencing

Mucosal samples from tumor, surgical distal normal flanking tissues, and colonoscopy biopsies were collected in the pathology suite and immediately placed in RNAlater (Qiagen Inc. Germantown, Md.) and stored at −80° C. Tissue samples (100-500 mg) were placed in a 15 ml conical tube with 2.5 ml Qiagen buffer ASL. Samples were incubated at 95° C. for 15 minutes with frequent vortexing to remove bacteria from the epithelial surface. Following the dislodging of mucosal associated bacteria, 1.4 ml of supernatant was removed and cells were thoroughly lysed using a Barocycler NEP2320 (Pressure Biosciences, Inc. South Easton, Mass.), by cycling between atmospheric pressure, 0 psi to 25,000 psi while maintaining a temperature of 60° C. Following pressure lysis DNA was extracted using the QIAamp DNA Stool Kit (Qiagen). Recovered genomic DNAs were quantitated using a Nanodrop spectrophotometer (Bio-Rad Life Science Research, Hercules, Calif.). The V3-V5 region of bacterial 16S rDNA was amplified and sequenced following the procedures described by the Human Microbiome Project standard protocol (http://www.hmpdacc.org/doc/16S_Sequencing_SOP_4.2.2.pdf).

Briefly, the V3-V5 region of 16S rDNA was amplified with PCR primers (357F 5' CCTACGGGAGGCAGCAG 3' and 926R 5' CCGTCAATTCMTTTRAGT 3') that were appended with Roche 454 Titanium FLX library adapter sequences. All B-adapter primers were identical, while A-adapter primers also contained a unique barcode of 5-10 nucleotides to allow indexing of individual samples. Each sample was PCR amplified for 30 cycles with Phusion HF DNA polymerase (New England Biolabs Inc. Ipswich, Mass.). PCR products were purified by gel electrophoresis. Bands of the appropriate size were excised from the gel and purified using the QIAquick Gel Extraction Kit (Qiagen Inc. Germantown, Md.). Purified DNAs were quantified using the 454 FLX Library Quantification Kit (KAPA Biosystems Inc. Woburn, Mass.) and pooled for sequencing in equal molar quantity.

Sequence Data Analysis

Raw sequence reads were initially assigned to samples based on multiplex identifier barcodes, trimmed of forward and reverse primer sequences, and filtered for quality and length (minimum 150 bp) using the QIIME package (v1.6.0; 30, 31). High quality reads were then organized by sample and error-corrected using the Acacia tool (v1.52; 32), and subsequently screened for chimeras utilizing de novo UCHIME (v4.2.40; 33). Chloroplast DNA was identified and removed using the RDP Bayesian classifier (v2.5; 34).

The final high-quality contaminant-free dataset was then submitted to the CloVR-16S pipeline (v1.1; 35) for diversity estimation, taxonomic characterization and comparative analysis of sample groups of interest. The CloVR-16S protocol utilized the RDP Bayesian classifier (34), QIIME (30), and Mothur (36) software tools, producing a wide array of standardized outputs for researchers to use in post-processing and downstream analysis. Analyses included clustering of sequences into species-level OTUs (95% identity threshold), taxonomic assignment of OTU representatives and beta-diversity estimation. Pipeline runs were executed using CloVR (v2012.11.16) on the DIAG academic cloud (http://diagcomputing.org).

Tumor Molecular Testing

Tissue sections were reviewed by a pathologist and relevant tumor (KRAS, BRAF, MSI) and normal (MSI) areas were selected. DNA was extracted. KRAS and BRAF mutations were detected by PCR amplification and pyrosequencing (codons 12, 13, 61 of KRAS gene and exon 15 of BRAF gene). MSI was established by PCR amplification of 5 mononucleotide and 2 pentanucleotide microsatellite loci performed using the MSI Analysis System, (Promega Corp. Madison, Wis.). Amplification products were analyzed by capillary electrophoresis.

Immunohistochemistry

Immunohistochemistry was performed on tissue fixed in 10% formalin and paraffin-embedded following standard procedures. Sections were de-paraffinized and rehydrated through a xylene, ethanol-water gradient. Ki67 and H2AX staining were performed on an automated immunostainer Benchmark ST Staining System using detection reagents from the iView DAB detection kit (Roche) with either Ki67 monoclonal antibody (clone 30-9, Roche) or H2AX polyclonal antibody (clone JBW301, EMD Millipore). The TUNEL assay was performed per the manufacturer's instructions using the fluorescein in situ cell death detection kit (Roche). Slides were de-paraffinized and pretreated with proteinase K for 15 minutes at 37° C. Working strength TdT enzyme and labeling solution was applied for 1 hour at 37° C. in a humidified chamber. After washing with PBS, DAPI was applied for 10 minutes. Slides were washed with PBS and mounted with glass coverslips using Prolong Gold antifade reagent (Life Technologies).

Quantification of Proliferation and Apoptosis

Figure 3C:
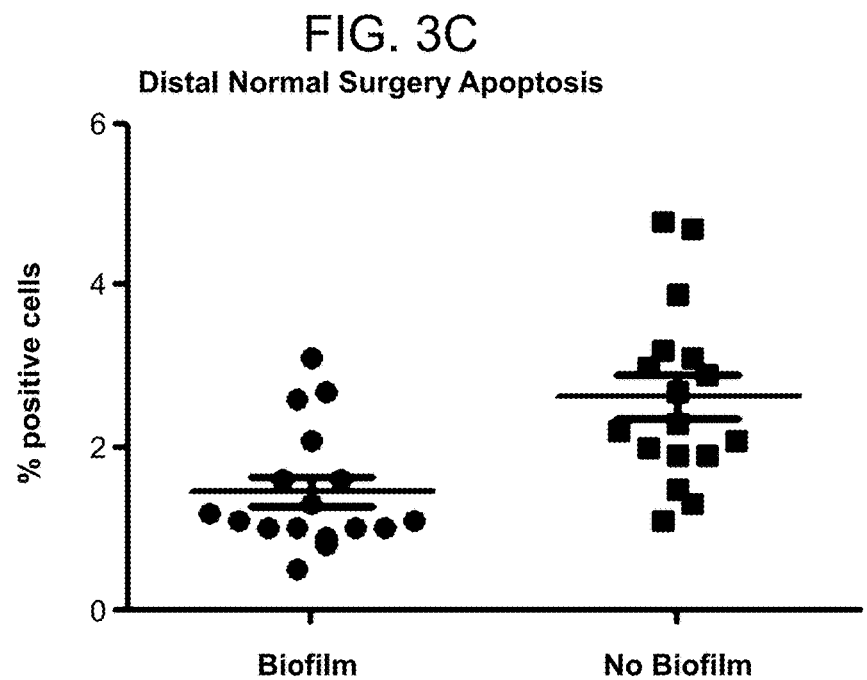
Figure 3D:
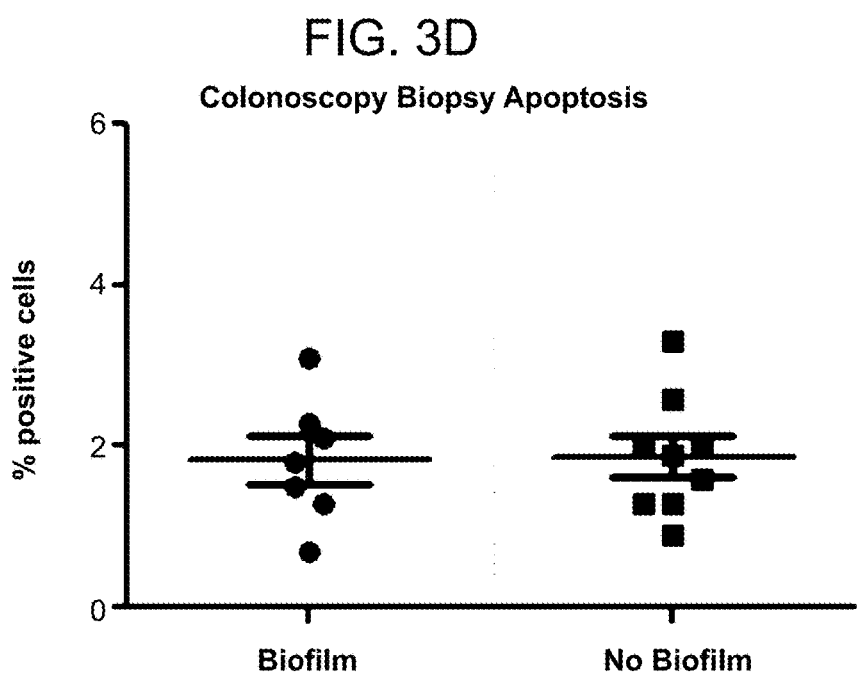

A total of 5 well-oriented crypts were selected from each sample to be scored for Ki67+ cells by two blinded individuals. Positive cells were counted on both sides of each crypt starting at the base and ending at the luminal surface in increments of 15 cells (FIG. 3). Each interval was scored as cells positive per 15 cells. The mean number of proliferating cells within each interval was calculated for each analyzed sample, groups were compared using the nonparametric Mann Whitney U test.

Apoptosis scoring was performed by two independent observers. TUNEL positive cells were counted per 1000 epithelial cells in 10 randomly selected fields. Results were graphed as percent positive and groups were compared using the nonparametric Mann Whitney U test.

Statistical Analysis

Prior to downstream statistical analysis, sequence data were subsampled to equivalent depths (2500 sequences per sample). Unweighted UniFrac distances, and principal coordinate analysis plots were computed in QIIME. Additional statistical analyses were performed in R (v2.15.1) and included paired Student's T test, Fisher's exact test and the nonparametric Mann Whitney U test as appropriate.

Example 2: Identification of Microbial Biofilms Associated with Colorectal Tumors (CRC & Adenomas Examined)

The microbial communities associated with surgically-resected colorectal tumors (CRC and adenomas) and paired normal tissue collected from the pathologically tumor-free mucosa at the surgical resection margin were systematically examined. Paired normal colon tissues were obtained from the margin of the resected specimens furthest from the site of the tumor (FIG. 4). In addition, as a healthy control population, colon biopsies obtained from individuals without colorectal tumors and without a diagnosis of inflammatory colonic disease undergoing routine screening colonoscopy were studied. FIGS. 9 and 10A-C present all patient metadata.

Figure 1B:
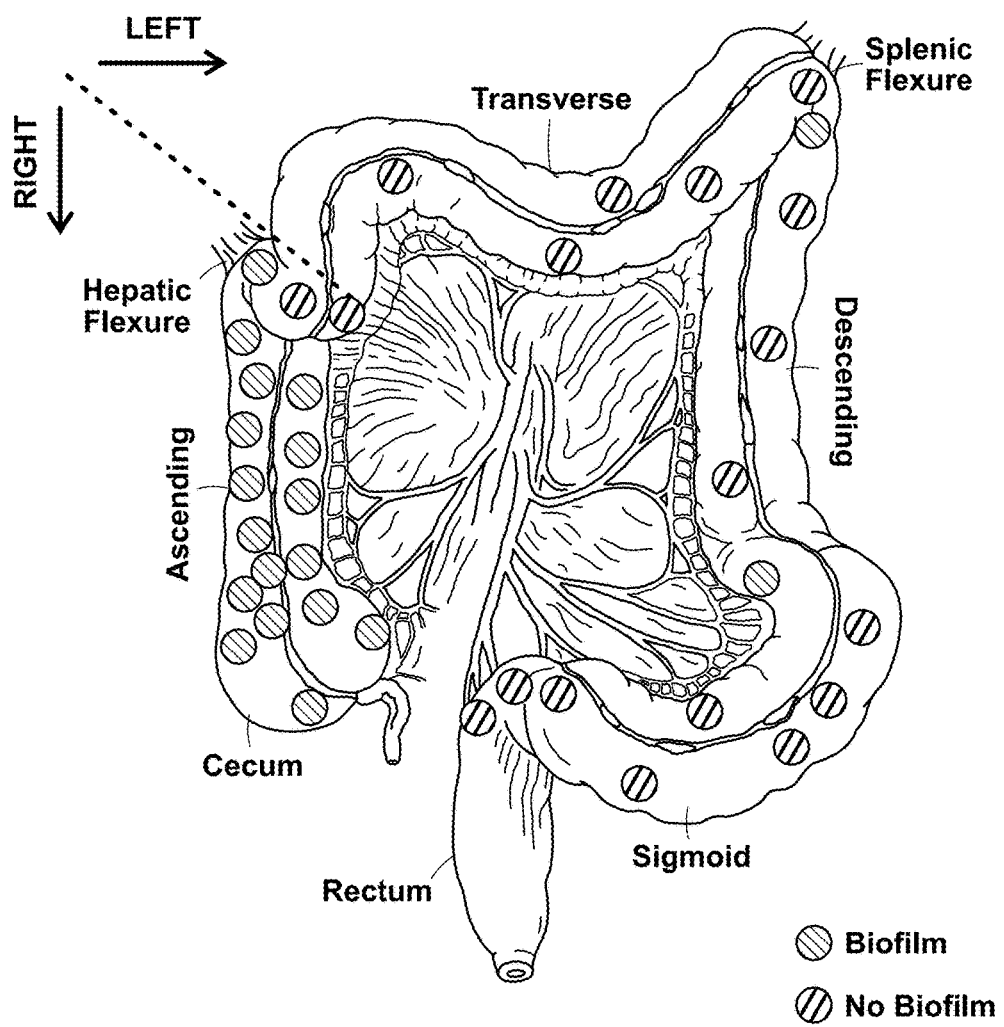
Figure 1C:
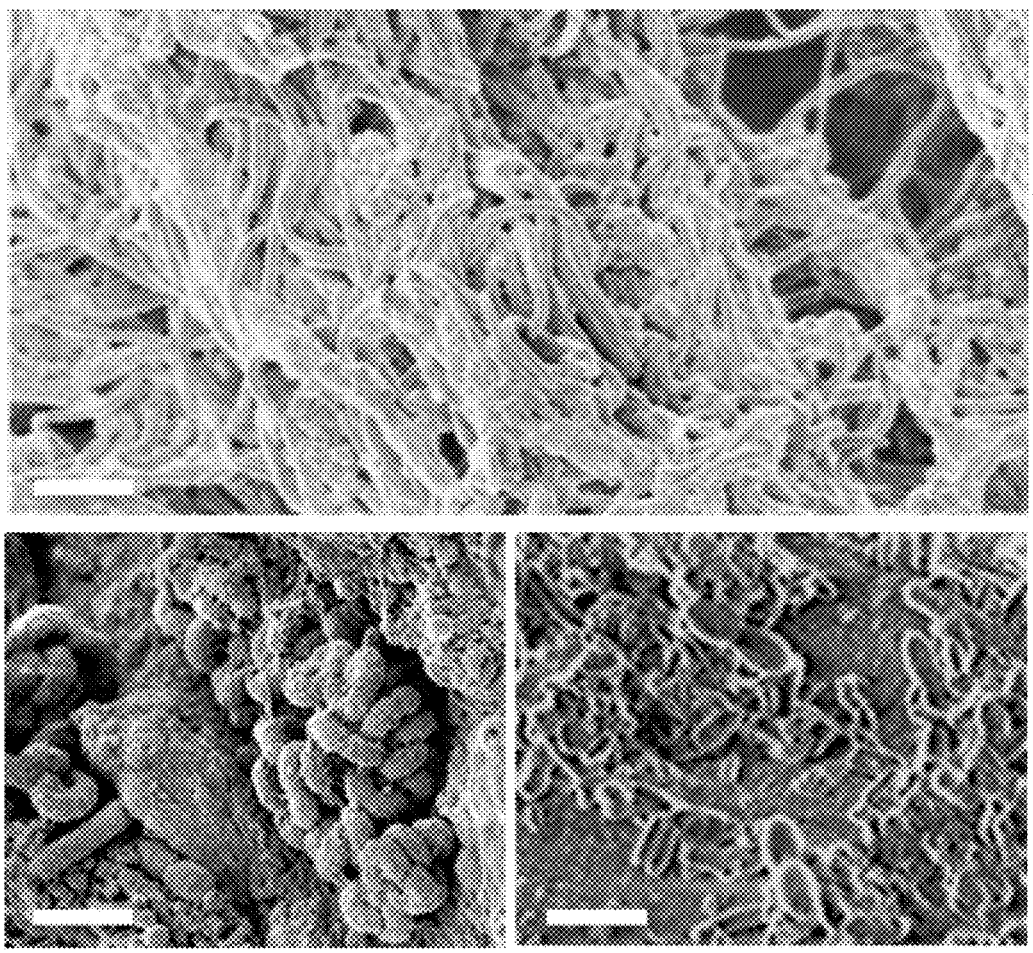
Figure 5:
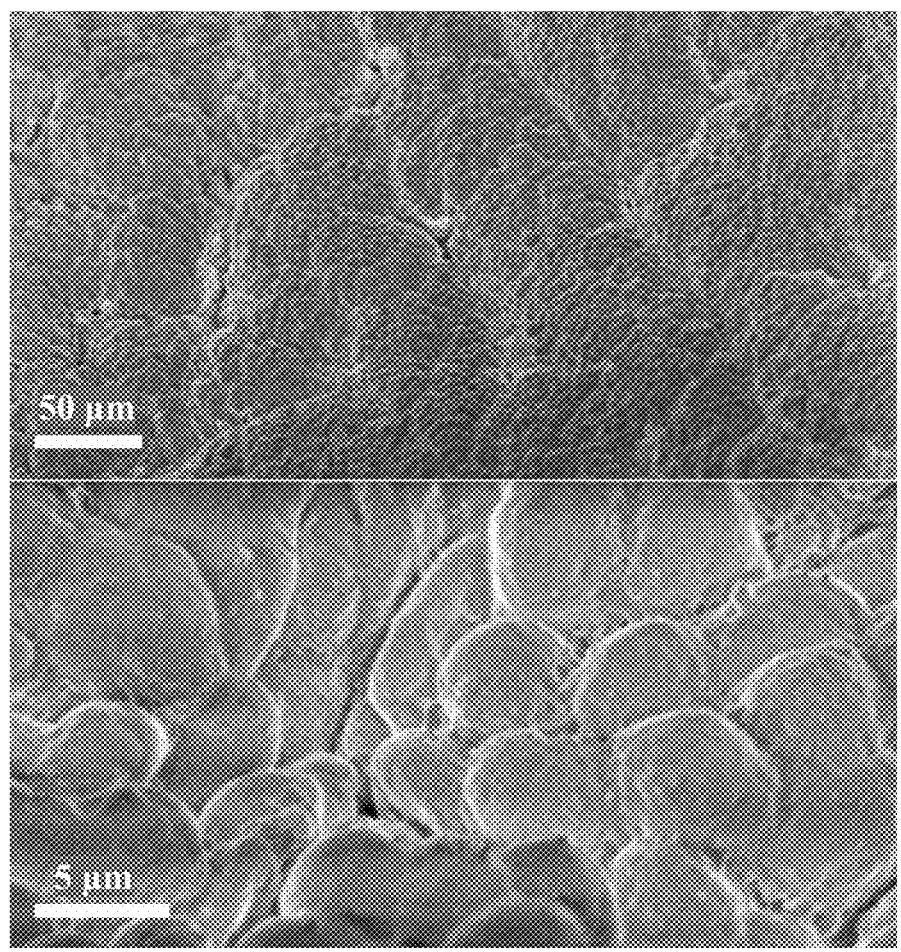
FIG. 5 displays representative scanning electron micrographs of a left CRC devoid of any bacterial presence (no biofilm), presented at two magnifications.

The spatial relationship of the microbiota was first compared with the host mucus layer and colonic epithelium using fluorescent in situ hybridization (FISH). Carnoy's solution-fixed, paraffin-embedded tissues known to preserve the mucus layer were employed. To detect all bacterial populations, the tissues were hybridized with the Eub338 probe, which targeted the conserved 16S ribosomal RNA bacterial domain (4). Bacterial biofilms were defined as massive bacterial invasion (>109 bacteria/ml) of the mucus layer spanning at least a linear distance of 200 μm of the epithelial surface. On overall tumor samples, bacterial biofilms were identified by FISH analysis on 48% (15/31) and 67% (4/6) of all evaluated CRCs and adenomas, respectively (FIG. 1A). Bacterial biofilm presence on tumors was ordered by geographical location along the colon axis. Namely, tumors in the right ascending colon (including the hepatic flexure) were biofilm-positive in 87% (13/15) and 100% (4/4) of CRCs and adenomas, respectively, whereas tumors located in the transverse and descending colon displayed biofilms in 13% (2/16) and 0% (0/2) of CRCs and adenomas, respectively (P<0.0001 and P=0.067 vs ascending colon CRCs and adenomas, respectively; FIG. 1B). Biofilm formation was not associated with age, gender, race, CRC stage, tumor size, bowel preparation or histopathologic classification (all P>0.05). Scanning electron microscopy (SEM) of a tumor sample subset was consistent with the FISH results, revealing both direct bacterial:epithelial surface contact and a dense biofilm comprised of mixed bacterial morphologies on all ascending colon tumors with limited mucosal bacteria detected on tumors distal to the hepatic flexure (FIG. 1C, top and bottom, FIG. 5). These data further confirmed that a breach of the colonic protective mucus layer was strikingly dictated by geographic location. Embryologic development has often been used to define the right colon as comprised of the cecum through the transverse colon and the left colon as the splenic flexure distal to the rectum. However, based on the discrete anatomical distribution of biofilms and colon tumors identified, right colon cancer was defined as proximal to the hepatic flexure and left colon cancer was defined as distal to the hepatic flexure (FIG. 1B).

Figure 1D:
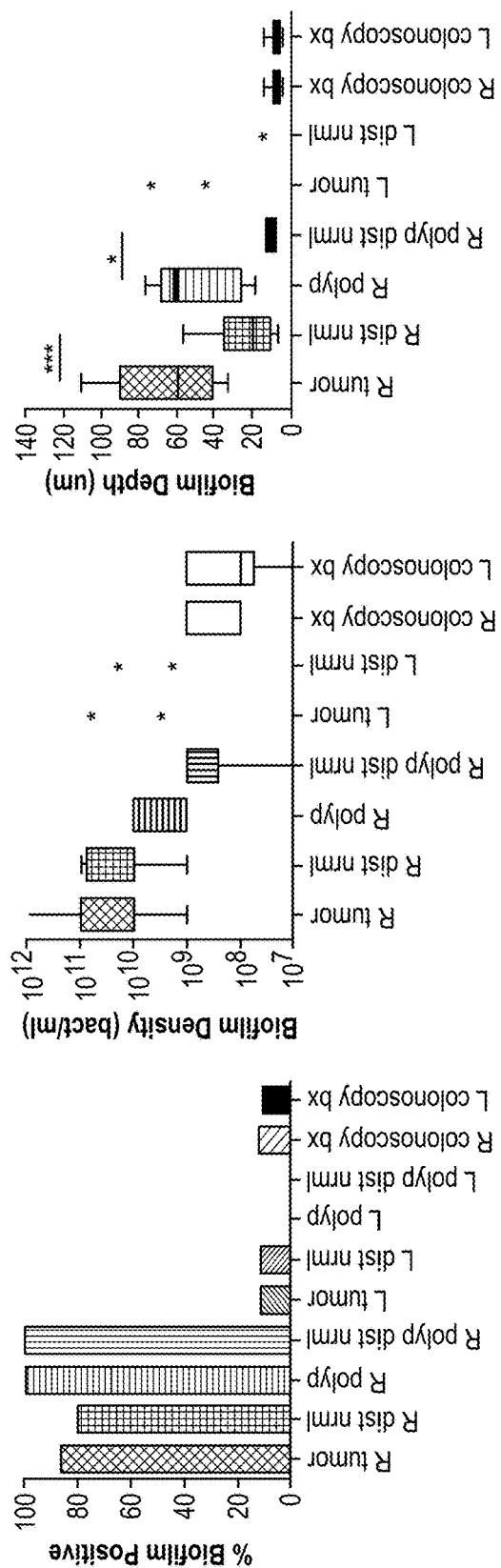

Example 3: Characterization of Microbial Biofilms Associated with Colorectal Tumors To determine if biofilm formation was specific for the tumor microenvironment, we next used FISH to examine the paired pathologically normal colon tissues obtained from the surgical resection margin most distal from the tumor mass (FIG. 4) for biofilm formation. No biofilms were detected on the distal pathologically normal surgically-resected colon tissues paired with biofilm-negative tumors (adenomas and CRCs). In surprising contrast, all but one distal pathologically normal surgically-resected colon tissue paired with a biofilm-covered tumor were biofilm positive whether in the right or left colon; thus, 93% (14/15) and 100% (4/4) of paired pathologically normal colon tissues from the surgical resection margin of biofilm-covered CRCs and adenomas, respectively, were biofilm positive (FIGS. 1A and 1D). Of note, the single surgically-resected distal normal tissue on which we failed to detect a biofilm was fixed in formalin rather than Carnoy's and thus not optimized for mucus preservation (5). The depth, but not the bacterial density, of biofilms present on surgically-resected distal normal colon tissues was usually less than its corresponding biofilm-covered tumor (FIG. 1D). These findings demonstrate that biofilm formation represents a broad regional alteration in host epithelial:microbiota association not restricted to tumor tissue. By comparison, however, screening colonoscopy biopsies from healthy individuals were typically covered with a mucus layer devoid of bacterial presence (FIG. 1A). A subset of colonoscopy biopsies (15/120, 13%) revealed thin bacterial biofilms with an average density of 108 bacteria/ml. Biofilm formation on colonoscopy biopsy tissues did not differ by colon location (8/60, right colon vs. 7/60, left colon) (FIG. 1D). Thus, the right colon does not have a greater likelihood of bacterial biofilm development in a cancer-free host. These findings in the healthy host were consistent with previous reports that detected biofilms on ~15% of biopsies from asymptomatic individuals without colon geographic preference (6).

Figure 2A:
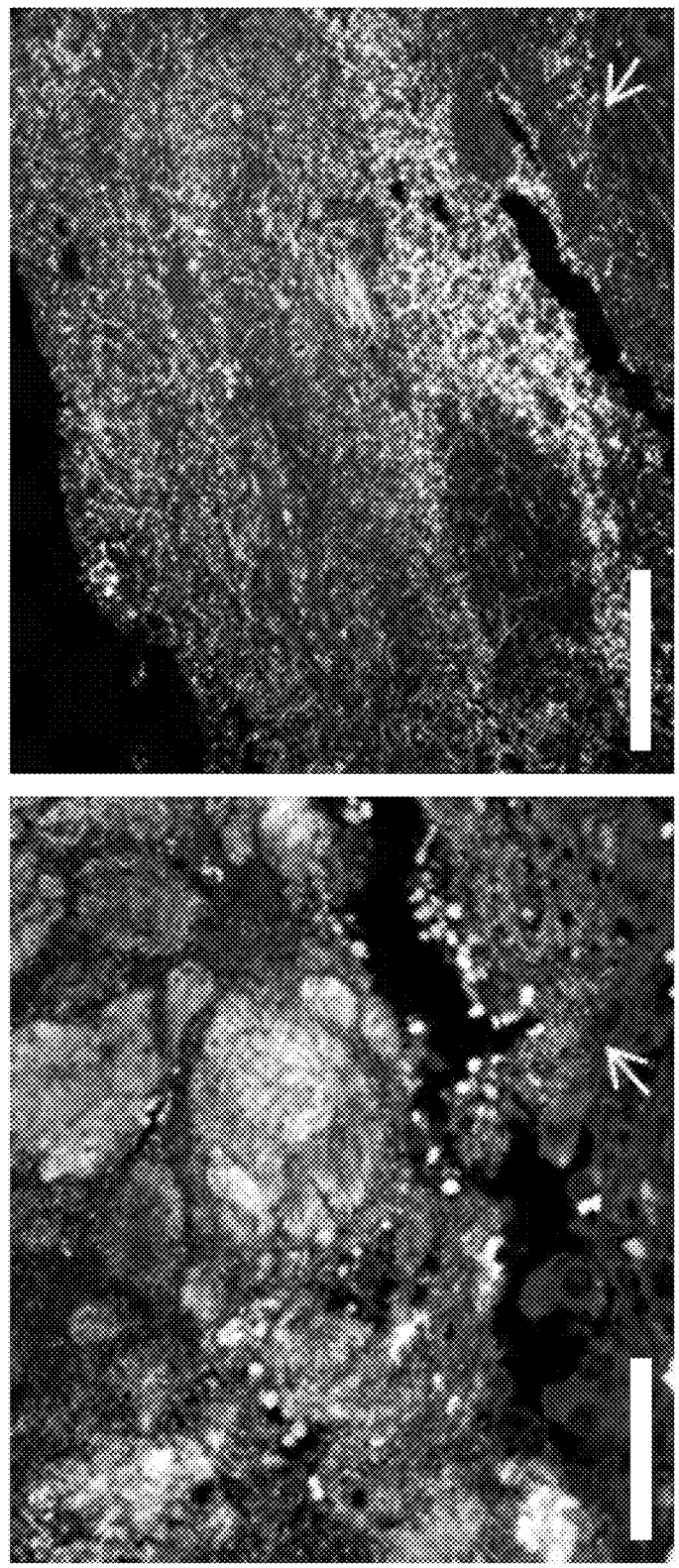
Figure 2D:
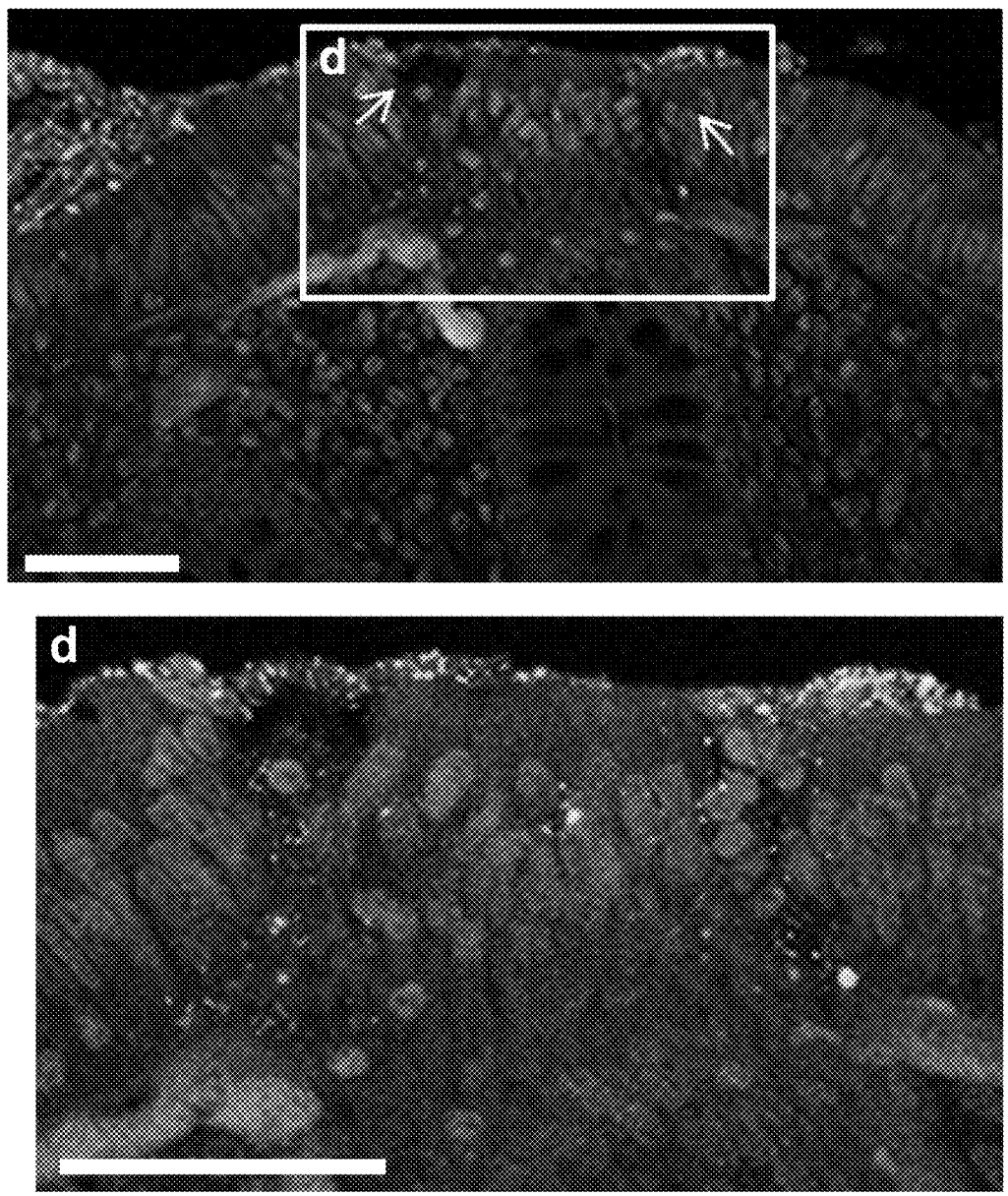
Figure 6A:
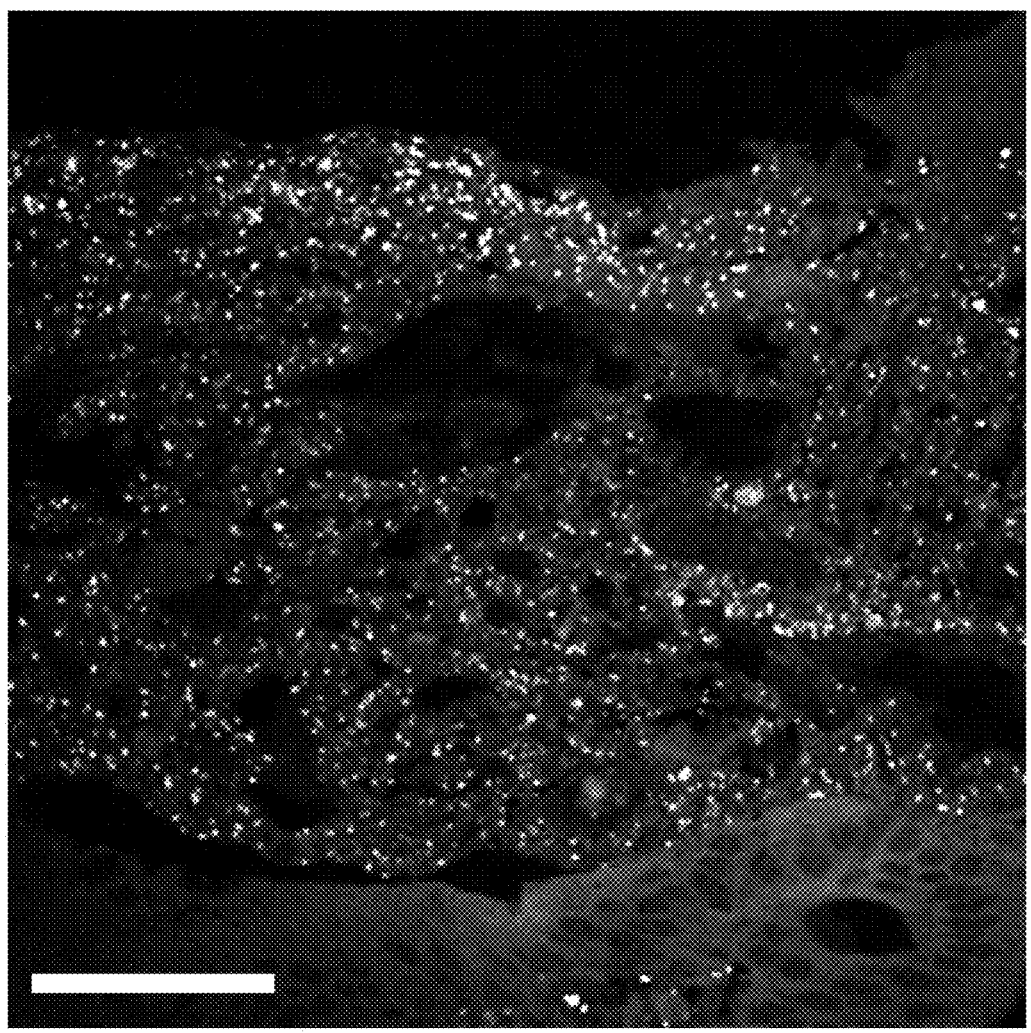
FIGS. 6A-6C show that bacterial biofilms detected on CRCs and adenomas had variable compositions (indeed, a range of biofilm bacterial community compositions).
Figure 6B:
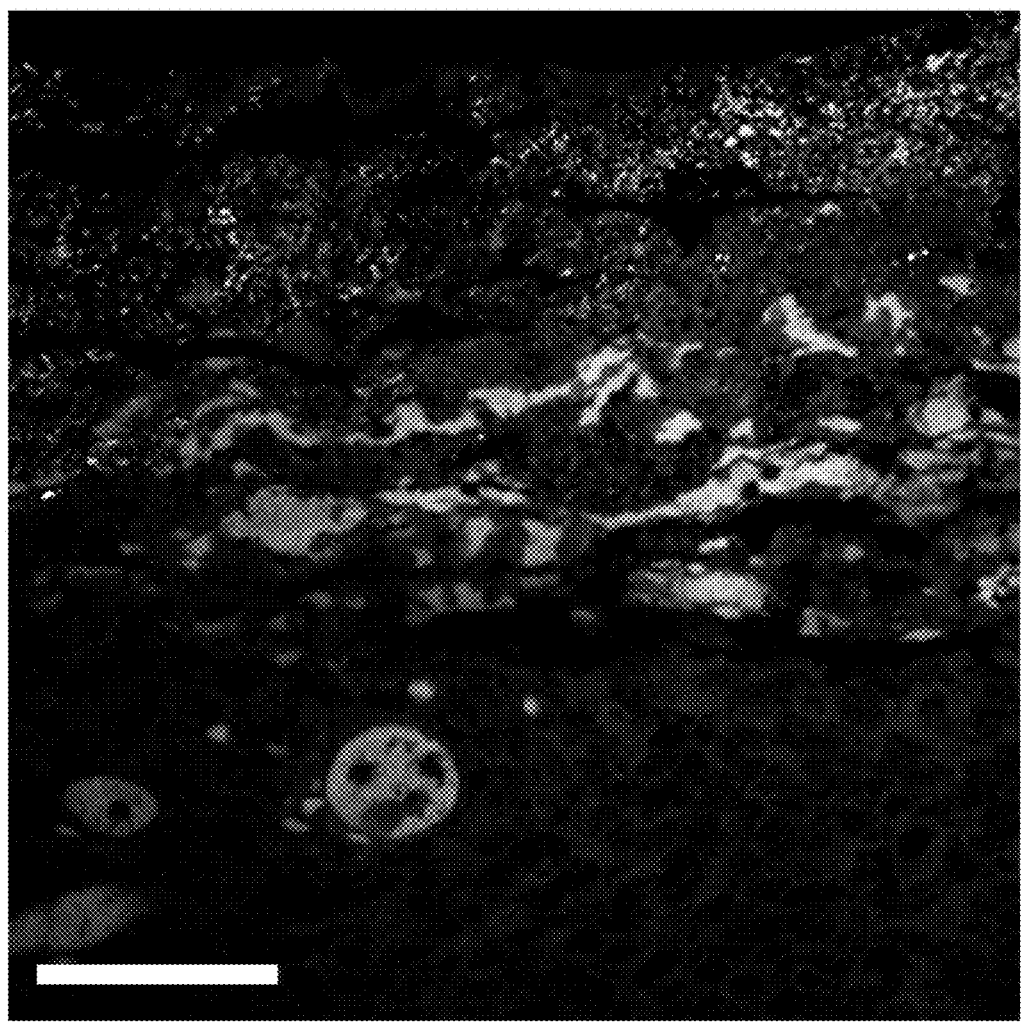
Figure 6C:
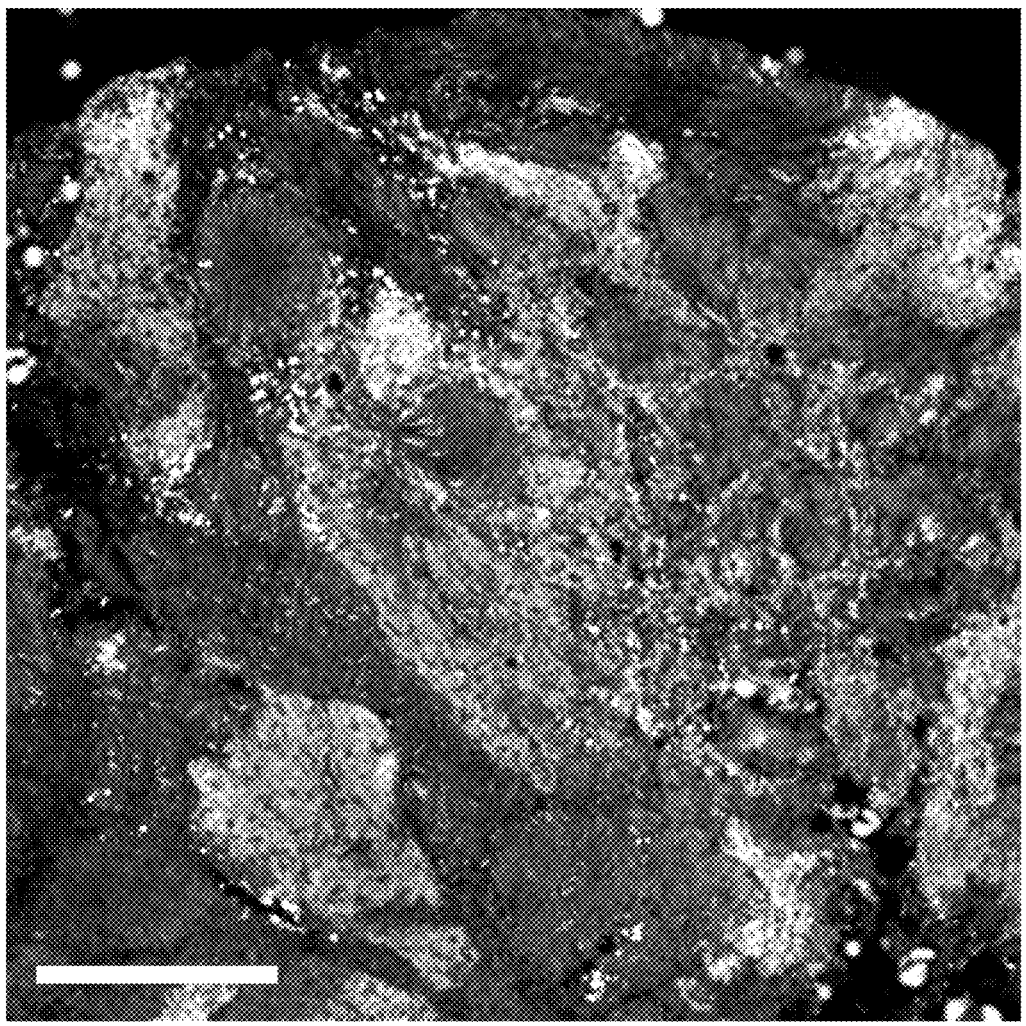

The composition and spatial organization of specific bacteria within the biofilms was then evaluated using fluorescence spectral imaging employing eleven group- and species-specific FISH probes (FIG. 11). Combinations of nine probes were selected for simultaneous hybridization to the tissues. Sixteen biofilm-covered tumors (3 adenomas from 2 patients, 13 CRCs) and their paired surgically-resected distal normal mucosa were available for analysis along with 5 right and 4 left colonoscopy biopsies (3 of which were paired R/L sets). All biofilms, whether associated with normal colon mucosa (surgically-resected distal pathologically normal or colonoscopy biopsies) or tumor tissue, were polymicrobial (FIGS. 2A-C). Predominant bacterial phyla associated with adenomas and CRCs were Bacteroidetes and Firmicutes (family Lachnospiraceae including *Clostridium, Ruminococcus*, and *Butyrivibrio*). A subset of tumors harbored predominant populations of Fusobacteria (4/16) or Gammaproteobacteria (1/16) (determined to be the Enterobacteriaceae family) (FIGS. 6A-6C). All biofilm-covered CRCs and adenomas exhibited bacterial invasion into the tumor mass (FIG. 2A white arrows) not detected in biofilm-negative tumors. The invasive bacterial groups were derived from the biofilm composition on the tumor surface. Biofilms identified on surgically-resected distal pathologically normal tissues were consistently diverse, comprised of Bacteroidetes, Lachnospiraceae, and Gammaproteobacteria (FIG. 2B). Biofilms detected on colonoscopy biopsies were similarly composed of Bacteroidetes and Lachnospiraceae (FIG. 2C). A subset of biofilm-positive surgically-resected distal normal mucosa (4/16) also revealed bacterial invasion into the colonic epithelial cells or submucosa (FIG. 2D). No colonoscopy biopsies with biofilms revealed invasive bacteria.

To further evaluate the colonic microbiota associated with CRCs and their paired surgically-resected distal normal tissues as well as colonoscopy biopsy tissues, high-throughput 454 pyrosequencing targeting the hypervariable V3-V5 region of the 16S ribosomal RNA gene was performed on DNA extracted from the mucosa of 23 CRCs, 2 adenomas and their paired surgically-resected distal normal tissues as well as 22 screening colonoscopy biopsies from healthy controls (11 right and left-matched pairs; FIGS. 12A-12D).

Figure 2E:
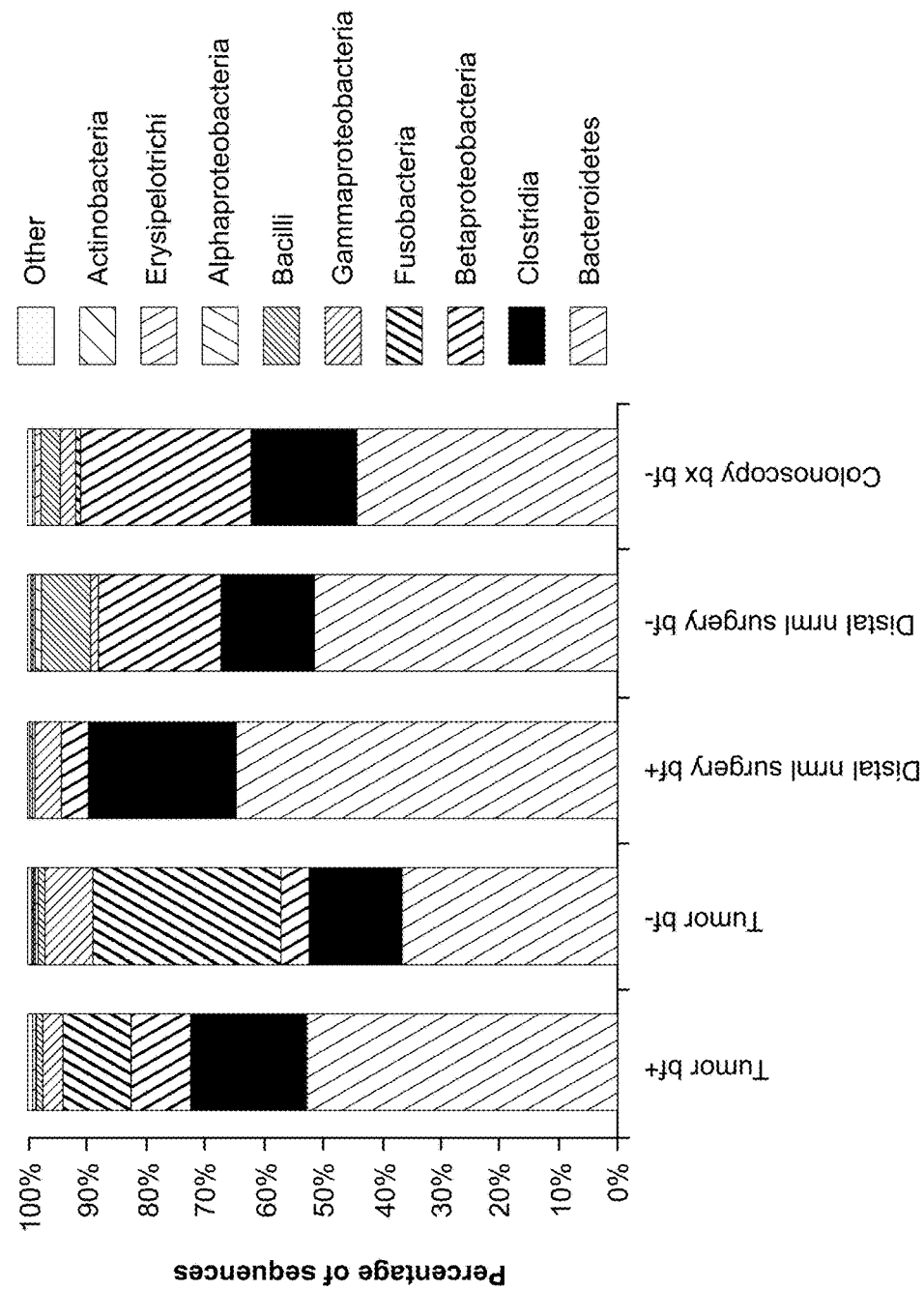
Figure 2F:
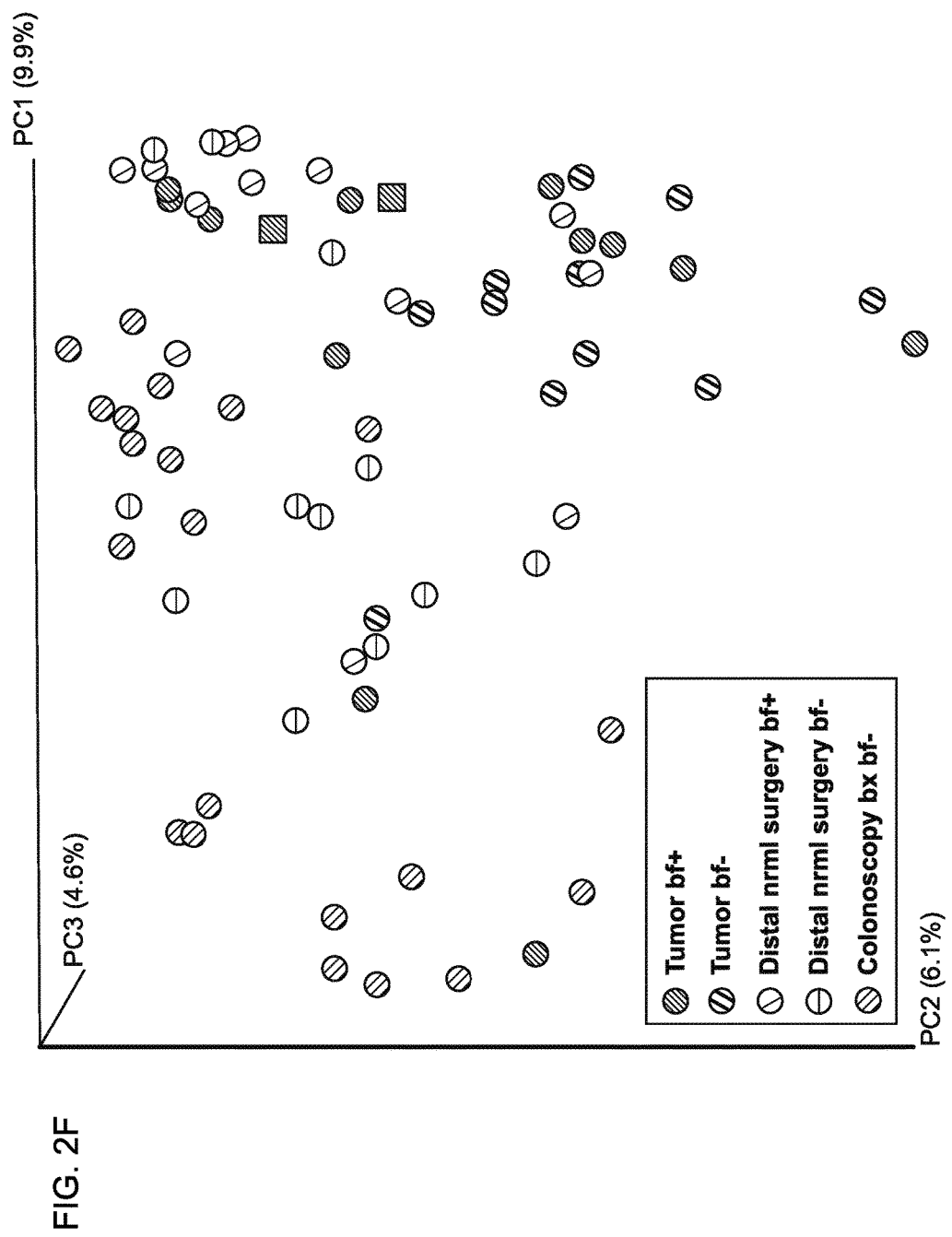
Figure 7:
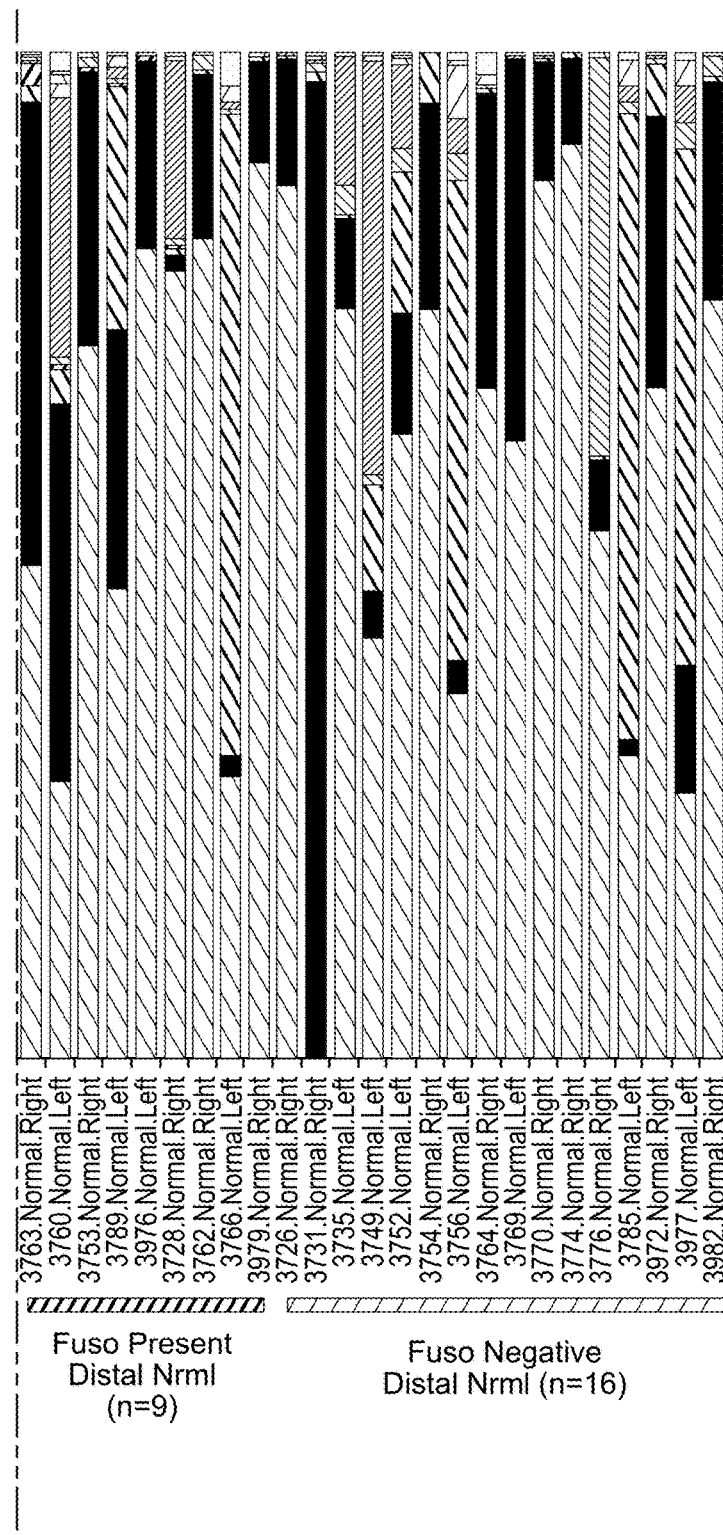
FIG. 7 shows that fusobacteria were not universally present on tumor tissues, but rather on a subset of CRCs, adenomas, paired surgically-resected distal normal tissues as well as colonoscopy control biopsies (fusobacteria profile presented as a histogram). Fusobacteria dominant tumors, defined as greater than 25% of total reads, made up 39% of all tumors screened (8/23 with a range of 30%-72%) (8). Nine tumors (9/23, 39%) were categorized as Fusobacteria present, defined as containing one or more reads assigned to Fusobacteria (ranging from 0.04-22% of total reads). Interestingly, neither adenoma was found to be Fusobacteria dominant; one adenoma was devoid of any Fusobacterial reads while the other contained just 2 reads (0.08% of total reads). No surgical distal normal tissues were Fusobacteria dominant, and nine (9/25, 36%) were found to be Fusobacteria present (ranging from 0.04%-2.4% of total reads). Fusobacteria were detected in 41% (9/22) of colonoscopy biopsies (ranging from 0.04%-8% of total reads).
Figure 7:
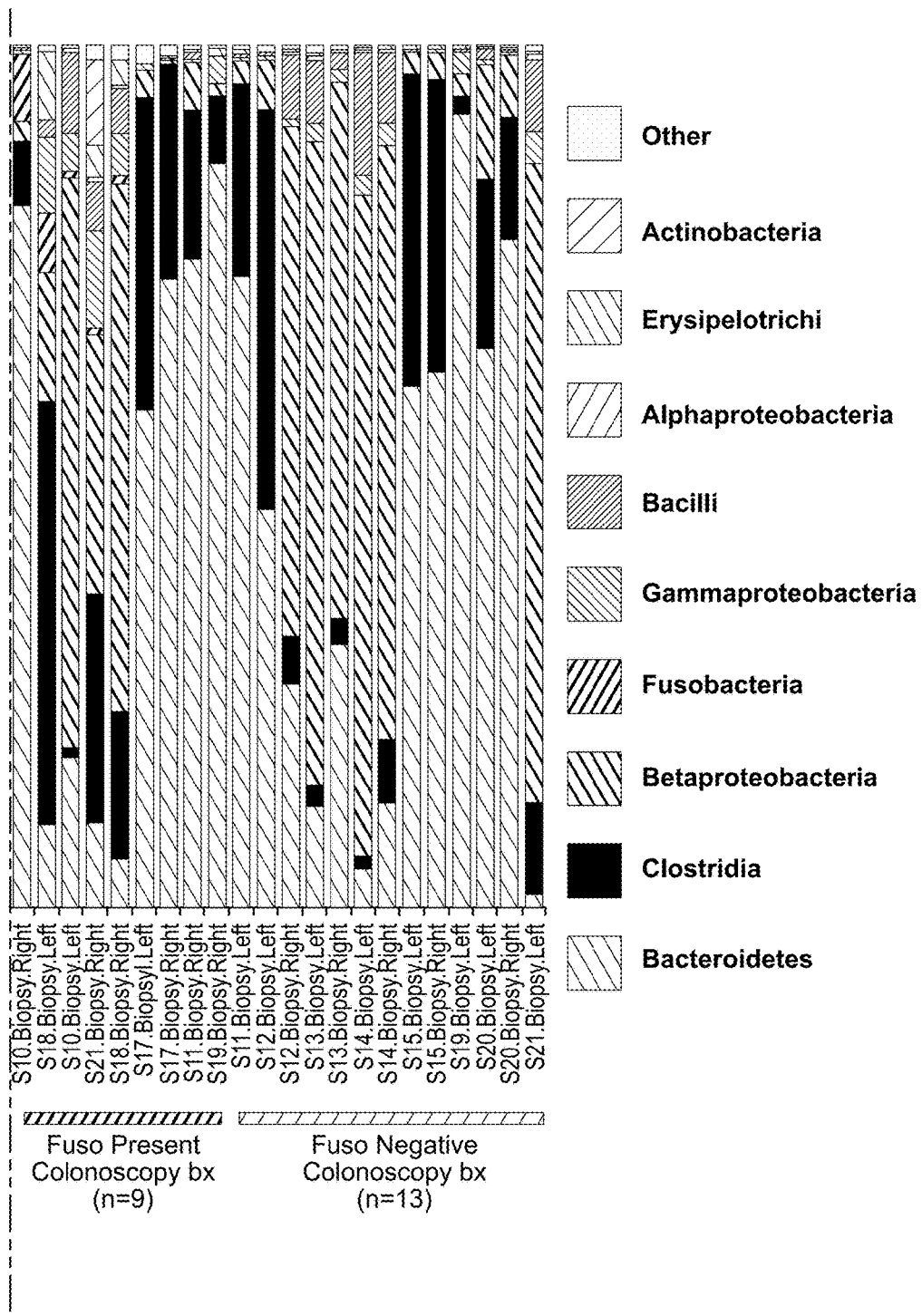
Figure 8:
FIG. 8 shows an example of an infrequent H2AX positive cell from a surgically resected distal normal tissue sample.
Figure 13C:
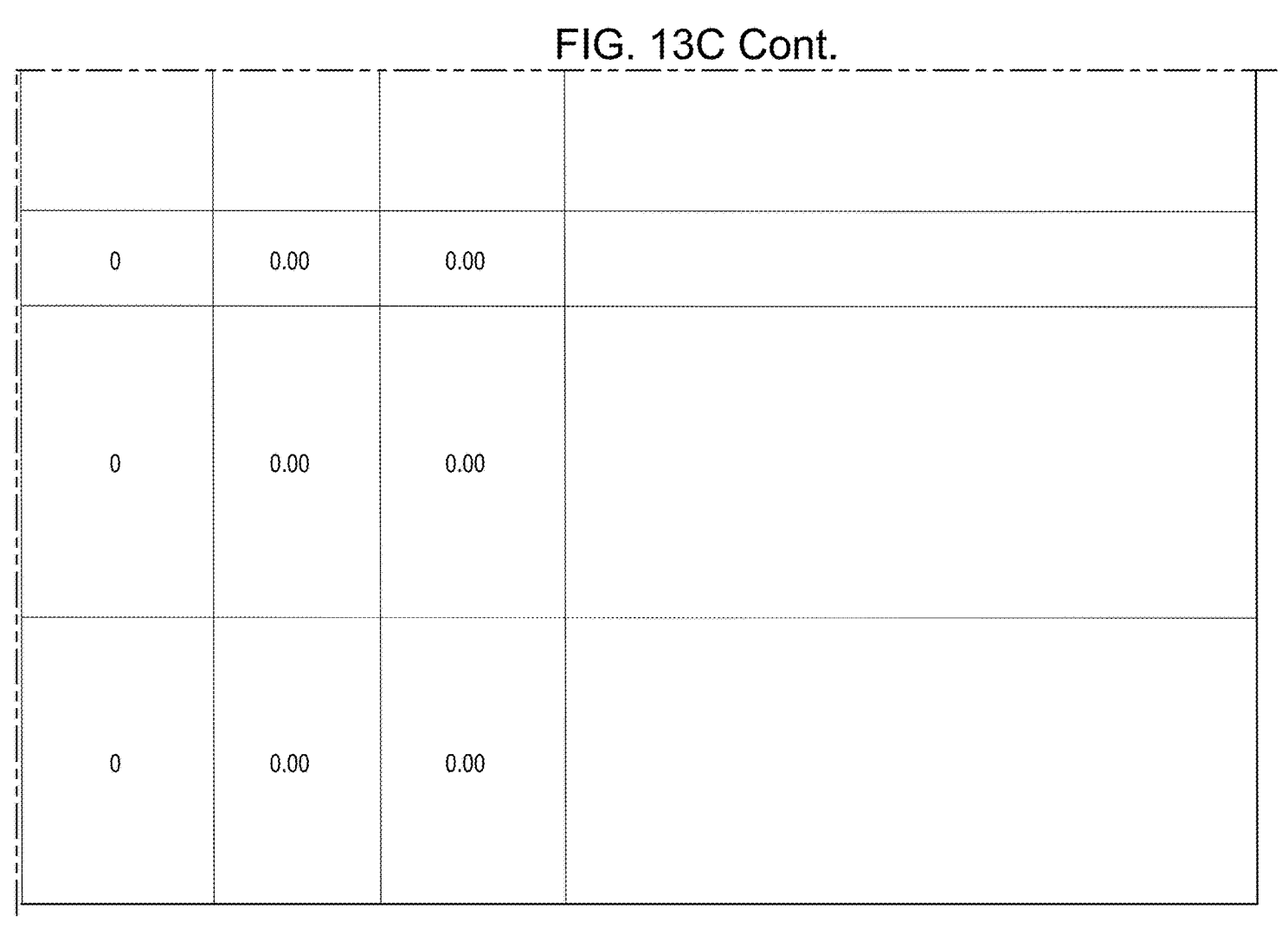
Figure 13D:

Sequence analysis revealed substantial overlap between tumors (adenomas or CRCs) and surgically-resected distal normal tissue bacterial membership at the genus level; tumor bacterial membership was a complete subset of their distal normal pair in 52% of tumor:distal normal sets (FIGS. 13A-13H). Among the 25 tumor:distal normal paired tissue samples, eight CRCs (32%, 4 right and 4 left), but not their paired surgically-resected distal normal tissues, were Fusobacteria dominant (>25% of total sequences; FIG. 2E and FIG. 7) (7,8). No biopsies from healthy controls displayed dominant membership of Fusobacteria (FIG. 2E and FIG. 7). Although analysis methods differ, prior data supported that a subset of CRCs and adenomas displayed a Fusobacteria-dominant microbiota membership (7-10).

Due to high variability in taxonomic structure among tumor samples, no differentially abundant taxa were detected between biofilm positive (N=14) and negative tumors (N=11) (FIGS. 2E, 2F, and FIGS. 14A-14G). Similarly, the microbial community structure of colonoscopy control biopsies did not differ significantly from surgically-resected distal normal biofilm-negative tissues. However, nine differentially abundant genus level groups were detected in colonoscopy biopsies compared to surgically-resected distal normal biofilm-positive tissue samples (FDR<3%) including significant enrichment of *Lactococcus; Leuconostoc*; and *Comamonas* and other Burkholderiales members in colonoscopy biopsies, and, conversely, a 10-fold relative increase of a candidate Ruminococcaceae member in surgically-resected distal normal biofilm-positive tissue samples. In contrast, significant depletion of Bacilli and some Bacteroidetes members was detected in surgically-resected distal normal biofilm-positive tissue samples, with on average 28- and 7-fold lower relative abundance than surgically-resected distal normal biofilm-negative samples, respectively (FDR<5%). None of the control colonoscopy biopsies sequenced exhibited a biofilm and no significant differences were detected in the microbial communities on right vs. left colonoscopy biopsies.

The differences between tissues with and without a biofilm were highlighted by principal coordinate analysis (PCoA). Unweighted UniFrac distance metric revealed discrete clustering of normal colonoscopy biopsies relative to tumor-associated communities (FIG. 2F); surgically-resected distal normal tissue communities with a biofilm were on average significantly closer in community structure to tumor populations than colonoscopy biopsies (P=0.019, Mann-Whitney test) suggesting biofilm presence correlates with the dysbiosis detected within the tumor-associated microbiota. These findings suggested that stepwise colon mucosal microbial community dysbiosis, largely with depletion of common microbiota community members, paralleled the transition from normal colon mucosa to CRC.

Because dysbiosis might have affected generation of specific oncogenic mutational events or selectively expanded pre-malignant or malignant clones bearing specific oncogenic mutations, potential relationships between biofilm formation and common CRC mutations were studied. Specifically, the molecular profiles (KRAS and BRAF mutations and MSI status) of 15 biofilm-covered CRCs and 16 biofilm-negative CRCs were analyzed. BRAF mutations were detected in 4/15 biofilm-covered CRCs (3 right and 1 left) and 0/16 biofilm-negative CRCs (P=0.043). In contrast, neither KRAS mutations nor MSI status differed between biofilm-positive or negative CRCs (FIG. 15). Of note, increased BRAF mutations have been associated with the inflammatory response in many human cancers, including CRC (11).

Example 4: Biofilm Formation Impacted Epithelial Biology

Beyond potential effects on specific oncogenic mutations, a critical question raised by these findings was whether biofilm presence modified epithelial biology before onset of tumor initiation and the immune dysregulation of tumorigenesis. To test the impact of biofilm formation on epithelial biology, immunohistological analyses of proliferation, apoptosis and DNA damage of surgically-resected distal normal tissues from CRC patients and normal colonoscopy biopsies were conducted. A significant increase in crypt epithelial cell proliferation was detected, as measured by Ki67 staining, in surgically-resected distal normal tissues covered with a biofilm (including left-sided biofilm-positive tumors) compared to such tissues without a biofilm (P<0.0001, FIG. 3A). Notably, significant increased proliferation was also found on biofilm-positive colonoscopy biopsies from healthy individuals (P<0.01, FIG. 3B). In parallel, TUNEL staining revealed less frequent epithelial cell apoptosis from surgically-resected biofilm-positive distal normal tissues (including biofilm-positive tumors from the left colon) compared to distal normal tissues without a biofilm (P<0.001, FIG. 3C). No difference in epithelial cell apoptosis was found between colonoscopy biopsies with and without a biofilm (P>0.05, FIG. 3D). Thus, biofilm-positive normal colon epithelium either in a tumor host or colonoscopy control exhibited a pro-tumorigenic balance of enhanced colon epithelial proliferation whereas diminished apoptosis appeared in the tumor host. Spearman correlations between Ki67 staining and genus-level relative abundances were sought in samples stratified by biofilm positive and negative status. No genera were significantly correlated with the Ki67 counts in any subgroup. There was limited detection of DNA damage by H2AX staining, consistent with past reports in CRC (12).

Thus, virtually all right-sided CRCs were associated with a dense bacterial biofilm and paired distal normal colonic mucosa from patients with biofilm positive tumors (even the infrequent biofilm-positive left-sided CRCs) were always biofilm positive. None of the non-tumor involved colonic mucosa from patients with biofilm negative CRC possessed a biofilm. These findings identify the organization (bacterial structure), as opposed to the specific composition, of the mucosa-associated microbial community as an important factor in CRC pathogenesis. Based on these findings and the findings that a small fraction of colonic specimens from non-cancer-bearing individuals possessed a biofilm, it was proposed that biofilm formation (and its associated dysbiosis) preceded and likely contributed to CRC formation or propagation.

REFERENCES

1. C. Dejea, E. Wick, C. L. Sears, Bacterial oncogenesis in the colon. Future Microbiol. 8, 445-460 (2013).
2. J. S. Finkel, A. P. Mitchell, Genetic control of *Candida albicans* biofilm development. Nat. Rev. Microbiol. 9, 109-118 (2011).
3. A. Swidsinski, J. Weber, V. Loening-Baucke, L. P. Hale, H. Lochs, Spatial organization and composition of the mucosal flora in patients with inflammatory bowel disease. J. Clin. Microbiol. 43, 3380-3389 (2005).
4. S. Ahmed et al., Mucosa-associated bacterial diversity in relation to human terminal ileum and colonic biopsy samples. Appl. Environ. Microbiol. 73, 7435-7442 (2007).

5. M. E. Johansson, J. M. Larsson, G. C. Hansson, The two mucus layers of colon are organized by the MUC2 mucin, whereas the outer layer is a legislator of host-microbial interactions. Proc. Natl. Acad. Sci. U.S.A 108 Suppl 1, 4659-4665 (2011).

6. A. Swidsinski et al., Comparative study of the intestinal mucus bather in normal and inflamed colon. Gut. 56, 343-350 (2007).

7. A. D. Kostic et al., Genomic analysis identifies association of *Fusobacterium* with colorectal carcinoma. Genome Res. 22, 292-298 (2012).

8. A. D. Kostic et al., *Fusobacterium nucleatum* Potentiates Intestinal Tumorigenesis and Modulates the Tumor-Immune Microenvironment. Cell. Host Microbe. 14, 207-215 (2013).

9. M. Castellarin et al., *Fusobacterium nucleatum* infection is prevalent in human colorectal carcinoma. Genome Res. 22, 299-306 (2012).

10. A. N. McCoy et al., *Fusobacterium* is associated with colorectal adenomas. PLoS One. 8, e53653 (2013).

11. I. Zlobec, M. P. Bihl, H. Schwarb, L. Terracciano, A. Lugli, Clinicopathological and protein characterization of BRAF- and K-RAS-mutated colorectal cancer and implications for prognosis. Int. J. Cancer. 127, 367-380 (2010).

12. P. G. Nuciforo, C. Luise, M. Capra, G. Pelosi, F. d'Adda di Fagagna, Complex engagement of DNA damage response pathways in human cancer and in lung tumor progression. Carcinogenesis. 28, 2082-2088 (2007).

13. T. Morikawa et al., STAT3 expression, molecular features, inflammation patterns, and prognosis in a database of 724 colorectal cancers. Clin. Cancer Res. 17, 1452-1462 (2011).

14. M. Tosolini et al., Clinical impact of different classes of infiltrating T cytotoxic and helper cells (Th1, th2, treg, th17) in patients with colorectal cancer. Cancer Res. 71, 1263-1271 (2011).

15. B. Vogelstein, K. W. Kinzler, The multistep nature of cancer. Trends Genet. 9, 138-141 (1993).

16. J. A. Bufill, Colorectal cancer: evidence for distinct genetic categories based on proximal or distal tumor location. Ann. Intern. Med. 113, 779-788 (1990).

17. F. Benedix et al., Comparison of 17,641 patients with right- and left-sided colon cancer: differences in epidemiology, perioperative course, histology, and survival. Dis. Colon Rectum. 53, 57-64 (2010).

18. R. I. Amann et al., Combination of 16S rRNA-targeted oligonucleotide probes with flow cytometry for analyzing mixed microbial populations. Appl. Environ. Microbiol. 56, 1919-1925 (1990).

19. A. M. Valm et al., Systems-level analysis of microbial community organization through combinatorial labeling and spectral imaging. Proc. Natl. Acad. Sci. U.S.A 108, 4152-4157 (2011).

20. P. I. Diaz et al., Molecular characterization of subject-specific oral microflora during initial colonization of enamel. Appl. Environ. Microbiol. 72, 2837-2848 (2006).

21. R. Weller, F. O. Glockner, R. Amann, 16S rRNA-targeted oligonucleotide probes for the in situ detection of members of the phylum Cytophaga-*Flavobacterium-Bacteroides*. Syst. Appl. Microbiol. 23, 107-114 (2000).

22. Y. Kong, M. He, T. McAlister, R. Seviour, R. Forster, Quantitative fluorescence in situ hybridization of microbial communities in the rumens of cattle fed different diets. Appl. Environ. Microbiol. 76, 6933-6938 (2010).

23. V. A. Kempf, K. Trebesius, I. B. Autenrieth, Fluorescent In situ hybridization allows rapid identification of microorganisms in blood cultures. J. Clin. Microbiol. 38, 830-838 (2000).

24. A. Neef, R. Amann, K. Schleifer, Detection of Microbial Cells in Aerosols Using Nucleic Acid Probes. Syst. Appl. Microbiol. 18, 113-122 (1995).

25. G. Wallner, R. Amann, W. Beisker, Optimizing fluorescent in situ hybridization with rRNA-targeted oligonucleotide probes for flow cytometric identification of microorganisms. Cytometry. 14, 136-143 (1993).

26. L. Rigottier-Gois, V. Rochet, N. Garrec, A. Suau, J. Dore, Enumeration of *Bacteroides* species in human faeces by fluorescent in situ hybridisation combined with flow cytometry using 16S rRNA probes. Syst. Appl. Microbiol. 26, 110-118 (2003).

27. Paster B J, Bartoszyk I M, Dewhirst F E, Identification of oral streptococci using PCR-based, reverse-capture, checkerboard hybridization. Methods Cell Sci. 20, 223 (1998).

28. W. Manz, R. Amann, W. Ludwig, M. Wagner, K. Schleifer, Phylogenetic Oligodeoxynucleotide Probes for the Major Subclasses of Proteobacteria: Problems and Solutions. Syst. Appl. Microbiol. 15, 593-600 (1992).

29. A. Swidsinski, J. Weber, V. Loening-Baucke, L. P. Hale, H. Lochs, Spatial organization and composition of the mucosal flora in patients with inflammatory bowel disease. J. Clin. Microbiol. 43, 3380-3389 (2005).

30. J. Kuczynski et al., Using QIIME to analyze 16S rRNA gene sequences from microbial communities. Curr. Protoc. Microbiol. Chapter 1, Unit 1E.5. (2012).

31. J. G. Caporaso et al., QIIME allows analysis of high-throughput community sequencing data. Nat. Methods. 7, 335-336 (2010).

32. L. Bragg, G. Stone, M. Imelfort, P. Hugenholtz, G. W. Tyson, Fast, accurate error-correction of amplicon pyrosequences using Acacia. Nat. Methods. 9, 425-426 (2012).

33. R. C. Edgar, B. J. Haas, J. C. Clemente, C. Quince, R. Knight, UCHIME improves sensitivity and speed of chimera detection. Bioinformatics. 27, 2194-2200 (2011).

34. Q. Wang, G. M. Garrity, J. M. Tiedje, J. R. Cole, Naive Bayesian classifier for rapid assignment of rRNA sequences into the new bacterial taxonomy. Appl. Environ. Microbiol. 73, 5261-5267 (2007).

35. S. V. Angiuoli et al., CloVR: a virtual machine for automated and portable sequence analysis from the desktop using cloud computing. BMC Bioinformatics. 12, 356-2105-12-356 (2011).

36. P. D. Schloss et al., Introducing mothur: open-source, platform-independent, community-supported software for describing and comparing microbial communities. Appl. Environ. Microbiol. 75, 7537-7541 (2009).

37. C. Lozupone, M. E. Lladser, D. Knights, J. Stombaugh, R. Knight, UniFrac: an effective distance metric for microbial community comparison. ISME J. 5, 169-172 (2011).

The invention claimed is:

1. A method for treating colorectal cancer or a colorectal adenoma in a subject comprising:
   (i) detecting a bacterial biofilm on mucosa within the gastrointestinal tract of a subject, wherein said bacterial biofilm consists of Bacteroidetes, Firmicutes, Gammaproteobacteria, Fusobacteria, and Lachnospiraceae; and
   (ii) administering an antimicrobial agent or a probiotic agent to said subject in an amount effective to reduce the size and/or density of bacteria of said bacterial biofilm, thereby treating colorectal cancer or a colorectal adenoma in said subject.

2. The method of claim 1, wherein said bacterial biofilm is detected within mucosa of the colon of said subject.

3. The method of claim 1, wherein said bacterial biofilm has invaded the mucus layer of said gastrointestinal tract of said subject.

4. The method of claim 1, wherein said bacterial biofilm occupies a linear distance of at least 150 µm of the epithelial surface.

5. The method of claim 1, wherein the density of bacteria in said bacterial biofilm is at least $10^8$ bacteria/ml.

6. The method of claim 1, wherein said Lachnospiraceae is selected from the group consisting of *Clostridium, Ruminococcus*, and/or *Butyrivibrio*.

7. The method of claim 1, wherein said bacterial biofilm comprises a Fusobacteria-dominant microbiota membership.

8. The method of claim 1, wherein said detecting step comprises colonoscopy or administering a bacteria visualizing agent or biofilm visualizing agent to said subject or a sample of said subject.

9. The method of claim 8, wherein said bacteria visualizing agent or biofilm visualizing agent is a fluorescence in situ hybridization (FISH) probe or other bacteria labeling agent or labeling agent taken up by polymeric matrix of the biofilm, wherein said FISH probe or other bacteria labeling agent or labeling agent taken up by polymeric matrix of the biofilm is selected from Eub338, Fus714, PRV392, CFB286, Bet42a, Gam42a, Lac435, Ent186, S-S-Bfrag-998-a-A-20, Eco1167, Str405 and non338.

10. The method of claim 1, wherein said detecting step comprises administering a FISH probe or other bacteria labeling agent or label of the polymeric biofilm matrix to the colon mucosa of said subject, optionally during colonoscopy.

11. The method of claim 1, wherein said antimicrobial agent is an antibiotic, wherein said antibiotic is selected from the group consisting of clindamycin, beta-lactams, macrolides, chloramphenicol, aminoglycosides, fluoroquinolones, carbapenems and sulbactam.

12. The method of claim 1, wherein said probiotic agent comprises one or more species of selected from the group consisting of *Bacteroides, Prevotella, Porphyromonas, Fusobacterium, Sutterella, Bilophila, Campylobacter, Wolinella, Butyrovibrio, Megamonas, Desulfomonas, Desulfovibrio, Bifidobacterium, Lactobacillus, Eubacterium, Actinomyces, Eggerthella, Coriobacterium, Propionibacterium*, other genera of non-spore-forming anaerobic gram-positive bacilli, *Bacillus, Peptostreptococcus* (and newly created genera originally in *Peptostreptococcus*), *Peptococcus, Acidaminococcus, Ruminococcus, Megasphaera, Gaffkya, Coprococcus, Veillonella, Sarcina, Clostridium, Aerococcus, Streptococcus, Enterococcus, Pediococcus, Micrococcus, Staphylococcus, Corynebacterium*, and species of the genera comprising the Enterobacteriaceae and Pseudomonadaceae.

13. The method of claim 1, wherein said detecting step comprises identification of bacterial species or polymeric biofilm matrix within a sample of said subject, wherein said sample of said subject is a colonic biopsy sample or a stool sample, wherein said identification comprises detection of bacterial DNA or RNA sequences or polymeric biofilm matrix.

14. The method of claim 1, wherein said antimicrobial agent reduces colon epithelial proliferation or increases apoptosis in the colon cells of said subject, optionally in colon tumor cells of said subject.

15. The method of claim 1, wherein said detecting step comprises identification of a reduced level of a candidate Ruminococcaceae member, Bacilli or Bacteroidetes in said subject.

16. The method of claim 1, further comprising administering a chemotherapeutic agent to said subject.

17. The method of claim 1, further comprising detecting mucosal biofilm-specific bacteria in a subject's stool.

18. The method of claim 1, wherein said bacterial biofilm comprises a Proteobacteria-dominant microbiota membership.

19. The method of claim 1, wherein said bacterial biofilm comprises a Bacteroidetes-dominant microbiota membership.

20. The method of claim 1, wherein said bacterial biofilm comprises a Lachnospiraceae-dominant microbiota membership.

21. A method for treating colorectal cancer or a colorectal adenoma in a subject comprising administering an antimicrobial agent or a probiotic agent to a subject harboring a bacterial biofilm consisting of Bacteroidetes, Firmicutes, Gammaproteobacteria, Fusobacteria, and Lachnospiraceae within the gastrointestinal tract of said subject, wherein said antimicrobial agent or probiotic agent reduces or eliminates the presence of a said biofilm, thereby treating cancer in said subject.

* * * * *